United States Patent
Sauvé et al.

(10) Patent No.: US 6,362,165 B1
(45) Date of Patent: Mar. 26, 2002

(54) HYDROXYPHENYL DERIVATIVES WITH HIV INTEGRASE INHIBITORY PROPERTIES

(75) Inventors: Gilles Sauvé; Jocelyn Yelle, both of Laval (CA)

(73) Assignee: Pharmacor Inc., Laval (CA)

( * ) Notice: Subject to any disclaimer, the term of this patent is extended or adjusted under 35 U.S.C. 154(b) by 0 days.

(21) Appl. No.: 09/534,615

(22) Filed: Mar. 27, 2000

Related U.S. Application Data

(63) Continuation-in-part of application No. 09/280,569, filed on Mar. 30, 1999, now abandoned.

(51) Int. Cl.$^7$ .................... A61K 31/166; A61K 31/192; A61K 31/404; A61K 31/4164; A61K 38/05

(52) U.S. Cl. .................... 514/19; 514/20; 514/400; 514/419; 514/423; 514/563; 514/616; 548/338.1; 548/491; 548/537; 562/448; 562/451; 562/455; 564/153; 564/157; 564/158

(58) Field of Search .................... 514/19, 20, 400, 514/419, 423, 563, 616; 548/338.1, 491, 537; 562/448, 451, 455; 564/153, 157, 158

(56) References Cited

U.S. PATENT DOCUMENTS

| | | | | |
|---|---|---|---|---|
| 4,105,787 A | * | 8/1978 | Jones et al. .................. | 560/109 |
| 5,686,423 A | * | 11/1997 | Wang et al. .................. | 514/18 |
| 5,811,512 A | | 9/1998 | Hirschmann et al. ....... | 530/311 |
| 5,939,414 A | * | 8/1999 | Bell et al. .................... | 514/221 |

FOREIGN PATENT DOCUMENTS

| | | |
|---|---|---|
| DK | A-3239858 | 1/1984 |
| EP | 0 098600 A | 1/1984 |
| GB | 2327674 | * 2/1999 |
| WO | WO A 9200948 | 1/1992 |
| WO | WO-A-9216501 | 10/1992 |
| WO | WO94/13629 | 6/1994 |
| WO | WO 9417096 A | 8/1994 |
| WO | WO 9818473 A | 5/1998 |
| WO | WO 9850347 A | 11/1998 |
| WO | WO 00/66524 | 9/2000 |
| WO | WO 00/59867 | 10/2000 |

OTHER PUBLICATIONS

J. Med. Chem. 40 (6) 885–897 (1997).
Lasky L.A, et al., Cell. vol. 50, pp. 975–985 (1987).
Haseltine W. A. FASEB J. vol. 5 2349–2360 (1991).
Goff S. P. J. Acq. Imm.Defic.Sydr., vol. 3, pp. 817–831 (1990).
Sakai, H et al, J. Virol, vol. 67, pp. 1169–1174 (1993).
Bukrinsky et al., Proc. Acad, Sci. USA, vol. 89, pp. 6580–6584 (1992).
T.W. Greene, Protecting Groups in Organic Synthesis, John Wiley and Sons (1999) (title & copyright pages only).

Bouzide A. et al, Tet. Letters vol. 38, pp. 5945–5948 (1997).
Gallay et al., Cell. vol. 80, pp. 379–388 (1995).
Inhibition of HIV–1 protease in infected T–lymphocytes by synthetic peptide analogues, Letters to Nature, vol. 343, pp. 90 to 92 (1990).
Delineation of a Region of the Human Immunodeficiency Virus Type 1 gp 120 glycoprotein critical for interaction with the CD4 receptor, Cell. vol. 50, 975–985, Sep. 11, 1987, pp. 975 to 985.
Molecular biology of the human immunodeficiency virus type 1, The Faseb Journal, pp. 2349 to 2360, vol. 5 (Jul. 1991).
Journal of the American Chemical Society, vol. 118, No. 33, pp. 7647 to 7652 (Aug. 21, 1996).

(List continued on next page.)

*Primary Examiner*—Jeffrey E. Russel
(74) *Attorney, Agent, or Firm*—Ronald S. Kosie; Robert Brouillette

(57) ABSTRACT

An hydroxyphenyl derivative selected from the group consisting of a compound of formula

I

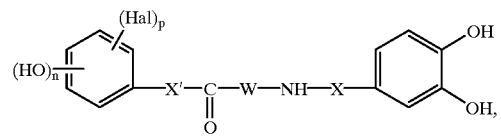

II

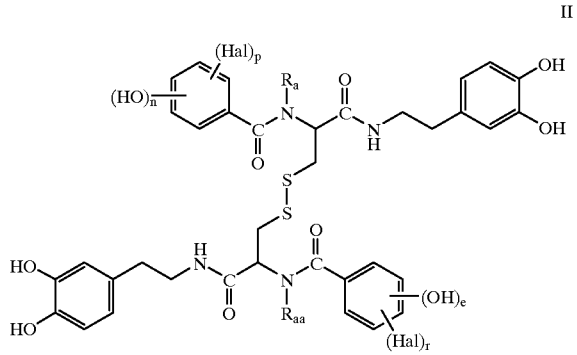

and when a compound of formula I comprises a carboxylic acid group pharmaceutically acceptable salts thereof and when a compound of formula I comprises an amino group pharmaceutically acceptable ammonium salts thereof, wherein n is 1, 2 or 3, e is 1, 2 or 3, Hal represents a halogen atom (e.g. Cl, Br, F or I), p is 0, 1 or 2, r is 0, 1 or 2, X and X' each independently represents a single bond, a saturated straight or branched hydrocarbon group of 1 to 4 carbon atoms or a straight or branched hydrocarbon group of 2 to 4 carbon atoms comprising a carbon to carbon double bond, $R_a$ represents H or —$CH_3$, and $R_{aa}$ represents H or —$CH_3$; W may represent an amino acid residue or fragment. These compounds may be used to inhibit the activity of HIV integrase.

73 Claims, No Drawings

OTHER PUBLICATIONS

Chemical Abstracts, vol. 101, No. 1, H. Eibl "D–mannitol derivatives as raw products for the synthesis of phospolipids". (1984), 101:6942j.

Chemical Abstracts, vol. 82, No. 5, A. I. Gurevich: "Synthesis sof (2S, 5S)–2, 5–dimethoxyadipic acid". . . XP002146942, 82:30908n(1975).

Chemical Abstracts, vol. 77, No. 1, C.E. Ballou "L–glycero–tetrulose (L–erythrulose) 1–posphate", 77:5720j (1972).

Chemical Abstracts, vol. 103, No. 7, L.V. Bakinovskii et al "1, 2–0–Cyanoalkylidene derivatives of furanose as 1, 2–trans–glycosylating agents", 103:54378t (1985).

Journal of the Chemical Society, Morpain Perkin Transactions 1, "A possible model for a new chiral glyceride synthesis" pp. 1379 to 1383 (1979).

Journal of Medicinal Chemistry, vol. 34, No. 8, pp. 2305–2314 (Aug. 1991).

HE Zhao et al. "Coumarin based inhibitors of HIV integrase", Journal of Medical Chemistry, US, American Chemical Society, Washington, vol. 40, No. 2, pp. 242–249 (1997).

Chemical Abstract, vol. 119, No. 21, A.N. Pinchuck: "Synthesis of enantiomerically pure ether lipid analogs from D–mannitol". . . XP2146941, 119:226299s (1993).

A. Bouzide: "Lewis acid–catalyzed deprotection of p–metoxybenzyl ether". . . XP002146936, SynLett, pp. 1153–1154 (Oct. 1997).

K. Fukase: "Synthetic study of lipoteichoic acid of gram positive bacteria. I. Synthesis of proposed fundamental structure of Streptococcus pyogenes lipoteichoic acid". . . XP002146937, Bull. Chem. Soc. Jpn., vol. 65, pp. 2643–2654 (1992).

M. Fedeoronko: "Kinetics and mechanism of the acid–catalyzed reactions of methylated trioses". . . XP002146938, Carb. Res., vol. 87, pp. 51–62 (1980).

J.W. Van Cleve: "Syntheses of 3(4)–0–allyl–, 3(4)–0–benzyl–and 1,2,3(4),5,6–penta–0–benzoyl–D–mannitol". . . XP002146939, Carb.Res., vol. 106, pp. 70–173 (1982).

G. Zuccarello: "HIV–1 Protease inhibitors based on acyclic carbohydrates". . . XP002146940 J.Org.Chem., vol. 63, pp. 4898–4906 (1998).

U. Peters: "Platelet activating factor synthetic studies". . . XP002146935 Tet., vol. 43, No. 16, pp. 3803–3816 (1987).

Xiaoming Fu "Sythèse d'acides aminés et de dérivés d'acide afféique comme inhibiteurs du VIH–1 intégrase" Jun. 11, 1999.

F. Deschamps Synthèse de dérivés d'acides aminés comme inhibiteurs de l'intégrase du VIH–1 et synthèse de dérivés triaminés comme inhibiteurs de la protéase du VIH–1, Mar. 2, 1998.

Mazumber "Virus Type 1 Integrase" American Chemical Society 1995.

Robinson, "Dicaffeoylquinic Acid Inhibitors of Human Immunodeficiency Virus Integrase: Inhibition of the Core Catalytic domain of human immunodeficiency virus integrase" (not dated).

Journal of Medical Chemistry, 1999, vol. 42, pp. 497 to 509.

Journal of Medical Chemistry 1998, vol. 41, pp. 3202 to 3209.

Neamati, "Depsides and Depsidones as Inhibitors of HIV–1 Integrase: Discovery of Novel Inhibitors through 3D Database Searching" (1997).

Zhao, "Hydrazide–containing inhibitors of HIV–1 integrase", J.Med. Chem., vol. 40, No. 6 (1997).

Burke, "Hydroxylated Aromatic Inhibitors of HIV–1 Integrase" (1995).

Fesen, "Inhibition of HIV–1 integrase by flavones, caffeic acid phenethyl ester (Cape) and related compounds" (1994).

Artico, ". . . Compounds as inhibitors of HIV–1 integrase: Synthesis, Biological Evaluation, and Molecular Modeling" (1998).

Laboratories of Medicinal Chemistry and Molecular Pharmacology, Division of Basic Sciences, National Cancer Institute, . . . (1997).

Fesen, Mark R. et al., pp. 2399–2403 (1993).

\* cited by examiner

HYDROXYPHENYL DERIVATIVES WITH HIV INTEGRASE INHIBITORY PROPERTIES

The present is a continuation-in-part of U.S. patent application Ser. No. 09/280,569 filed Mar. 30, 1999, now abandoned.

TECHNICAL FIELD OF THE INVENTION

The present invention relates to a hydroxyphenyl derivatives which have HIV integrase inhibitory properties that have been characterized by specific structural and physicochemical features. This inhibitory property may be advantageously used, for example, to provide medicinals (e.g. compositions) with antiviral properties against HIV viruses, including the HIV-1 and HIV-2 viruses, i.e. the hydroxyphenyl derivatives including pharmaceutical compositions thereof may be used to inhibit the activity of HIV integrase.

BACKGROUND OF THE INVENTION

The HIV (human immunodeficiency virus) retrovirus is the causative agent for AIDS (acquired immunodeficiency syndrome). Thus the HIV-1 retrovirus primarily uses the CD4 receptor (a 58 kDa transmembrane protein) to gain entry into cells, through high-affinity interactions between the viral envelope glycoprotein (gp 120) and a specific region of the CD4 molecule found in T-lymphocytes and CD4 (+) T-helper cells (Lasky L. A. et al., Cell vol. 50, p. 975–985 (1987)). HIV infection is characterized by a period immediately following infection called "asymptomatic" which is devoid of clinical manifestations in the patient. Progressive HIV-induced destruction of the immune system then leads to increased susceptibility to opportunistic infections, which eventually produces a syndrom called AIDS-related complex (ARC) characterized by symptoms such as persistent generalized lymphadenopathy, fever, weight loss, followed itself by full blown AIDS. After entry of the retrovirus into a cell, viral RNA is converted into DNA, which is then integrated into the host cell DNA. The reverse transcriptase encoded by the virus genome catalyzes the first of these reactions (Haseltine W. A. FASEB J. vol 5, p. 2349–2360 (1991)). At least three functions have been attributed to the reverse transcriptase: RNA-dependent DNA polymerase activity which catalyzes the synthesis of the minus strand DNA from viral RNA, ribonuclease H (RNase H) activity which cleaves the RNA template from RNA-DNA hybrids and DNA-dependent DNA polymerase activity which catalyzes the synthesis of a second DNA strand from the minus strand DNA template (Goff S. P. J. Acq. Imm. Defic. Syndr. Vol 3, p. 817–831 (1990)). The double stranded DNA produced by reverse transcriptase, now called provirus, is then able to be inserted into host genomic DNA. At the end of reverse transcription, the viral genome now in the form of DNA is integrated into host genomic DNA and serves as a template for viral gene expression by the host transcription system, which leads eventually to virus replication (Roth et al.,1989). The preintegration complex consists of integrase, reverse transcriptase, p17 and proviral DNA (Bukrinsky M. I., Proc. Natn. Acad. Sci. USA vol. 89 p.6580–6584 (1992)). The phosphorylated p17 protein plays a key role in targeting the preintegration complex into the nucleus of host cell (Gallay et al., 1995).

The primary RNA transcripts made from the provirus are synthesized by the host cell RNA polymerase II which is modulated by two virus-encoded proteins called tat and rev. The viral proteins are formed as polyproteins.

Post-translational modifications of viral polyproteins include processing and glycosylation of Env (envelope) proteins, and myristylation of the N-terminal residue of the p17 protein in the Gag and Gag-Pol polyproteins. The latter two precursors correspond to structural proteins and viral enzymes. The viral protease is involved in processing polyproteins Gag and Gag-Pol into mature proteins, a step essential for virus infectivity.

A number of synthetic antiviral agents have been designed to block various stages in the replication cycle of HIV. These agents include compounds which interfere with viral binding to CD4 T-lymphocytes (for example, soluble CD4), compounds which block viral reverse transcriptase (for example, didanosine and zidovudine (AZT)), budding of virion from the cell (interferon), or the viral protease (for example Ritonavir and Indinavir). Some of these agents proved ineffective in clinical tests. Others, targeting primarily early stages of viral replication, have no effect on the production of infectious virions in chronically infected cells. Furthermore, administration of many of these agents in effective therapeutic doses has led to cell-toxicity and unwanted side effects, such as anemia, neurotoxicity and bone marrow suppression. Anti-protease compounds in their present form are typically large and complex molecules of peptidic nature that tend to exhibit poor bioavailability and are not generally consistent with oral administration. These compounds often exhibit side effects such as nausea, diarrhea, liver abnormalities and kidney stones.

Accordingly, the need exists for compounds that can effectively inhibit the action of the third viral enzyme called integrase, for use as agents for treating HIV infections.

The terms HIV integrase and integrase as used herein are used interchangeably and refer to the integrase enzyme encoded by the human immunodeficiency virus type 1 or 2. In particular this term includes the human immunodeficiency virus type 1 integrase.

SUMMARY OF THE INVENTION

The present invention provides an hydroxyphenyl derivative selected from the group consisting of a compound of formula

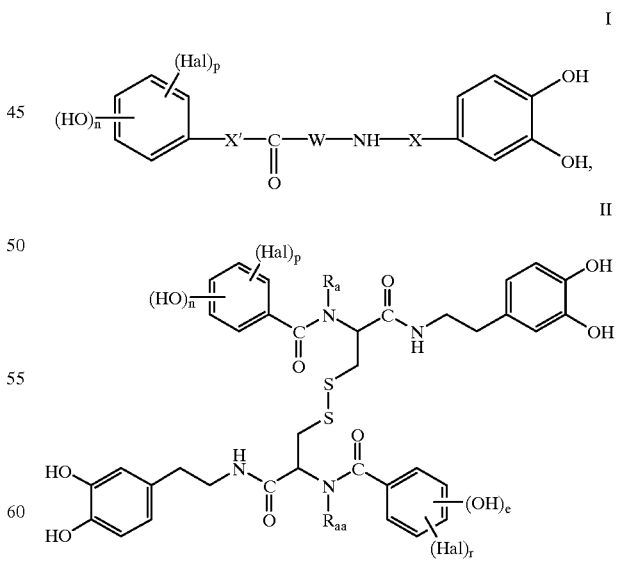

and when a compound of formula I comprises a carboxylic acid group pharmaceutically acceptable salts thereof and when a compound of formula I comprises an amino group pharmaceutically acceptable ammonium salts thereof, wherein n is 1, 2 or 3, e is 1, 2 or 3, Hal represents a halogen atom (e.g. Cl, Br, F or I), p is 0, 1 or 2, r is 0, 1 or 2, X and X' each independently represents a single bond, a saturated straight or branched hydrocarbon group of 1 to 4 carbon atoms or a straight or branched hydrocarbon group of 2 to 4 carbon atoms comprising a carbon to carbon double bond, $R_a$ represents H or —$CH_3$, and $R_{aa}$ represents H or —$CH_3$; W, may for example, represent an amino acid residue or fragment (in particular alpha-amino acid residues) such as for example a residue based on tyrosine, DOPA, hydroxyproline, serine, threonine, histidine, valine, phenylalanine, lysine, alanine, glycine, glutamic acid, aspartic acid, arginine, asparagine, glutamine, leucine, lysine, isoleucine, proline, tryptophan, methionine, cysteine, cystine, thyroxine, meta-tyrosine, sarcosine, other alpha-methyl amino acids such as alpha-methyl DOPA, as well as other 3-substituted tyrosines, and the like.

W, for the above formula I, may, for example, be derived from natural or unnatural alpha-amino acids. The term unnatural alpha-amino acid refers to alpha-amino acids which do not occur in nature but which can be derived from naturally occurring alpha-amino acids or other chemical reagents by methods known to those skilled in the art.

W may, for example, represent a group of formula

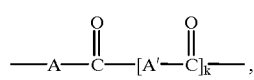

wherein k is 0 or 1, A and A' each independently represents a group of formula

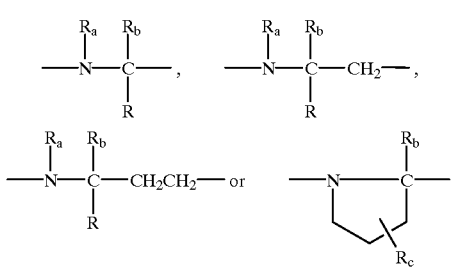

$R_a$ represents H or —$CH_3$, $R_b$ represents H or —$CH_3$, $R_c$ represents H or OH, R is selected from the group consisting of H, $CH_3$—, $(CH_3)_2CH$—, $(CH_3)_2CHCH_2$—, $CH_3CH_2CH(CH_3)$—, $C_6H_5CH_2$—, $CH_3SCH_2CH_2$—, $HO_2CCH_2$—, $H_2NC(O)CH_2$—, $HO_2CCH_2CH_2$—, $H_2NC(O)CH_2CH_2$—, $H_2NCH_2CH_2CH_2CH_2$—, $HOCH_2$—, $CH_3CH(OH)$—, $HSCH_2$—, $HO_2C$—, benzyloxycarbonyl, benzyloxycarbonylmethyl,

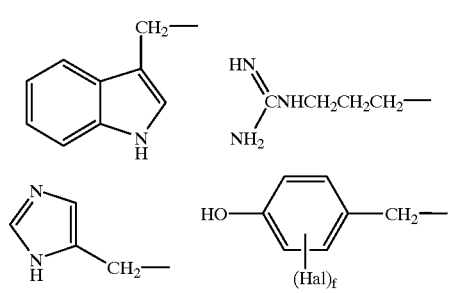

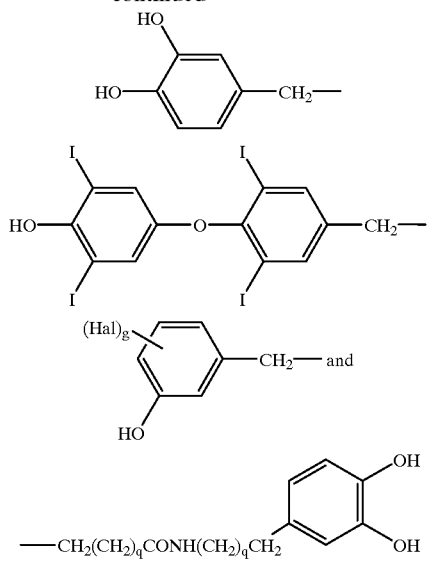

wherein Hal is as defined above and f is 0, 1 or 2, g is 0, 1 or 2, and each q is independently 0 or 1.

The group of structure

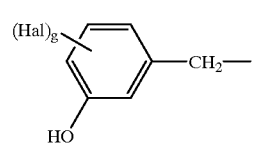

may in particular for example be a fluoride substituted structure of formula

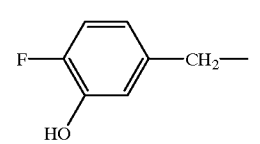

Similarly, the group of structure

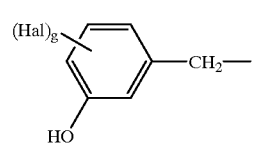

may in particular for example be a fluoride substituted structure of formula

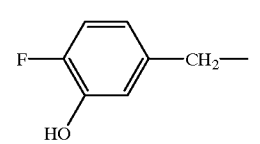

As mentioned, when a compound of formula I comprises a carboxylic acid group the polyhydroxy compounds may be any pharmaceutically acceptable salt thereof and when a compound of formula I comprises an amino group the polyhydroxy compounds may be any pharmaceutically acceptable ammonium salt thereof.

The present invention provides, where appropriate, salts (e.g. derived from appropriate bases or acids) which include but are not limited to alkali metal (e.g., sodium, potassium, cesium, etc.) salts, alkaline earth metal (e.g., magnesium) salts, and ammonium salts such as acid addition salts of amines (e.g. ammonium chloride salts) as well as quaternary ammonium salts of for example N—(R")$_4^+$ type wherein R" is an organic residue.

The pharmaceutically acceptable salts of the compounds of this invention include those derived from pharmaceutically acceptable inorganic and organic acids and bases. Examples of such acid salts include: acetate adipate, alginate aspartate benzoate, benzenesulfonate, bisulfate, butyrate, citrate, camphorate, camphorsulfonate, cyclopentanepropionate, digluconate, dodecylhydrogensulfate, dodecylsulfate, ethanesulfonate, formate, fumarate, glucoheptanoate, glycerophosphate, glycollate, hemisulfate, heptanoate, hexanoate, hydrochloride, hydrobromide, hydroiodide, 2-hydroxyethanesulfonate, lactate, maleate, malonate, methanesulfonate, 2-naphthylsulfonate, nicotinate, nitrate, oxalate, pamoate, pectinate, perchlorate, persulfate, 3-phenylpropionate, phosphate, picrate, pivalate, propionate, salicylate, succinate, sulfate, tartrate, thiocyanate, tosylate, and undecanoate.

This invention also envisions the quaternization of any basic nitrogen containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodide; and arylalkyl halides including benzyl and phenethyl bromides. Water or oil-soluble or dispersible products may be obtained by such quaternization.

This invention also envisions the presence of an ester group(s) such as for example on the acidic end of an appropriate amino acid fragment(s), such as glutamic acid and aspartic acid as having some anti-integrase activity as such as acting as pro-drugs, i.e. capable of hydrolysis of the ester moiety to liberate in the systemic circulation the acid, also possessing anti-integrase activity. For example, the ether oxygen of an ester compound may be attached or linked to benzyl, a lower (branched or straight) alkyl (e.g. $C_1$–$C_6$ alkyl) such as methyl, a lower cycloalkyl (e.g. $C_3$–$C_7$ cycloalkyl) such as cyclohexyl, and the like. Alternatively, an ester(s) may be derived from a carboxylic acid(s) and one or more hydroxyl groups, such as for example an hydroxyl group on a phenyl ring. A carboxylic acid may, for example, comprise an acyl group having from 2 to 8 carbon atoms; the acyl group may for example comprise lower alkyl of 1 to 6 carbon atoms, lower cycloalkyl of from 3 to 7 carbon atoms, etc..

In addition, this invention further envisions the presence of structures having an amide functionality such as, for example, on the carboxylic end located on the side chain of such acids. These amides, such as simple primary, secondary or tertiary amides, possess activity of their own. In addition, it is possible to couple such acids with dopamine to yield compounds of interest. The amino moiety of an amide compound may for example be —NH$_2$, —NH($C_1$–$C_6$ alkyl), or —N($C_1$–$C_6$ alkyl)$_2$, a pyrrolidine residue, a piperidine residue, a morpholine residue and the like In any event, it is also to be understood that the present invention relates to any other compound having a structure such that, upon administration to a recipient, it is capable of providing (directly or indirectly) a compound of this invention or an antivirally active metabolite or residue thereof. Thus the compounds of this invention may be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The present invention in particular provides a dopamine derivative selected from the group consisting of a compound of formula Ia

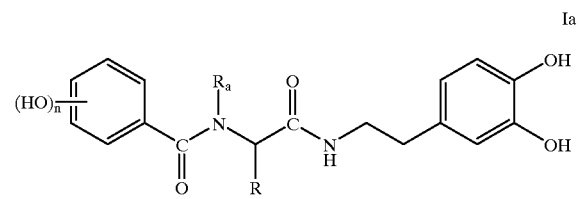

and when a compound of formula Ia comprises a carboxylic acid group pharmaceutically acceptable salts thereof and when a compound of formula Ia comprises an amino group pharmaceutically acceptable ammonium salts thereof, wherein n, $R_a$ and R are as defined above.

The present invention also provides a dopamine derivative selected from the group consisting of a compound of formula Ib

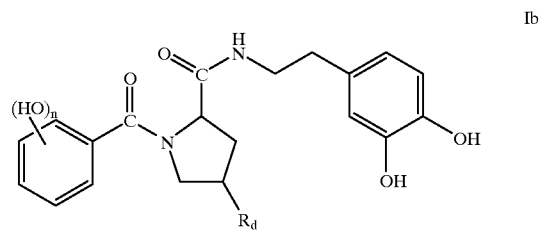

wherein n is as defined above (e.g. n may in particular be 1 or 2), and $R_d$ is selected from the group consisting of H and OH.

The present invention further relates to dipeptide derivatives i.e. to compounds of formula I defined above wherein k is 1. The present invention in particular provides an hydroxylphenyl derivative wherein for the compound of general formula I above, W represents a group of formula

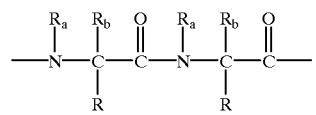

wherein n is as defined above (e.g. n may in particular be 1 or 2), p is as defined above (p may in particular be 0), each $R_a$ is independently as defined above, each $R_b$ is independently as defined above, and each R is independently as defined above; more particularly, for example, for each R, f may be 0 or 1 and g may be 0 or 1.

The compounds of this invention contain one or more asymmetric carbon atoms and thus may occur as racemates and racemic mixtures, single enantiomer, diastereomeric mixtures and individual diastereoisomers. All such isomeric forms of these compounds are expressly included in the present invention. Each stereogenic carbon may be of the R or S configuration.

The amino acid residues may, for example, in any event, be of L, D or DL form, preferably of L form; thus for example the amino acid residue (i.e. W) may be a L-α-amino residue, a D-α-amino residue, or a DL-α-amino residue.

Accordingly, the present invention further provides a dopamine derivative selected from the group consisting of a compound of formula Ic

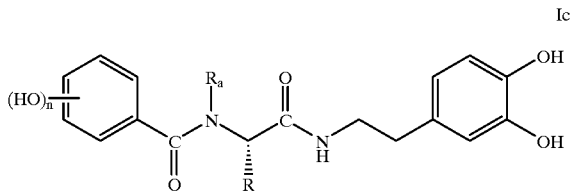

and when a compound of formula Ic comprises a carboxylic acid group pharmaceutically acceptable salts thereof and when a compound of formula Ic comprises an amino group pharmaceutically acceptable ammonium salts thereof, wherein n is 1, or 2, $R_a$ and R are as defined above (e.g. f and g may be 0 or 1 and the respective group Hal thereof may be fluorine (F)).

The present invention furthermore provides a dopamine derivative selected from the group consisting of a compound of formula Id

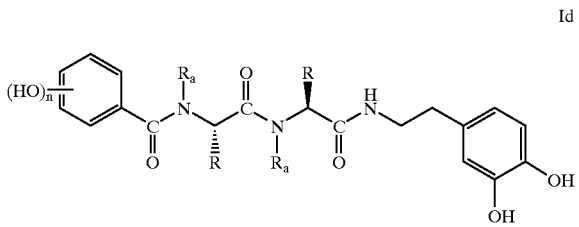

and when a compound of formula Id comprises a carboxylic acid group pharmaceutically acceptable salts thereof and when a compound of formula Id comprises an amino group pharmaceutically acceptable ammonium salts thereof, wherein n is 1, or 2, each $R_a$ is independently as defined above, and each R is independently as defined above; more particularly, for example, for each R, f may be 0 or 1 and g may be 0 or 1.

The compounds of the present invention including where applicable their pharmaceutically acceptable derivatives have an affinity for integrase, in particular, HIV integrase. Therefore, these compounds are useful as inhibitors of such integrase, i.e. they are in particular useful as HIV integrase inhibitors. These compounds can be used alone or in combination with other therapeutic or prophylactic agents, such as antivirals, antibiotics, immunomodulators or vaccines, for the treatment or prophylaxis of viral infection.

According to the present invention, the compounds of this invention are capable of inhibiting HIV viral replication in human CD4+ T-cells, by inhibiting the ability of HIV integrase to integrate the double stranded DNA into host genomic DNA for further virus replication by the host cell machinery (Sakai H., J. Virol. Vol. 67 p. 1169–1174 (1993)). These novel compounds can thus serve to reduce the production of infectious virions from acutely infected cells, and can inhibit the initial or further infection of host cells.

Accordingly, these compounds are useful as therapeutic and prophylactic agents to treat or prevent infection by HIV-1 and related viruses, which may result in asymptomatic HIV-1 infection, AIDS-related complex (ARC), acquired immunodeficiency syndrome (AIDS), AIDS-related dementia, or similar diseases of the immune system.

Thus the present invention also provides a pharmaceutical composition comprising a pharmaceutically acceptable carrier and a pharmaceutically effective amount of at least one hydroxyphenyl derivative as defined above. The pharmaceutical compositions may be used to inhibit integrase, including HIV integrase, thus providing protection against HIV infection.

The expression "pharmaceutically effective amount" is to be understood herein as referring to an amount effective in treating HIV infection in a patient. The term prophylactically effective amount refers to an amount effective in preventing HIV infection in a patient. As used herein, the term patient refers to a mammal, including a human. The expressions "pharmaceutically acceptable carrier" (or adjuvant) and "physiologically acceptable vehicle" are to be understood as referring to a non-toxic carrier or adjuvant that may be administered to a patient, together with a compound of this invention, and which does not destroy the pharmacological activity thereof. These factors will be discussed in more detail below.

The compounds of this invention may be readily prepared using conventional techniques from commercially available and cheap starting materials. The relative ease of synthesis of the products described in this invention represents a marked advantage for the large scale preparation of these compounds. In general, the derivatives of the present invention may be readily obtained from amino acids through sequences recognized by those knowledgeable in the art as straightforward, requiring readily available reagents and easy techniques. Using standard techniques, amino acids may be transformed to the desired HIV integrase inhibitors according to approaches as shown in Scheme 1, Scheme 2 and Scheme 3 which are discussed below. The preparation of dipeptide derivatives may be accomplished by solid phase peptide synthesis; this type of process is generically illustrated in scheme 4 below (see example 42 below).

Scheme 1 illustrates example steps for the preparation of a derivative in accordance with the present invention:

Note:
  a) For scheme 1, PG and PG' may be any suitable (known) removable protecting group for respectively protecting the amine functional group and the carboxylic acid functional group(s). PG may, for example, be Boc i.e. tert-butoxycarbonyl and PG' may, for example, be tert-Butyl, 2,6-Cl$_2$Bzl or Bzl, i.e. a functional group of the following formula

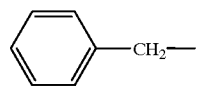

b) For scheme 1 R$_1$ may, for example, be CH$_3$—, BzlOOCCH$_2$CH$_2$—, H$_2$NC(O)CH$_2$CH$_2$—; R$_{1a}$ may, for example, be CH$_3$—, HOOCCH$_2$CH$_2$—, H$_2$NC(O)CH$_2$CH$_2$—

Step 1)

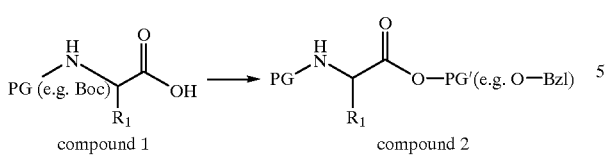

Step 2)

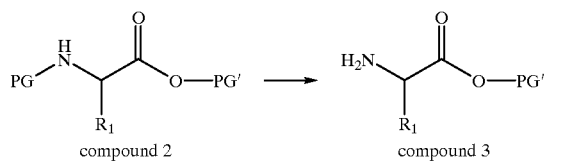

Step 3)

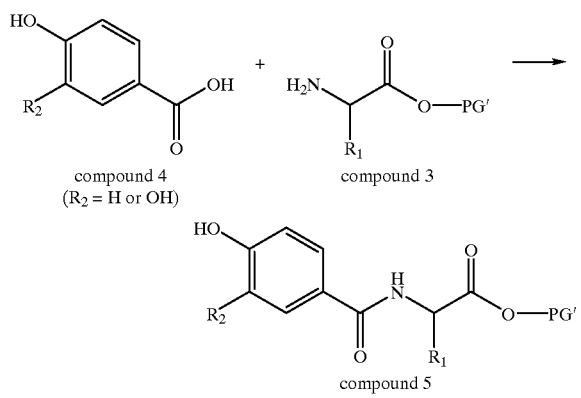

Step 4)

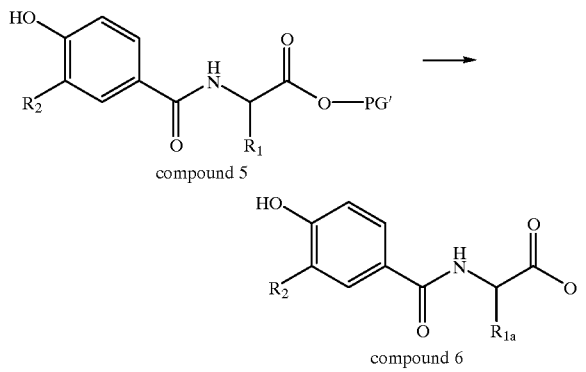

Step 5)

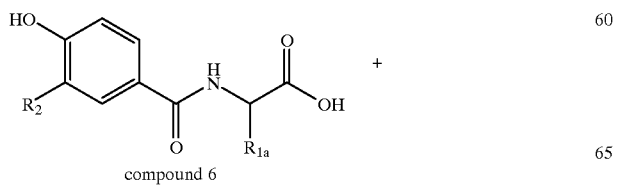

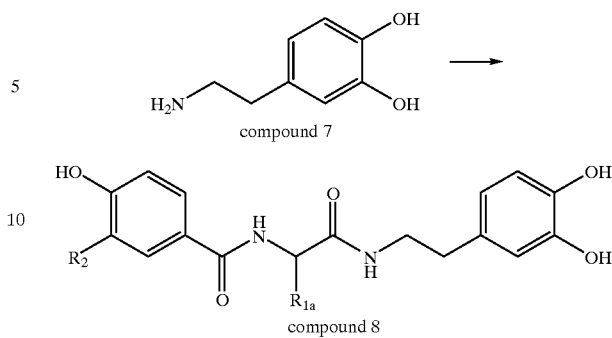

In accordance with Scheme 1, illustrated above, different pharmacophores may be attached to the amino acid via the N-terminal. Thus, for step 1 compound 1 is treated so as to protect the carboxylic acid functional group by means of a suitable protecting group PG'; for example compound 1 may be a Boc-amino acid which is benzylated with benzyl bromide to yield compound 2 in the form of a benzyl ester using cesium carbonate in DMF according to the method of S.-S. Wang et al (J. Org. Chem. vol 49 p. 1286 (1977)). For step 2 the amino protecting group PG is removed to provide compound 3 having a free amino functional group; for example the removal of the Boc group from compound 3 may be carried out by stirring in a mixture of TFA and methylene chloride (1:1 (v/v)). For step 3 the amino compound 3 is then coupled with an hydroxylated benzoic acid (compound 4) with EDC and HOBT in DMF providing the desired coupled product compound 5. For step 4 compound 5 is treated to remove the protecting group PG' to yield compound 6 having a free carboxylic acid group; for example the benzyl protecting group PG' may be removed by hydrogenolysis using 10% Pd/C as catalyst to yield compound 6 having a free carboxylic acid group. Finally for step 5 compound 6 is coupled with dopamine (compound 7) to provide the desired derivative, namely compound 8.

Scheme 2 (which is divided below into scheme 2a and scheme 2b) illustrates example steps for an alternate method for the preparation of a derivative in accordance with the present invention:

Note:
a) For scheme 2a, PG, as mentioned above, may be any suitable (known) removable protecting group for protecting the amine functional group. PG may, for example, be Boc i.e. tert-butoxycarbonyl b) For scheme 2a, $R_3$ may, for example, be $(CH_3)_2CHCH_2—$, $CH_3SCH_2CH_2—$, or a functional group of the following formula

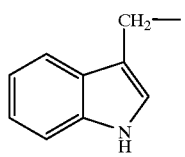

Scheme 2a:
Step 1
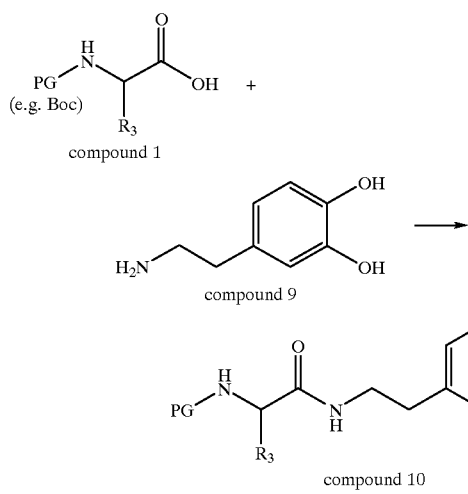
Step 2:
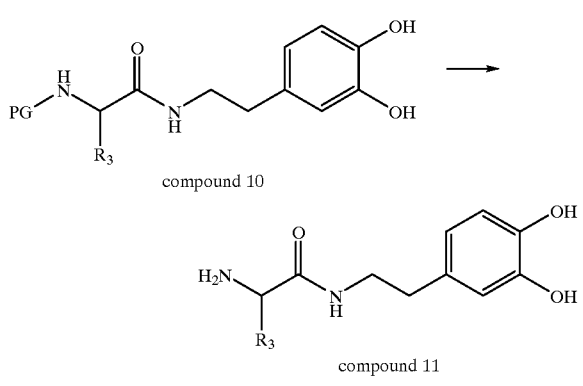
Step 3:
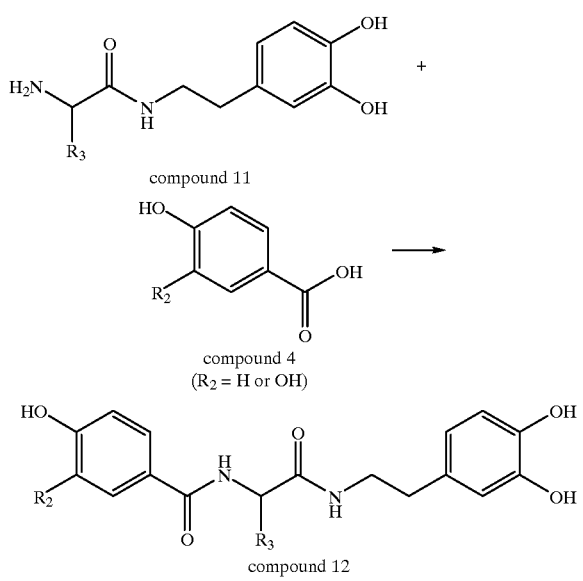
Scheme 2b:
Step 1
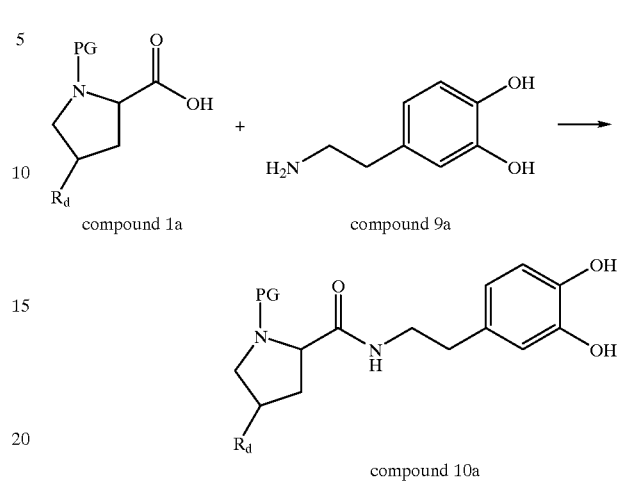
Step 2:
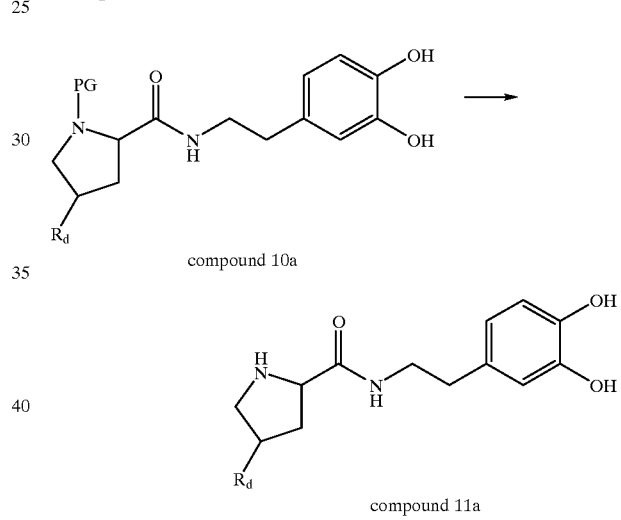
Step 3:
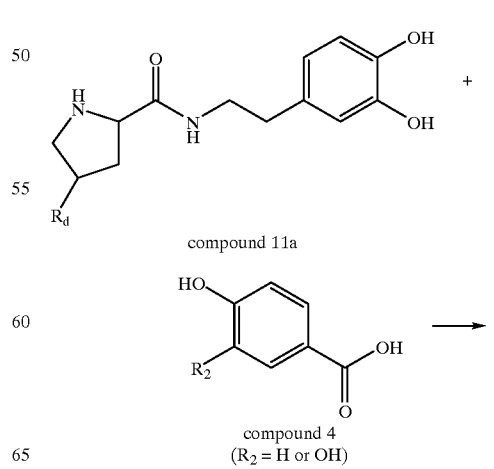

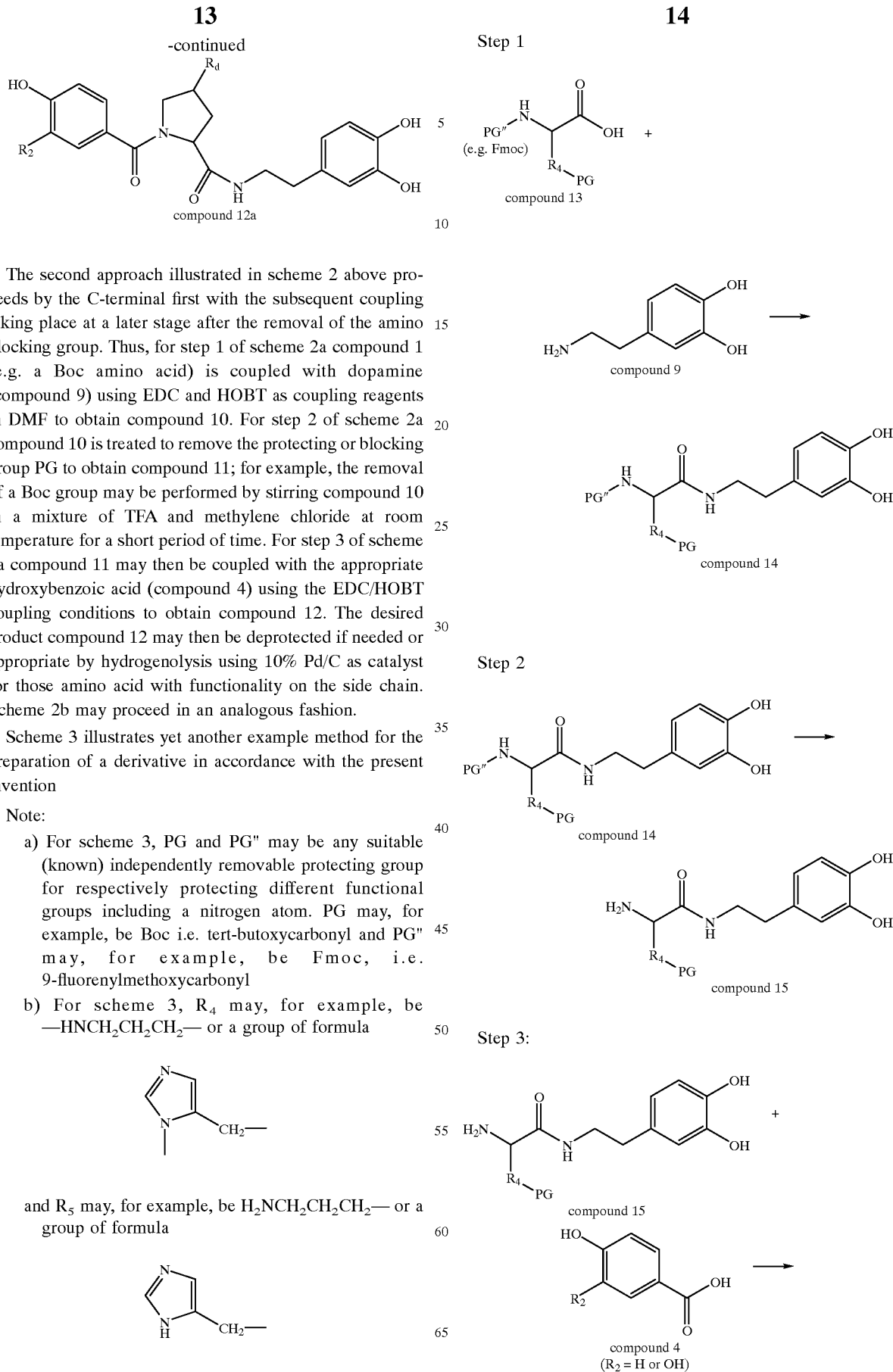

The second approach illustrated in scheme 2 above proceeds by the C-terminal first with the subsequent coupling taking place at a later stage after the removal of the amino blocking group. Thus, for step 1 of scheme 2a compound 1 (e.g. a Boc amino acid) is coupled with dopamine (compound 9) using EDC and HOBT as coupling reagents in DMF to obtain compound 10. For step 2 of scheme 2a compound 10 is treated to remove the protecting or blocking group PG to obtain compound 11; for example, the removal of a Boc group may be performed by stirring compound 10 in a mixture of TFA and methylene chloride at room temperature for a short period of time. For step 3 of scheme 2a compound 11 may then be coupled with the appropriate hydroxybenzoic acid (compound 4) using the EDC/HOBT coupling conditions to obtain compound 12. The desired product compound 12 may then be deprotected if needed or appropriate by hydrogenolysis using 10% Pd/C as catalyst for those amino acid with functionality on the side chain. Scheme 2b may proceed in an analogous fashion.

Scheme 3 illustrates yet another example method for the preparation of a derivative in accordance with the present invention Note:
  a) For scheme 3, PG and PG" may be any suitable (known) independently removable protecting group for respectively protecting different functional groups including a nitrogen atom. PG may, for example, be Boc i.e. tert-butoxycarbonyl and PG" may, for example, be Fmoc, i.e. 9-fluorenylmethoxycarbonyl
  b) For scheme 3, $R_4$ may, for example, be —HNCH$_2$CH$_2$CH$_2$— or a group of formula and $R_5$ may, for example, be H$_2$NCH$_2$CH$_2$CH$_2$— or a group of formula -continued

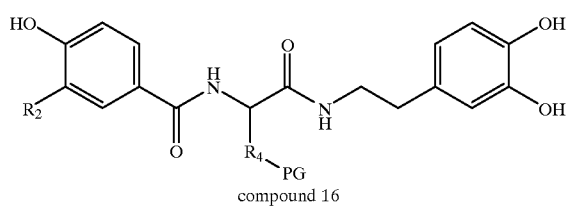
compound 16

Step 4:

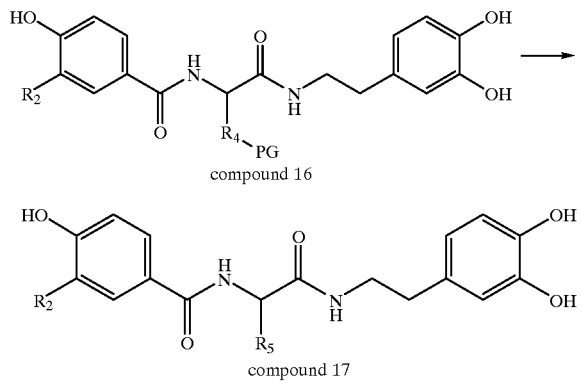
compound 16 compound 17

In scheme 3 illustrated above the starting amino acid (compound 13) is provided with a pair of independently removable protecting groups PG and PG"; the amino group may have a protecting group (PG") such as Fmoc for example. On the other hand if the group $R_4$ includes a primary or secondary amino component a protecting group PG may likewise be attached to the nitrogen atom of such an amino component; PG may, for example, be Boc or tert-butoxycarbonyl. Thus, for step 1 of scheme 3 compound 13 is coupled with dopamine (compound 9) using EDC and HOBT as coupling reagents in DMF to obtain compound 14. For step 2 compound 14 is treated to remove the protecting or blocking group PG" to obtain compound 15. For step 3 compound 15 may then be coupled with the appropriate hydroxybenzoic acid (compound 4) using the EDC/HOBT coupling conditions to obtain compound 16. For step 4 compound 15 is treated to remove the protecting group PG to yield compound 17.

Scheme 4 illustrates in a generic fashion an example method for the preparation of a dipeptide derivative in accordance with the present invention (see example 42 below for a more specific description of a process for making a dipeptide derivative):

Step 1

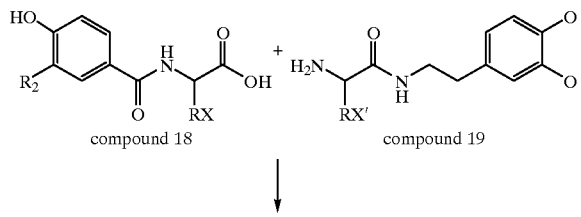
compound 18     compound 19

-continued

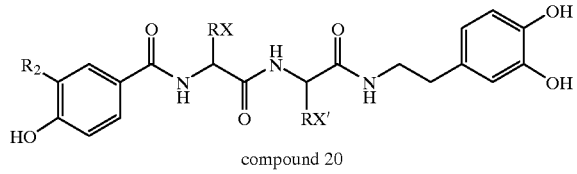
compound 20

(RX and RX' independently have the values set forth for R herein).

The compounds listed in Table 1 were prepared by following Scheme 1 or Scheme 2 (see examples below); the number(s) in brackets after each root amino acid name is the numer(s) of an example(s) below. Their activities are also listed in the same table demonstrating their potential usefulness.

TABLE 1

Anti-integrase activity ($IC_{50}$) of amino acid derivatives in accordance with formula Ic above

| | Anti-integrase activity ($IC_{50}$) | |
|---|---|---|
| Root Amino acid (i.e. W for formula I is the fragment thereof) | 4-hydroxy derivative μM | 3,4-dihydroxy derivative μM |
| Glycine (ex. 15) | | 100 |
| L-Glutamic (ex. 21 & 22 - step B) | 64 | 11 |
| L-Glutamic-4-O-benzyl (ex. 23) | | 26 |
| L-Tyrosine (ex. 11 & 12) | 88 | 8 |
| L-Tryptophan (ex. 29 & 30) | 245 | 17 |
| L-Proline (ex. 27 & 28) | >200 | 80 |
| L-Leucine (ex. 25 & 26) | >200 | 45 |
| L-Phenylalanine (ex. 13 & 14) | >200 | 45 |
| L-Serine (ex. 18) | | 100 |
| L-Methionine (ex. 31) | | 100 |
| L-Dopa (ex. 16) | | 8 |
| D-Tyrosine (ex. 10) | | 67 |
| D-Tyrosine-O-benzyl (ex. 10 - step D) | | 42 |
| L-Alanine (ex. 19 & 20) | 160 | 71 |
| L-Histidine (ex. 33) | | 0.1 |
| DL-3-Fluoro-Tyrosine (ex. 48) | | 1.4 |
| L-Glutamine benzyl ester (ex. 49) | | 2.2 |
| DL-m-Tyrosine (ex. 50) | | 1.3 |

Dipeptide derivatives were also prepared and are listed in Table 2; the number(s) in Table 2 with respect to each product structure name therein indicated a number of an example.

TABLE 2

Anti-integrase activity ($IC_{50}$) of dipeptide derivatives of I

| Product | Xa | Y | Anti-integrase activity ($IC_{50}$) | Ex. No. |
|---|---|---|---|---|
| Xa-Tyr-Tyr-Y | 3,4-dihydroxybenzoyl | OH | 177 | 36 |
| Xa-Tyr-Tyr-Y | 3,4-dihydroxybenzoyl | 3,4-dihydroxy-phenethylamino | 17 | 51 |
| Xa-Gly-Tyr-Y | 3,4-dihydroxybenzoyl | OH | >200 | 39 |
| Xa-Tyr-Asp(OBn)-Y | 3,4-dihydroxybenzoyl | 3,4-dihydroxy-phenethylamino | 20 | 41 |
| Xa-Tyr-Gly-Y | 3,4-dihydroxybenzoyl | OH | >200 | 37 |

As can be appreciated by the skilled artisan, the above synthetic schemes are not intended to comprise a comprehensive list of all means by which the compounds described and claimed in this application may be synthesized. Further methods will be evident to those of ordinary skill in the art.

For the purposes of Table 1 (and Table 2) the HIV-1 integrase inhibition assay was carried out following a known procedure (Burke, Jr. T. R. et al., J. Med. Chem. 38, 4171–4178 (1995)). A suitable radiolabeled duplex substrate corresponding to the U5 end of the HIV LTR was used.

The novel compounds of the present invention are excellent ligands for integrase, particularly HIV-1, and most likely HIV-2 and HTLV-1 integrase. Accordingly, these compounds are capable of targeting and inhibiting an early stage event in the replication, i.e. the integration of viral DNA into the human genome, thus preventing the replication of the virus.

In addition to their use in the prophylaxis or treatment of HIV infection, the compounds according to this invention may also be used as inhibitory or interruptive agents for other viruses which depend on integrases, similar to HIV integrases, for obligatory events in their life cycle. Such compounds inhibit the viral replication cycle by inhibiting integrase. Because integrase is essential for the production of mature virions, inhibition of that process effectively blocks the spread of virus by inhibiting the production and reproduction of infectious virions, particularly from acutely infected cells. The compounds of this invention advantageously inhibit enzymatic activity of integrase and inhibit the ability of integrase to catalyze the integration of the virus into the genome of human cells.

The compounds of this invention may be employed in a conventional manner for the treatment or prevention of infection by HIV and other viruses which depend on integrases for obligatory events in their life cycle. Such methods of treatment, their dosage levels and requirements may be selected by those of ordinary skill in the art from available methods and techniques. For example a compound of this invention may be combined with a pharmaceutically acceptable adjuvant for administration to a virally infected patient in a pharmaceutically acceptable manner and in an amount effective to lessen the severity of the viral infection. Also, a compound of this invention may be combined with pharmaceutically acceptable adjuvants conventionally employed in vaccines and administered in prophylactically effective amounts to protect individuals over an extended period of time against viral infections, such as HIV infection. As such, the novel integrase inhibitors of this invention can be administered as agents for treating or preventing viral infections, including HIV infection, in a mammal. The compounds of this invention may be administered to a healthy or HIV-infected patient either as a single agent or in combination with other antiviral agents which interfere with the replication cycle of HIV. By administering the compounds of this invention with other antiviral agents which target different events in the viral replication cycle, the therapeutic effect of these compounds is potentiated. For instance, the co-administered antiviral agent can be one which targets early events in the life cycle of the virus, such as cell entry, reverse transcription and viral DNA integration into cellular DNA. Antiviral agents targeting such early life cycle events include, didanosine (ddI), zalcitabine (ddC), stavudine (d4T), zidovudine (AZT), polysulfated polysaccharides, sT4 (soluble CD4)—which blocks attachment or adsorption of the virus to host cells—and other compounds which block binding of virus to CD4 receptors on CD4-bearing T-lymphocytes. Other retroviral reverse transcriptase inhibitors, such as derivatives of AZT, may also be co-administered with the compounds of this invention to provide therapeutic treatment for substantially reducing or eliminating viral infectivity and the symptoms associated therewith. Examples of other antiviral agents include ganciclovir, dideoxycytidine, trisodium phosphonoformiate, eflornithine, ribavirin, acyclovir, alpha interferon and trimenotrexate. Additionally, non-ribonucleoside inhibitors of reverse transcriptase, such as TIBO or nevirapine, may be used to potentiate the effect of the compounds of this invention, as may viral uncoating inhibitors, inhibitors of trans-activating proteins such as tat or rev, or inhibitors of the viral protease. These compounds may also be co-administered with other inhibitors of HIV integrase.

Combination therapies according to this invention exert a synergistic effect in inhibiting HIV replication because each component agent of the combination acts on a different site of HIV replication. The use of such combinations also advantageously reduces the dosage of a given conventional anti-retroviral agent that would be required for a desired therapeutic or prophylactic effect as compared to when that agent is administered as a monotherapy. These combinations may reduce or eliminate the side effects of conventional single anti-retroviral agent therapies while not interfering with the anti-retroviral activity of those agents. These combinations reduce potential of resistance to single agent therapies, while minimizing any associated toxicity. These combinations may also increase the efficacy of the conventional agent without increasing the associated toxicity. Preferred combination therapies include the administration of a compound of this invention with AZT, 3TC, ddI, ddC or d4T.

Alternatively, the compounds of this invention may also be co-administered with other HIV protease inhibitors such as Ro 31-8959 (Roche), L-735,524 (Merck), XM 323 (Dupont Merck) and A-80,987 (Abbott) to increase the effect of therapy or prophylaxis against various viral mutants or members of other HIV quasi species.

We prefer administering the compounds of this invention as single agents or in combination with retroviral reverse transcriptase inhibitors, such as derivatives of AZT or HIV aspartyl protease inhibitors. We believe that the co-administration of the compounds of this invention with retroviral reverse transcriptase inhibitors or HIV aspartyl protease inhibitors may exert a substantial synergistic effect, thereby preventing, substantially reducing, or completely eliminating viral infectivity and its associated symptoms.

The compounds of this invention can also be administered in combination with immunomodulators (e.g., bropirimine, anti-human alpha interferon antibody, IL-2, GM-CSF, methionine enkephalin, interferon alpha, diethyldithiocarbante, tumor necrosis factor, naltrexone and rEPO); antibiotics (e.g., pentamidine isethionate) or vaccines to prevent or combat infection and disease associated with HIV infection, such as AIDS and ARC.

When the compounds of this invention are administered in combination therapies with other agents, they may be administered sequentially or concurrently to the patient. Alternatively, pharmaceutical or prophylactic compositions according to this invention may be comprised of a combination of an integrase inhibitor of this invention and another therapeutic or prophylactic agent.

Although this invention focuses on the use of the compounds disclosed herein for preventing and treating HIV infection, the compounds of this invention can also be used as inhibitory agents for other viruses that depend on similar integrases for obligatory events in their life cycle. These viruses include, but are not limited to, other diseases caused by retroviruses, such as simian immunodeficiency viruses, HTLV-I and HTLV-II.

Pharmaceutical compositions of this invention comprise any of the compounds of the present invention, and pharmaceutically acceptable salts thereof, with any pharmaceutically acceptable carrier, adjuvant or vehicle. Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethyleneglycol, sodium carboxymethylcellulose, polyacrylates, waxes, polyethylene-polyoxypropylene-block polymers, polyethylene glycol and wool fat.

The pharmaceutical compositions of this invention may be administered orally, parenterally by inhalation spray, topically, rectally, nasally, buccally, vaginally or via an implanted reservoir. We prefer oral administration or administration by injection. The pharmaceutical compositions of this invention may contain any conventional non-toxic pharmaceutically acceptable carriers, adjuvants or vehicles. The term "parenteral" as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solutions. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv. or a similar alcohol.

The pharmaceutical compositions of this invention may be orally administered in any orally acceptable dosage form including, but not limited to, capsules, tablets, and aqueous suspension and solutions. In the case of tablets for oral and carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax, and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical compositions can be formulated with a suitable lotion or cream containing the active compound suspended or dissolved in a carrier. Suitable carriers include, but are not limited to mineral oil, sorbitan monostearate, polysorbate 60, cetyl esters wax cetearyl alcohol, 2-octyldodecanol, benzyl alcohol and water. The pharmaceutical compositions of this invention may also be topically applied to the lower intestinal tract by rectal suppository formulation or in a suitable neat formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline employing benzyl alcohol or other suitable preservatives, absorption promoters to enhance bioavailability, fluorocarbons, and/or other solubilizing or dispersing agents known in the art.

Dosage levels of between about 0.01 and about 25 mg/kg body weight per day, preferably between about 0.5 and about 25 mg/kg body weight per day of the active ingredient compound are useful in the prevention and treatment of viral infection, including HIV infection. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the patient treated and the particular mode of administration. A typical preparation will contain from about 5% to about 75% active compound (w/w). Preferably, such preparations contain from about 20% to about 50% active compound.

Upon improvement of a patient's condition, a maintenance dose of a compound, composition or combination of this invention may be administered if necessary. Subsequently, the dosage or frequency of administration, or both, may be reduced, as a function of the symptoms, to a level at which the improved condition is retained. When the symptoms have been alleviated to the desired level, treatment should cease, at least in principle. Patients may, however, require intermittent treatment on a long-term basis, upon any recurrence of disease symptoms, especially for AIDS.

As the skilled artisan will appreciate, lower or higher doses than those recited above may be required. Specific dosage and treatment regimen for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician.

The compounds of this invention are also useful as commercial reagents which effectively bind to integrases, particularly HIV integrase. As commercial reagent, the compounds of this invention, and their derivatives, may be used to block integration of a target DNA molecule by integrase, or may be derivatized to bind to a stable resin as a tethered substrate for affinity chromatography applications. These and other uses which characterize commercial integrase inhibitors will be evident to those of ordinary skill in the art.

DETAILED DESCRIPTION OF THE INVENTION

In order that the invention herein described may be more fully understood, the following detailed description is set forth. In the description, the following abbreviations are used:

| Designation | Reagent or Fragment |
| --- | --- |
| Et | ethyl |
| Trityl | triphenylmethyl |
| Ala | DL, D-or L-alanine |
| Asn | DL, D-or L-asparagine |
| Cys | DL, D-or L-cysteine |
| Gly | glycine |
| Gln | DL, D-or L-glutamine |
| His | DL, D-or L-histidine |
| Ile | DL, D-or L-isoleucine |
| Leu | DL, D-or L-leucine |
| Met | DL, D-or L-methionine |
| Phe | DL, D-or L-phenylalanine |
| Pro | DL, D-or L-proline |
| Ser | DL, D-or L-serine |
| Thr | DL, D-or L-threonine |
| Trp | DL, D-or L-tryptophan |
| Val | DL, D-or L-valine |
| Boc | tert-butoxycarbonyl |
| EDC | 1-(3-dimethylaminopropyl)-3-ethylcarbodiimide |
| BOP | benzotriazol-1-yloxytris(dimethylamino)phosphonium hexafluorophosphate |
| TFA | trifluoroacetic acid |
| EtOAC | ethyl acetate |
| DMF | dimethylformamide |
| AZT | zidovudine |
| IL-2 | interleukin-2 |
| rEPO | recombinant erythropoietin |
| EtOH | ethyl alcohol |
| MeOH | methyl alcohol |
| THF | tetrahydrofuran |
| $CH_2Cl_2$ | dichloromethane |
| $Cl_2$-Bzl | 2,6-dichlorobenzyl |
| tert-Bu | tert-butyl |
| Bzl | benzyl |
| NMP | N-methylpyrrolidone |
| $CHCl_3$ | chloroform |

Combinations of substituents and variables envisioned by this invention are only those that result in the formation of stable compounds.

The term stable, as used herein, refers to compounds which possess stability sufficient to allow manufacture and administration to a mammal by methods known in the art. Typically, such compounds are stable at a temperature of 40° C. or less, in the absence of moisture or other chemically reactive conditions, for at least a week.

EXAMPLES

In order that this invention be more fully understood, the following examples are set forth. These examples are for the purpose of illustration only and are not to be construed as limiting the scope of the invention in any way.

Materials and Methods

Analytical thin layer chromatography (TLC) was carried out with 0.25 mm silica gel E. Merck 60 $F_{254}$ plates and eluted with the indicated solvent systems. Preparative chromatography was performed by flash chromatography, using silica gel 60 (EM Science) with the indicated solvent systems and a positive nitrogen pressure to allow proper rate of elution. Detection of the compounds was carried out by exposing eluted plates (analytical or preparative) to UV light and/or treating analytical plates with a 2% solution of p-anisaldehyde in ethanol containing 3% sulfuric acid and 1% acetic acid followed by heating.

Unless otherwise indicated, all starting materials were purchased from a commercial source such as Aldrich Co. or Sigma Co.

Nuclear magnetic resonance (NMR) spectra were recorded on a Bruker AMX 500 equipped with a reversed or QNP probe. Samples were dissolved in deuterochloroform ($CDCl_3$), deuteroacetone (acetone-$d_6$) or deuterodimethylsulfoxide (DMSO-$d_6$) for data acquisition using tetramethylsilane as internal standard. Chemical shifts are expressed in parts per million (ppm), the coupling constants (J) are expressed in hertz (Hz) whereas multiplicities are denoted as s for singlet, d for doublet, dd for doublet of doublets, t for triplet, q for quartet, m for multiplet, and br s for broad singlet.

GENERAL PROCEDURES

Example 1

Preparation of N-(tert-butoxycarbonyl)amino Acids

To a solution of amino acid (1 eq.) in water and dioxane were added at room temperature triethylamine (1.3–1.5 eq.) and Boc-ON (1.1 eq.) or di-tert-butyl-dicarbonate (2 eq.). The mixture was stirred at room temperature under argon for 3 to 5 h. The solution was diluted with water and extracted by ether at least six times. The aqueous layer was acidified to pH ~2.5 with cold 1N HCl to yield an oily layer. The mixture was extracted three times with methylene chloride. The combined organic extracts were washed with brine and dried over magnesium sulfate. After filtration, the filtrate was evaporated using a bath set at 30° C. The residue was found to be of sufficient purity for the next reaction step.

Example 2

Benzylation of N-Boc Amino Acid

Three different solvent systems were used to achieve benzylation of acids or hydroxyl groups.

a) Methanol/Water Followed by DMF Method

To a N-Boc amino acid (1 eq.) in methanol was added cesium carbonate (1.4–2.0 eq.) as a 20% solution in water, and then the solution was evaporated to dryness. The residue was dissolved in dimethylformamide (DMF) and benzyl bromide (1–1.5 eq.) was added. The mixture was stirred at room temperature under argon overnight. The mixture was diluted with water and the organic layer was extracted with ethyl acetate. The combined organic phases were washed with brine and dried over magnesium sulfate. The solids were filtered off and solvent was evaporated under vacuum yielding a residue that was purified by silica gel chromatography using 20% ethyl acetate in hexane.

b) Dimethylformamide Method

To a N-Boc amino acid (1 eq.) in dimethylformamide (DMF) were added cesium carbonate (1.4–2.0 eq.) and benzyl bromide (1.1–1.5 eq.). The reaction mixture was stirred at room temperature overnight under argon. A work-up and purification as previously described in example 2a yielded the desired product.

c) Acetone Method

To a N-Boc amino acid (1 eq.) in acetone were added potassium carbonate (1.4–2.0 eq.) and benzylbromide (1.1–1.5 eq.). The reaction mixture was stirred at room temperature for a period of 3–5 h under argon. Work-up and purification as carried out in the previous example 2a afforded the desired product.

Example 3

Removal of the N-tert-butoxycarbonyl (Boc) Group

A solution of N-tert-butoxycarbonyl amino acid (1 eq.) in a 1: 1 mixture of trifluoroacetic acid (TFA) (10 eq.) and methylene chloride ($CH_2Cl_2$) was stirred at room temperature for 15–30 min. The solvent and excess acid were removed under vacuum to yield the desired product that was used without further purification.

Example 4

Coupling Reaction of Hydroxylated Benzoic Acid With the NH Part of an Amino Acid To a mixture of 3-hydroxy- or 3,4-dihydroxybenzoic acid (1.5 eq.), hydroxybenzotriazole hydrate (HOBT) (1.6 eq.), and 1-(3-dimethylaminopropyl)-3-ethylcarbodiimide (EDC) (1.6 eq.) in DMF was added a solution of product from example 3 (1 eq.) and triethylamine or diisopropylethylamine (1 eq.) in DMF. The mixture was stirred at room temperature under argon for either 6 h or overnight, monitoring the reaction by TLC. The reaction mixture was quenched by water and extracted three times with ethyl acetate. The organic phases were combined and washed with brine. After drying over magnesium sulfate, the solution was filtered and the solvent was evaporated under vacuum. The residue was purified by silica gel chromatography, eluting as indicated in each procedure.

Example 5

Cleavage of Benzyl Esters or Benzyl Ethers

The benzyl ester or benzyl ether of an amino acid derivative dissolved in methanol was hydrogenated over 10% Pd—C (less than 10% by weight of the weight the amino acid benzyl ester or ether) under 1 atmosphere of $H_2$ for 1–2 h. The catalyst was filtered off and the filtrate was evaporated under vacuum to yield the desired product.

Example 6

Coupling Reaction of Dopamine With the COOH of a Substituted Amino Acid

To a solution of substituted carboxylic acid (1 eq.) prepared as in example 5, HOBT (1.5 eq.) and EDC (1.5 eq.) in DMF at 0° C. was added a solution of dopamine hydrochloride (2 eq.) and triethylamine or diisopropylethylamine (2 eq.) in DMF. The mixture was stirred under argon for 0.5 h and the mixture was allowed to reach room temperature and stirred overnight. The resulting mixture was diluted with water and extracted three times with ethyl acetate. The organic phases were combined and washed with brine. After drying over magnesium sulfate, the solution was filtered and the solvent was evaporated under vacuum. The residue was purified by silica gel chromatography, eluting agent as indicated in each procedure.

Example 7

Removal of the N-9-fluorenylmethoxycarbonyl (Fmoc) Group

A solution of N-(9-fluorenylmethoxycarbonyl) amino acid (1 eq.) in 30% diethylamine in acetonitrile was stirred 15 min at room temperature. The solvent was removed under vacuum to yield the desired product that was used without further purification.

Example 8

Removal of the Methyl Ester group

Amino acid methyl ester (0.2 eq.) was dissolved in methanol at room temperature 1N sodium hydroxide (0.65 mL) was added, the mixture was stirred for 0.5 h and 1N HCl (0.3 mL) was added, maintaining the temperature at around 0° C. After removing the methanol under vacuum, a second portion of 1N HCl (0.3 mL) was added to adjust the pH at ~2.5. The organic acid was extracted with $CH_2Cl_2$, dried over magnesium sulfate and concentrated in vacuo, yielding the desired product that was used for the next step without further purification.

Example 9

Coupling Reaction of Hydroxylated Benzoic Acid With the NH Part of an Amino Acid Using BOP Reagent The acid (0.1M in a 1-1 mixture of dioxan and dichloromethane) and BOP reagent (1.0 eq.) was stirred at room temperature under an inert atmosphere. The amine (1.2 eq.) was directly added followed by the base (triethylamine, 1.2 eq.). The reaction was stirred for 3 to 16 h. The suspension was then poured in an extraction vessel containing ethyl acetate and 1N hydrochloric acid and the organic layer washed with 3 portions of water before drying over magnesium sulfate. The solution was filtered and concentrated in vacuo before purification by flash chromatography.

Specific Examples for the Preparation of Derivatives in Accordance With the Present Invention

Example 10

Preparation of the N-[N'-(3',4'-dihydroxybenzoyl)-D-tyrosyl]-dopamine

Step A. Preparation of N-(tert-butoxycarbonyl)-D-tyrosine

The title compound was prepared from D-tyrosine (543 mg, 3.0 mmol), by following the procedure described in example 1. The product was isolated as a colorless syrup (740 mg, 88% yield).

$^1$H NMR (DMSO-$d_6$): 1.32 (s, 9H); 2.71 (dd, J=3.3, 12.9, 1H); 2.89 (dd, J=3.8, J=12.3, 1H); 4.00 (m, 1H); 6.64 (d, J=8.6, 2H); 6.95 (d, J=8.0, 1H); 7.03 (d, J=8.6, 2H) 9.18 (br s, 1H); 12.46 (s, 1H).

Step B. Preparation of N-(tert-butoxycarbonyl)-O-benzyl-D-tyrosine benzyl ester

The title compound was prepared from the product obtained in step A of this example (650 mg, 2.3 mmol) according to the indications of example 2a. The crude product was purified by silica gel column chromatography using 5% MeOH/$CHCl_3$ to yield the desired product (650 mg, 61%).

$^1$H NMR (DMSO-d$_6$): 1.32 (s, 9H); 2.83 (dd, J=9.8, 13.5, 1H); 2.93 (dd, J=5.5, 13.8 1H); 4.17 (q, J=7.1, 8.3, 1H); 5.05 (s, 2H); 5.08 (s, 2H); 6.91 (d, J=8.2, 2H); 7.13 (d, J=8.2, 2H); 7.28–7.44 (m, 10H).

Step C. N-(3',4'-dihydroxybenzoyl)-O-benzyl-D-tyrosine benzyl ester

The title compound was prepared from the product obtained in step B of this example (110 mg, 0.24 mmol) by the removal of the Boc group following the indications of example 3. The resulting unblocked derivative was then coupled with 3,4-dihydroxybenzoic acid according to the indications of example 4. The crude product was purified by silica gel column chromatography using 5% methanol/chloroform to yield the desired product as a white solid, mp. 140° C. (dec.), (88 mg, 74%).

$^1$H NMR (CDCl$_3$): 3.15 (m, 2H); 4.98 (s, 2H); 5.01 (m, 1H); 5.18 (m, 2H); 6.63 (d, J=7.4, 1H); 6.80 (d, J=7.4, 2H); 6.85 (d, J=8.9, 1H); 6.92 (d, J=7.4, 2H); 7.08 (d, J=7.4, 2H); 7.26 (s, 1H); 7.31–7.41 (m, 0H).

Step D. N-[N'-(3',4'-dihydroxybenzoyl)-O-benzyl-D-tyrosyl]-dopamine

The title compound was prepared from the product of step C of this example (200 mg, 0.39 mmol) by removing the benzyl ester group following the indications of example 5. The resulting unblocked derivative was coupled with dopamine hydrochloride according to the indications of example 6. Purification by silica gel chromatography (3%MeOH/EtOAc) provided the desired product, (88 mg, 40%) as a white solid, mp. 131° C. (dec.).

$^1$H NMR (DMSO-d$_6$): 2.60 (m, 2H), 3.03 (dd, J=7.9, 13.7, 1H); 3.16 (dd, J=5.3, 14.2, 1H); 3.36 (m, 2H); 4.79 (m, 1H); 5.02 (s, 2H) 6.69 (d, J=7.9, 1H); 6.71 (s, 1H); 6.85 (d, J=7.9, 1H); 6.89 (d, J=8.8, 2H); 7.19 (d, J=6.1, 2H); 7.27 (t, J=6.7, 1H); 7.30 (s 1H); 7.34 (d, J=7.4, 1H); 7.30–7.47 (m, 5H); 7.58 (d, J =7.7, 1H); 8.04 (br s, 4H).

Step E N-[N'-(3',4'-dihydroxybenzoyl)-D-tyrosyl]-dopamine

The title compound was prepared from the product of step D of this example (60 mg, 0.11 mmol) by following the indications in example 5. Purification by silica gel chromatography (100% EtOAc) provided the desired product, (21 mg, 43%) as a white solid, mp. 178° C. (dec.).

$^1$H NMR (DMSO-d$_6$): 2.60 (m, 2H); 2,89 (dd, J=8.0, 13.9, 1H); 3.11 (dd, J=5.5, 13.9, 1H); 3.36 (m, 2H); 4.74 (m, 1H); 6.50 (d, J=7.0, 1H); 6.68 (d, J=8.1, 1H); 6.72 (d, J=6.3, 1H); 6.73 (s, 1H); 6.83 (d, J=7.5, 1H); 7.11 (d, J=8.0, 2H); 7.38 (d, J=7.4, 2H); 7.26 (t, J=6.7, 1H); 7.48 (d, J=7.6, 1H); 8.04 (br s, 5H).

Example 11

Preparation of N-[N'-(p-hydroxybenzoyl)-L-tyrosyl]-dopamine

Step A. N-p-hydroxybenzoyl-O-tert-butyl-L-tyrosine tert-butyl ester

The title compound was prepared from O-tert-butyl-L-tyrosine tert-butyl ester (445 mg; 1.60 mmol) by following the indications of example 4. Purification by flash chromatography eluting with 20% ethyl acetate in hexane provided 291 mg (51%) of the title compound, mp. 106° C.

$^1$H NMR (CDCl$_3$): 1.31 (s, 9H), 1.41 (s, 9H), 3.18 (d, J=5.6, 2H), 4.91 (m, 1H), 6.68 (d, J=7.3, 1H), 6.82 (d, J=8.0, 2H), 6.92 (d, J=8.3, 2H), 7.07 (d, J=8.0, 2H), 7.56 (d, J=8.3, 2H), 8.41 br s, 1H).

Step B. N-[N'-(p-benzoyl)-L-tyrosyl]-dopamine

The tert-butyl protecting group was removed by treatment of the product of step A of this example (21 mg, 0.05 mmol) with trifluoroacetic acid according to the conditions in example 3. The residue was treated without further purification with dopamine hydrochloride according to the procedure of example 6, providing the title product (16 mg, 53%), mp. 161° C.

$^1$H NMR (acetone-d$_6$): 2.52–2.61 (m, 2H), 2.95 (dd, J=14.4, 8.2, 1H), 3.10 (dd, J=14.4, 8.2, 1H), 3.27–3.37 (m, 2H), 4.71–4.76 (m, 1H), 6.47 (d, J=8.4, 1H), 6.63–6.7 (m, 4H), 6.82 (d, J=6.9, 2H), 7.07 (m, 2H), 7.38 (d, J=5.2, 1H), 7.54 (d, J=8.0, 1H), 7.69 (d, J=7.7, 2H), 7.4–7.9 (br s, 2H), 8.12 (br s, 1H).

Example 12

Preparation of N-[N'-(3',4'-dihydroxybenzoyl)-L-tyrosyl]-dopamine

Step A. N-3',4'-dihydroxybenzoyl-O-tert-butyl-L-tyrosine tert-butyl ester

The title compound was prepared from O-tert-butyl-L-tyrosine tert-butyl ester (500 mg; 1.8 mmol) by following the indications of example 4. Purification by flash chromatography eluting with 10% methanol in methylene chloride provided 511 mg (80%) of the title compound, mp. 122° C.

$^1$H NMR: (CDCl$_3$):0.87 (s, 9H), 0.88 (s, 9H), 3.16 (m, 2H), 4.78 (d, J=7.5, 1H), 6.85 (d, J=9.1, 1H), 6.89 (d, J=8.5, 2H), 7.21 (d, J=8.5, 2H), 7.29 (d, J=9.1, 2H), 7.42 (s, 1H), 7.49 (d, J=7.5, 2H), 8.29 br s, 1H), 8.50 (br s, 1H).

Step B. N-[N'-(3',4'-dihydroxybenzoyl)-L-tyrosyl]-dopamine

The tert-butyl protecting group was removed by treatment of the product of step A of this example (184 mg, 0.42 mmol) with trifluoroacetic acid according to the indications of example 3. The residue was treated without further purification with dopamine hydrochloride according to the procedure of example 6, providing the title product (128 mg, 66%), mp.205° C.

$^1$H NMR (acetone-d$_6$):2.56 (m, 2H), 2.99 (dd, J=13.6, 7.9, 1H), 3.11 (dd, J=13.6, 5.3, 1H), 3.36 (m, 2H), 4.78 (m, 1H), 6.46 (d, J=7.8, 1H), 6.64 (d, J=7.8, 1H), 6.68 s, 1H), 6.70 (d, J=8.3, 2H), 6.80 (d, J=8.6, 1H), 7.09 (d, J=8.3, 2H), 7.24 (d, J=8.6, 1H), 7.39 (s, 1), 7.55 (m, 1 H), 7.65 (d, J=7.6, 1H), 7.5–8.4 (br s, 5H).

Example 13

Preparation of N-[N'-(p-hydroxybenzoyl)-L-phenylalanyl]-dopamine

Step A. N-p-hydroxybenzoyl-L-phenylalanine benzyl ester

The title compound was prepared from L-phenylalanine benzyl ester (400 mg; 1.58 mmol) by following the indications of example 4. Purification by flash chromatography eluting with 10% ethyl acetate in hexane containing 1% acetic acid provided 323 mg (92%) of the title compound, mp. 163° C.

$^1$H NMR: (CDCl$_3$):3.16 (dd, J=12.8, 8.9, 1H), 3.24 (dd, J=12.8, 8.9, 1H), 4.92 (m, 1H), 5.12 (s, 2H), 6.83 (d, J=6.6, 2H), 7.15–7.31 (m, 10H), 7.70 (m, 3H), 8.90 (br s, 1H).

Step B. N-[N'-(p-benzoyl)-L-phenylalanyl]-dopamine

The product obtained in step A of this example (287 mg, 0.76 mmol) following the indications of examples 5 and 6, provided, after flash chromatography eluting with 50% ethyl acetate in dichloromethane containing 1% acetic acid, the desired product (301 mg, 94%), mp. 196° C.

$^1$H NMR (acetone-d$_6$): (two conformers) 2.48 (t, J=7.6, 2H), 2.60 (t, J=7.8, 2H), 2.93 (m, 1H), 3.00 (dd, J=13.3, 3.8, 1H), 3.13–3.25 (m, 1H), 3.32 (m, 1H), 4.59 (m, 1H), 6.41 (d, J=7.1, 1H), 6.57 (m, 2H), 6.76 (m, 2H), 7.12 (m, 1H), 7.21 (d, J=7.4, 2H), 7.26 (d, J=7.5, 1H), 7.65 (d, J=7.4, 2H), 8.00 (t, J=5.7, 1H), 8.21 (d, J=8.3 (1H), 8.59 (s, 1H), 8.69 (s, 1H), 9.92 (s, 1H).

Example 14

Preparation of N-[N'-(3',4'-dihydroxybenzoyl)-L-phenylalanyl]-dopamine

Step A. N-3,4-dihydroxybenzoyl-L-phenylalanine benzyl ester

The title compound was prepared from L-phenylalanine benzyl ester (400 mg; 1.57 mmol) by following the indications of example 4. Purification by flash chromatography eluting with 40% ethyl acetate in hexane containing 1% acetic acid provided 323 mg (60%) of the title compound, mp. 155° C.

$^1$H NMR: (CDCl$_3$):3.24 (dd, J=13.6, 8.5, 1H), 3.32 (dd, J=13.6, 5.2, 1H), 4.92 (m, 1H) 5.03 (m, 1H), 5.17 (s, 2H), 6.92 (d, J=8.0, 1H), 7.20–7.36 (m, 11H), 7.53 (s, 1H), 7.88 (d, J=7.3, 1H), 8.57 (br s, 1H).

Step B. N-[N'-(3',4'-benzoyl)-L-phenylalanyl]-dopamine

The product obtained in step A of this example (18 mg, 0.046 mmol) following the indications of examples 5 and 6, provided after flash chromatography eluting with 50% ethyl acetate containing 1% acetic acid, the desired product (19 mg, 73%), mp. 201° C.

$^1$H NMR (acetone-d$_6$): 2.52–2.59 (m, 2H), 3.04 (dd, J=13.7, 7.7, 1H), 3.18 (dd, J=13.7, 7.7 1H), 3.32 (m, 2H), 4.77 (dt, J=6.3, 7.6, 1H), 6.45 (d, J=7.1, 2H, 7.11–7.26 (m, 6H), 7.34 (s, 1H), 7.38 (m, 2H), 7.52 (d, J=7.6, 1H), 7.98 (s, 4H).

Example 15

Preparation of N-[N'-(3',4'-dihydroxybenzoyl)-glycyl]-dopamine

Step A. N-(3,4-dihydroxybenzoyl)-glycine tert-butyl ester

The title compound was prepared from glycine tert-butyl ester (400 mg; 2.57 mmol) by following the indications of example 4. Purification by flash chromatography eluting with 40% ethyl acetate in hexane containing 1% acetic acid provided 337 mg (52%) of the title compound, mp. 139° C.

$^1$H NMR: (acetone -d$_6$): 1.52 (s, 9H), 4.09 (d, J=5.5, 2H), 6.95 (d, J=7.3, 1H), 7.42 (d, J=7.3, 1H), 7.55 (s, 1H), 7.90 (br s, 1H), 8.34 (br s, 1H), 8.60 (br s, 1H).

Step B. N-[N'-(3',4'-benzoyl)-glycyl]-dopamine

The product obtained in step A of this example (277 mg, 1.03 mmol) following the indications of examples 3 and 6, provided, after flash chromatography eluting with 30% ethyl acetate in methylene chloride containing 1% acetic acid, the desired product (163 mg, 45%), mp. 155° C.

$^1$H NMR (acetone-d$_6$): 2.58 (t, J=7.1, 2H), 3.34 (dt, J=7.1, 5.1, 2H), 3.99 (d, J=5.3, 2H), 6.47 (d, J=8.0, 1H), 6.64 (d, J=8.0, 1 H), 6.67 (s, 1H), 6.85 (d, J=57.7, 1H), 7.31 (d, J=7.7, 1H), 7.44 (s, 1H), 7.47 (t, J=5.1, 1H), 7.94 (t, J=5.0, 1H), 7.4–8.0 (br s, 2H), 8.4 (br s, 2H).

Example 16

Preparation of N-[N'-(3',4'-dihydroxybenzoyl)-L-3,4-dihydroxy-phenylalanyl]-dopamine Step A. N-(tert-butoxycarbonyl)-O,O'-dibenzyl-3,4-dihydroxyphenyl-L-alanine benzyl ester The title compound was prepared from L-3,4-dihydroxyphenylalanine (DOPA) as described in examples 1 and 2b. In example 1, di-tert-butyl-dicarbonate (960 mg, 4.4 mmol) was used instead of Boc-ON to react with DOPA (790 mg, 4.0 mmol) with triethylamine (600 mg, 6.0 mmol) as base. The product was used for the next step without purification following the indications of example 2b, using 280 mg, (0.94 mmol). Purification by flash chromatography using 15% EtOAc/hexane provided the title compound as white crystals (180 mg, 34%), mp. 106–108° C.

$^1$H NMR (CDCl$_3$): 1.41 (s, 9H); 3.00 (d, J=4.9, 2H); 4.14 (s, 1H); 4.94 (d, J=7.4, 1H); 5.04–5.10 (m, 6H); 6.57 (d, J=7.8, 1H); 6.78 (d, J=8.4, 1H); 6.71 (s, 1H); 7.26–7.43 (m, 15H).

Step B. N-(3',4'-dihydroxybenzoyl)-O,O'-(dibenzyl)-L-3,4-dihydroxyphenylalanine benzyl ester The title compound was prepared by cleaving the Boc protecting group of the product prepared in step A of this example (130 mg, 0.23 mmol) and coupling it with 3,4-dihydroxybenzoic acid as described in example 3 and in example 4 respectively. Purification by flash chromatography using 5% MeOH/CHCl$_3$ yielded the desired product as a white solid (86 mg, 60%), mp. 215° C. (dec.).

$^1$H NMR (CDCl$_3$): 3.11 (m, J=6.1, J=14.1, 1H); 3.14 (dd, J=6.7, 13.9, 1H); 5.00 (s, 1H); 5.06–5.13 (m, 6H); 6.53 (d, J=8.0, 1H); 6.65 (d, J=7.6, 1H); 6.69 (s, 1H); 6.76 (d, J8.2, 1H); 6.82 (d, J=8.1, 1H); 7,05 (d, J=8.0, 1H); 7.25–7.47 (m, 15H); 7.47 (s, 1H).

Step C. N-(3',4'-dihydroxybenzoyl)-L-3,4-dihydroxyphenylalanine

The title compound was prepared by the reduction of the compound obtained in step B of this example (64 mg, 0.11 mmol) according to the indications found in example 5. The product was purified by flash chromatography eluting with 10% MeOH/EtOAc, affording the desired product as a solid (27 mg, 73% yield), mp. 121° C. (dec.).

$^1$H NMR (DMSO-d$_6$): 2.98 (m, 2H); 4.44 (m, 1H); 6.53 (d, J=7.9, 1H); 6.59 (d, J=7.6, 1H); 6.66 (s, 1H); 6.75 (d, J=8.2, 1H); 7,17 (d, J=7.9, 1H); 7.24 (s, 1H); 8.14 (d, J=8.2, 1H); 8.69 (s, 2H), 9.11 (s, 2H); 12.50 (s, H).

Step D. N-[N'-(3',4'-dihydroxybenzoyl)-L-3,4-dihydroxylphenylalanyl]-dopamine

The product from step C of this example was coupled with dopamine hydrochloride according to the procedure of example 6. Finally the O-benzyl ether protecting groups were hydrogenolyzed by following the indications of example 5. Purification by flash chromatography using 5% MeOH/EtOAc yielded the desired product (13.8 mg, 28%), mp. 142° C. (dec.).

$^1$H NMR (DMSO-d$_6$): δ2.48 (m, 2H); 2.67 (m, 2H); 3.32 (m, 2H); 4.47 (m, J=4.3, J =9.1, 1H); 6.42 (d, J=7.0, 1H); 6.51 (d, J=7.4, 1H); 6.58 (d, J=7.5, 1H); 6.59 (d, J=8.4, 1H); 6.66 (s, 1H); 6.74 (d, J=7.7, 1H); 7,15 (s, 1H); 7,17 (d, J=7.6, 1H); 7.22 (s, 1 H); 7.93 (t, J=5.7, 1H); 7.95 (d, J=8.5, 1H); 8.67 (br s, 6H, OH).

Example 17

Preparation of N-['-(3',4'-dihydroxybenzoyl)-trans-4-hydroxyprolyl]-dopamine Step A. N-(tert-butoxycarbonyl)-O-benzyl-trans-4-hydroxy-L-proline benzyl ester The title compound was prepared from trans-4-hydroxyproline as described in example 1 and 2b. The Boc derivative was prepared with the following quantities: di-tert-butyl-dicarbonate (960 mg, 4.4 mmol), trans-4-hydroxyproline (260 mg, 2.0 mmol), triethylamine (300 mg, 3.0 mmol). The product was used for the next step without purification. The benzylation was performed according to the indications of example 2b. Purification by flash chromatography using 20% EtOAc/hexane provided the title compound as syrup (368 mg, 48%).

$^1$H NMR (CDCl$_3$): 1.35 and 1.45 (s, 9H); 2.06 (m, 1H); 3.62 (m, 1H); 3.72 (m, 1H); 4.41 (t, J=7.4, 1H);4.51 (m, 1H); 5.15 (s, 4H); 7.34–7.37 (m, 10H).

Step B. N-(3,4-dihydroxybenzoyl)-O-benzyl-trans-4-hydroxy-L-proline benzyl ester The title compound was prepared by cleaving the Boc group of the compound obtained in step A of this example (350 mg, 0.85 mmol) by following the indications of example 3, and coupling it with 3,4-dihydroxybenzoic acid (196 mg, 1.27 mmol) according to example 4. Purification by flash chromatography using 5% MeOH/CHCl$_3$, provided the desired product as an oil (275 mg, 72.4% yield).

$^1$H NMR (DMSO-d$_6$): 2.02 (m, 1H); 2.24 (m, 1H); 3.79 (d, J=8.4,1H); 3.96 (d, J=10.1, 1H); 4.18 (s, 1H); 4.59 (t, J=8.4, 1H); 5.16 (s, 4H); 6.77 (d, J=7.9, 1H); 6.87 (d, J=7.7, 1H); 6.98 (s, 1H); 7.31–7.37 (m, 10H); 9.22 (br s, 1H); 9.42 (br s, 1H).

Step C. N-[N'-(3', 4'-dihydroxybenzoyl)-O-benzyl-trans-4-hydroxyprolyl]-dopamine The title compound was prepared from the product obtained in step B of this example (420 mg, 1.0 mmol) by removal of the benzyl ester group as described in example 5. The resulting acid was then coupled with dopamine hydrochloride as described in example 6. Flash chromatography eluting with 1% MeOH/EtOAc provided the desired product as a syrup (100 mg, 20%).

$^1$H NMR (DMSO-d$_6$): 1.88 (m, 1H); 2.28 (m, 1H); 2.53 (m, 2H); 3.16 (m, 2H); 3.58 (d, J=11, 1H); 3.73 (d, J=8.9, 1H); 4.11 (s, 1H) 4.35 (m, 2H); 4.48 (t, J=7.7, 1H); 6.44 (d, J=7.7, 1H); 6.58 (s, 1H); 6.62 (d, J=8.2, 1H); 6.77 (d, J=8.2, 1H); 6.90 (d, J=7.9, 1H); 7.00 (s, 1H); 7.21–7.30 (m, 5H); 7.95 (t, J=5.3, 1H); 8.62 (br s, 1H); 8.72 (br s, 4H); 9.16 (br s, 1H); 9.37 (br s, 1H).

Step D. N-[N'-(3',4'-dihydroxybenzoyl)-trans-4-hydroxyprolyl]-dopamine

The title compound was prepared from the compound of step C of this example (30 mg, 0.06 mmol) by following the indications of example 5. Purification by flash column chromatography with 3% MeOH/EtOAc afforded the desired product (18 mg, 75%) as white crystals, mp. 59–62° C.

$^1$H NMR (DMSO-d$_6$): 1.81 (m, 1H); 2.04 (m, 1H); 2.51 (m, 2H); 3.17 (m, 2H); 3.34 (d, J=6.6, 1H); 3.69 (d, J=8.3, 1H); 4.21 (s, 1H); 4.47 (t, J=8.3, 1H); 6.44 (d, J=6.7, 1H); 6.58 (s, 1H); 6.61 (d, J=7.7, 1H); 6.76 (d, J=8.2, 1H); 6.90 (d, J=8.0, 1H); 7.01 (s, 1 H); 8.90 (br s, 4H); 7.90 (t, J=5.3, 1H).

Example 18

Preparation of N-[N'-(3',4'-dihydroxybenzoyl)-L-seryl]-dopamine

Step A. N-(tert-butoxycarbonyl)-O-benzyl-L-serine benzyl ester

The title compound was prepared from N-(tert-butoxycarbonyl)-O-benzyl-L-serine, (300 mg, 1.0 mmol) as described in example 2b. Purification by flash chromatography eluting with 25% EtOAc/hexane provided the title compound as a syrup (370 mg, 96%).

$^1$H NMR (CDCl$_3$): 1.38 (s, 9H); 3.68 (m, 2H); 4.33 (q, J=6.2, J=6.0, 1H); 4.48 (m, 2H); 5.16 (m, 2H); 7.33 (m, 10H).

Step B. N-(3,4-dihydroxybenzoyl)-O-benzyl-L-serine benzyl ester

The title compound was prepared by cleaving the Boc group of the compound obtained in step A of this example (325 mg, 0.84 mmol) and coupling it with 3,4-dihydroxybenzoic acid as described in examples 3 and 4 respectively. Purification by flash chromatography eluting with 5% MeOH/CHCl$_3$ provided the desired product (220 mg, 62%).

$^1$H NMR (DMSO-d$_6$): 3.83 (m, 2H); 4.52 (m, 2H); 4.74 (q, J=6.3, J=6.4, 1H); 5.16 (m, 2 H); 6.78 (d, J=8.4, 1H); 7.26 (d, J=8.6, 1H); 7.28 (s, 1H); 7.29-7.32 (m, 10H); 8.42 (d, J=7.4, 1H); 9.15 (br s, 1H); 9.50 (br s, 1H).

Step C. N-[N'-(3', 4'-dihydroxybenzoyl)-O-benzyl-L-seryl]-dopamine

The title compound was prepared from the compound obtained in step B of this example (160 mg, 0.38 mmol) according to the procedures described in example 5 and 6 respectively. Purification by flash chromatography eluting with 2.5% MeOH/EtOAc provided the desired product (68 mg, 37%).

$^1$H NMR (DMSO-d$_6$): 2.52 (m, 2H); 3.19 (m, 2H); 3.69 (d, J=6.1, 2H); 4.49 (s, 2H); 4.64 (q, J=5.6, J=6.4, 1H); 6.42 (d, J=7.6, 1H); 6.57 (s, 1 H); 6.60 (d, J=8.2, 1H); 6.77 (d, J=8.3, 1H); 7.23 (d, J=7.2, 1H); 7.25 (s, 1H); 7.29–7.327 (m, 5H); 8.01 (d, J=7.9, 1H); 8.02 )t, J=5.4, 1H); 8.62 (br s, 1H); 8.72 (br s, 1H); 9.12 (br s, 1H); 9.47 (br s,1H).

Step D. N-[N'-(3', 4'-dihydroxybenzoyl)-L-seryl]-dopamine

The title compound was prepared from the compound obtained in step C of this example as described in example 5. The product was purified by flash chromatography eluting with 5% MeOH/EtOAc to provide the product (66%) as a solid, mp. 118° C. (dec.).

$^1$H NMR (DMSO-d$_6$): 2.51 (m, 2H); 3.17 (m, 2H); 3.66 (d, J=6.0, 2H); 4.39 (q, J=5.7, J=6.5, 1H); 6.43 (d, J=7.9, 1H); 6.57 (s, 1H); 6.59 (d, J=7.9, 1H); 6.79 (d, J=8.5, 1H); 7.25 (d, J=7.8, 1H); 7.32 (s, 1H); 7.86 (d, J=7.8, 1H); 7.95 (t, J=5.4, 1H); 9.00 (br s, 5H).

Example 19

Preparation of N-[N'-(p-hydroxybenzoyl)-L-alanyl]-dopamine

Step A. N-(tert-butoxycarbonyl)-L-alanine benzyl ester

The title compound was prepared from N-(tert-butoxycarbonyl)-L-alanine (567 mg, 3.0 mmol) as described in example 2a. Purification by flash chromatography eluting with 20% EtOAc/hexane provided the desired product as a syrup (800 mg, 96%).

$^1$H NMR (CDCl$_3$): 1.38 (d, J=7.3); 1.43 (s, 9H); 4.36 (s, 1H); 5.07 (s, 1H); 5.15 (m, 2H); 7.35 (s, 5H).

Step B. N-(p-hydroxybenzoyl)-L-alanine benzyl ester

The title compound was prepared from the product prepared in step A of this example (400 mg, 1.4 mmol) by removing the Boc group following the indications of example 3. The resulting product was then coupled with p-hydroxybenzoic acid according to example 4. Purification by flash chromatography eluting with 5% MeOH/CHCl$_3$ provided the desired product as white crystals (270 mg, 64%), mp. 82–84° C.

$^1$H NMR (DMSO-d$_6$): 1.40 (d, J=7.1, 3H); 4.49 (m, 1H); 5.13 (s, 2H); 6.80 (d, J=8.2, 2H); 7.35 (s, 5H); 7.75 (d, J=8.4, 2H); 8.53 (d, J=6.8, 1H); 9.99 (s, 1H).

Step C. N-[N'-(p-hydroxybenzoyl)-L-alanyl]-dopamine

The title compound was prepared from the compound obtained in step B of this example (150 mg, 0.50 mmol) following the indications of examples 5 and 6 for the cleavage of the benzyl ester and the coupling with dopamine hydrochloride. Purification by flash chromatography eluting with 5% MeOH/EtOAc provided the desired product (147 mg, 85%), mp. 127° C. (dec.).

$^1$H NMR (acetone-d$_6$): 1.28 (d, J=7.1, 3H); 2.51 (m, 2H); 3.17 (m, 2H), 4.40 (m, 1H); 6.43 (d, J=7.8, 1H); 6.57 (s, 1H); 6.59 (d, J=8.0, 1H); 6.80 (d, J=8.0, 2H); 7.77 (d, J=7.9, 2H); 7.86 (t, J=5.1, 1H); 8.12 (d, J=7.4, 1H); 8.16 (s, 1H); 8.71 (s, 1H); 9.95 (s, 1H).

Example 20

Preparation of N-[N'-(3', 4'-dihydroxybenzoyl)-L-alanyl]-dopamine

Step A. N-(3,4-dihydroxybenzoyl)-L-alanine benzyl ester

The title compound was prepared from N-(tert-butoxycarbonyl)alanine benzyl ester (400 mg, 1.4 mmol) by the removal of the Boc group following the indications of example 3. The resulting compound was then coupled with 3,4-dihydroxybenzoic acid according to indications of example 4. Purification by flash chromatography eluting with 5% MeOH/CHCl$_3$ provided the desired product as a syrup (180 mg, 41%).

$^1$H NMR (DMSO-d$_6$): 1.40 (d, J=7.1, 3H); 4.47 (m, 1H); 5.13 (s, 2H); 6.78 (d, J=8.2, 1H); 7.24 (d, J=7.9, 1H); 7.32 (s, 1H); 7.35 (s, 5H); 8.47 (d, J=6.7, 1H); 9.12 (s, 1H), 9.48 (s, 1H).

Step B. N-[N'-(3', 4'-dihydroxybenzoyl)-L-alanyl]-dopamine

The title compound was prepared from the compound of step A of this example (115 mg, 0.36 mmol) according to indications of example 5 and example 6 for the cleavage of the benzyl group and the coupling reaction with dopamine hydrochloride. Purification by flash chromatography eluting with 5% MeOH/EtOAc provided the desired product (56 mg, 15%), mp. 205° C. (dec.).

$^1$H NMR (DMSO-d$_6$): 1.40 (d, J=7.1, 3H); 2.63 (t, J=7.0, 2H); 3.38 (m, 2H); 4.58 (m, 1H); 6.52 (d, J=6.6, 1H); 6.67 (d, J=7.9, 1H); 6.71 (s, 1H); 6.87 (d, J=8.2, 1H); 7.32 (d, J=7.9, 1H); 7.39 (s, 1H); 7.45 (s, 1H), 7.60 (d, J=6.9, 1H); 8.04 (s, 4H).

Example 21

Preparation of N-['-(p-hydroxybenzoyl)-δ-(3-hydroxytyramine)-L-glutamyl]-dopamine Step A. N-(tert-butoxycarbonyl)-δ-benzyloxy-L-glutamic acid benzyl ester The title compound was prepared from N-(tert-butoxycarbonyl)-δ-benzyloxy-L-glutamic acid (169 mg, 0.50 mmol) as described in example 2a. Purification by flash chromatography eluting eith 20% EtOAc/hexane provided the title compound as white crystals (186 mg, 87%), mp. 71.5–74° C.

$^1$H NMR (CDCl$_3$): 1.42 (s, 9H); 1.99 (m, 1H); 2.22 (m, 1H); 2.44 (m, 2H); 4.39 (s, 1H); 5.09 (s, 4H); 7.33 (s, 10H).

Step B. N-(p-hydroxybenzoyl)-δ-benzyloxy-L-glutamic acid benzyl ester

The title compound was prepared from the product obtained in step A of this example (350 mg, 0.80 mmol) by the removal of the Boc group following the indications of example 3. The resulting product was coupled with p-hydroxybenzoic acid according to the indications found in example 4. Purification by flash chromatography eluting with 15% EtOAc/CH$_2$Cl$_2$ provided the desired product as a syrup (161 mg, 43%).

$^1$H NMR (DMSO-d$_6$): 2.06 (d, J=7.4, 1H); 2.15 (d, J=5.8, 1H); 4.50 (m, 1H); 5.07 (s, 2H); 5.14 (s, 2H); 6.81 (d, J=8.4, 2H); 7.34 (s, 10H); 7.77 (d, J=8.5, 2H); 8.51 (d, J=7.5, 1H); 10.02 (s, 1H).

Step C. N-['-(p-hydroxybenzoyl)-δ-(3-hydroxytyramine)-L-glutamyl]-dopamine

The title compound was prepared from the compound prepared in step B of this example (116 mg, 0.26 mmol) according to indications found in examples 5 and 6 for the cleavage of the benzyl groups and the coupling reaction with dopamine hydrochloride. Purification by flash chromatography eluting with EtOAc provided the desired product (61.2 mg, 44%), mp. 128° C. (dec.).

$^1$H NMR (DMSO-d$_6$): 1.89 (m, 1H); 1.98 (m, 1H); 2.14 (t, J=7.6, 2H); 2.50 (t, J=7.7, 4H); 3.17 (m, 4H); 4.33 (m, 1H); 6.39–6.43 (m, 2H); 6.56–6.62 (m, 4H); 6.81 (d, J=8.7, 2H); 7.77 (d, J=8.1, 2H); 7.85 (t, J=5.4, 1H); 7.90 (t, J=5.4, 1H); 8.16 (d, J=7.8, 1H), 8.61 (s, 2H); 8.72 (s, 2H); 9.98 (s, 1H).

Example 22

Preparation of N-['-(3',4'-dihydroxybenzoyl)-δ-(3-hydroxytyramine)-L-glutamyl]-dopamine Step A. N-(3,4-dihydroxybenzoyl)-δ-benzyloxy-L-glutamic acid benzyl ester The title compound was prepared from N-(tert-butoxycarbonyl)-δ-benzyloxy-L-glutamic acid benzyl ester (350 mg 0.82 mmol) by the removal of the Boc group following the indications found in example 3. The resulting product was coupled with 3,4-dihydroxybenzoic acid according to the indications found in example 4. Purification by flash chromatography eluting with 5% MeOH/EtOAc provided the desired product as a syrup (169 mg, 36%).

$^1$H NMR (CDCl$_3$): 2.15 (m, 1H); 2.30 (m, 1H); 2.49 (m, 2H); 4.81 (m, 1H); 5.06 (s, 2H); 5.16 (s, 2H); 6.86 (d, J=8.4, 2H); 7.12 (d, J=7.4, 1H); 7.19 (d, J=7.4, 1H); 7.26–7.31 (m, 10H); 7.46 (s, 1H).

Step B. N-[N'-(3',4'-dihydroxybenzoyl)-δ-(3-hydroxytyramine)-L-glutamyl]-dopamine The title compound was prepared from the compound obtained in step B of this example (130 mg, 0.28 mmol) according to the indications of example 5 and 6 for the removal of the benzyl groups and the coupling with dopamine hydrochloride. Purification by flash chromatography eluting with EtOAc provided the desired product as a foam (23 mg, 15%).

$^1$H NMR (DMSO-d$_6$): 1.87 (m, 1H,); 1.96 (m, 1H); 2.12 (s, 2H); 2.48 (t, J=7.6, 4H); 3.17 (m, 4H); 4.31 (m, 1H); 6.40 (d, J=7.6, 1H); 6.42 (d, J=7.3, 1H); 6.56 (s, 1H); 6.59 (d, J=8.6, 1H); 6.60 (s, 1H); 6.62 (d, J=7.7, 4H); 6.76 (d, J=8.0, 1H); 7.23 (d, J=9.6, 1H); 7.32 (s, 1H); 7.85 (t, J=5.3, 1H); 7.88 (t, J=5.9, 1H); 8.05 (d, J=7.8, 1H); 8.60 (s, 2H); 8.71 (s, 2H), 9.10 (s, 1H); 9.45 (s, 1H).

Example 23

Preparation of N-['-(3',4'-dihydroxybenzoyl)-δ-benzyloxy-L-glutamyl]-dopamine

Step A. N-[N'-(tert-butoxycarbonyl)-δ-benzyloxy-L-glutamyl]-dopamine

The title product was prepared by the reaction of dopamine hydrochloride with N-(tert-butoxycarbonyl)-δ-benzyloxy-L-glutamic acid (500 mg, 1.15 mmol) according to the indications of example 6. Purification by flash chromatography eluting with 25%

EtOAc/CH$_2$Cl$_2$ containing 1% acetic acid provided the desired product (400 mg, 65%) as a solid, mp. 58° C.

$^1$H NMR (acetone-d$_6$): 1.40 (s, 9H,); 1.95 (m, 1H); 2.14 (m, 1H); 2.46 (t, J=7.3, 4H); 2.65 (t, J=7.0, 2H), 3.38 (m, 2H); 4.19 (m, 1H); 5.1 1 (s, 2H), 6.19 (d, J=7.4, 1H); 6.55 (d, J=8.2, 1H); 6.74 (m, 2H); 7.29–7.33 (m, 5H), 7.43 (m, 1H), 7.75 (br s, 1H), 7.83 (br s, 1H).

Step B. N-[N'-(3',4'-dihydroxybenzoyl)-δ-benzyloxy-L-glutamyl]-dopamine

The title compound was prepared from the product of step A of this example (400 mg, 0.84 mmol) by the removal of the Boc group following the indications of example 3. The resulting compound was then coupled with 3,4-dihydroxybenzoic acid according to indications found in example 4. Purification by flash chromatography eluting with EtOAc containing 1% acetic acid provided the desired product (124 mg, 28%) as a solid, mp 108° C.

$^1$H NMR (acetone-d$_6$): 2.02 (m, 1H), 2.23 (m, 1H), 2.47 (m, 1H,); 2.50 (t, J=7.0, 2H); 3.35 (m, 2H); 4.61 (m, 1H); 5.05 (s, 2H), 6.48 (d, J=7.6, 1H); 6.64 (d, J=7.6, 1H); 6.68 (s, 1H); 6.82 (d, J=8.8, 1H); 6.90–7.03 (m, 1H); 7.25–7.31 (m, 5H), 7.44 (s, 1H), 7.49 (m, 1H), 7.66 (d, J=7.8, 1H); 7.5–8.8 (br s, 4H)

Example 24

Preparation of N-['-(3',4'-dihydroxybenzoyl)-L-glutaminyl]-dopamine

Step A. N-(tert-butoxycarbonyl)-L-glutamine benzyl ester

The title compound was prepared from N-(tert-butoxycarbonyl)-L-glutamine (250 mg, 1.0 mmol) as described in example 2b. Purification by flash chromatography eluting with 5% MeOH/EtOAc provided the desired product as crystals (320 mg, 96%), mp. 105.5–107.5° C.

$^1$H NMR (CDCl$_3$): 1.43 (s, 9H); 1.94 (m, 1H); 2.19 (m, 1H); 2.27 (m, 1H); 4.36 (s, 1H); 5.15 (m, 2H); 5.37 (d, J=7.3, 1H); 5.58 (s, 1H); 7.35 (m, 5H).

Step B. N-(3,4-dihydroxybenzoyl)-L-glutamine benzyl ester

The title compound was prepared from the product of step A of this example (300 mg, 0.89 mmol) by the removal of the Boc group following the indications of example 3. The resulting compound was then coupled with 3,4-dihydroxybenzoic acid according to indications found in example 4. Purification by flash chromatography eluting with 5% MeOH/EtOAc provided the desired product as a syrup (154 mg, 46%).

$^1$H NMR (DMSO-d$_6$): 1.96 (m, 1H); 2.06 (m, 1H); 2.21 (m, 2H); 4.40 (m, 1H); 5.13 (s, 2H); 6.78 (d, J=8.4, 1H); 6.82 (s, 1H); 7.24 ( d, J=7.6, 1H); 7.31 ( s, 2H); 7.33–7.36 (m, 5H,); 8.52 (d, J=6.9, 1H); 9.12 (s, 1H); 9.49 (s, 1H)

Step C. N-[N'-(3',4'-dihydroxybenzoyl)-L-glutamine]-dopamine

The title compound was prepared from the compound obtained in step B of this example (110 mg, 0.3 mmol) according to the indications found in example 5 and example 6 for the removal of the benzyl group and the coupling with dopamine hydrochloride. Purification by flash chromatography eluting with 7.5% MeOH/EtOAc provided the desired product as a solid (24.5 mg, 20%), mp. 164° C. (dec.).

$^1$H NMR (DMSO-d$_6$): 1.85 m, 1H); 1.95 m, 1H); 2.13 (s, 2H); 2.51 (s, 2H); 3.18 (m, 2H); 4.30 (m, 1H); 6.41 (d, J=7.9, 1H); 6.59 (d, J=7.8, 1H); 6.58 (s, 1H); 6.77 (d, J =8.5, 1H); 7.24 (d, J=8.7, 1H); 7.29 (s, 1H); 7.31 (s, 2H); 7.89 (t, J=5.3, 1H); 8.12 (d, J=7.6, 1H), 8.61 (s, 1H); 8.72 (s, 1H), 9.19 (s, 1H); 9.46 (s, 1H).

Example 25

Preparation of N-[N'-(p-hydroxybenzoyl)-L-leucyl]-dopamine

Step A. N-(p-hydroxybenzoyl)-L-leucine methyl ester

The title compound was prepared from L-leucine methyl ester hydrochloride (182 mg, 1.0 mmol) as described in example 4. Purification by flash chromatography eluting with 5% MeOH/CHCl$_3$ provided the desired product as white crystals (138 mg, 52%), mp. 138–140° C.

$^1$H NMR (DMSO-d$_6$): 0.88 (d, J=6.5, 3H); 0.93 (d, J=6.6, 3H); 1.55 (m, 1H); 1.68 (m, 1H); 1.75 (m, 1H); 3.36 (s, 3H); 4.47 (m, 1H); 6.82 (d, J=8.3, 2H); 7.77 (d, J=8.3, 2H); 8.42 (d, J=7.7, 1H); 9.99 (s, 1H).

Step B. N-[N'-(p-hydroxybenzoyl)-L-leucyl]-dopamine

The title compound was prepared from the compound obtained in step A of this example (96 mg, 0.40 mmol) by saponification of the methyl ester group according to example 8. The resulting acid was coupled with dopamine hydrochloride as in example 6. Flash chromatography eluting with 100% EtOAc provided the title compound (96 mg, 63%), mp. 161° C. (dec.).

$^1$H NMR (DMSO-d$_6$): 0.84 (d, J=5.5, 3H); 0.90 (d, J=6.6, 3H); 1.47 (m, 1H); 1.60 (m, 2H); 2.52 (m, 2H); 3.17 (m, 2H); 4.43 (m, 1H); 6.42 (d, J=8.0, 1H); 6.58 (d, J=6.1, 1H); 6.60 (s, 1H); 6.81 (d, J=9.1, 2H); 7.78 (d, J=8.4, 2H); 7.88 (t, J=5.5, 1H); 8.09 (d, J=8.5, 1H); 8.61 (s, 1H); 8.69 (s, 1H); 9.95 (s, 1H).

Example 26

Preparation of N-[N'-(3',4'-dihydroxybenzoyl)-L-leucyl]-dopamine

Step A. N-[N'(tert-butoxycarbonyl)-L-leucyl]-dopamine

The title compound was prepared from N-(tert-butoxycarbonyl)-L-leucine (187 mg, 0.75 mmol) by coupling with dopamine hydrochloride as in example 6. Flash column chromatography eluting with 25% EtOAc/CH$_2$Cl$_2$ provided the title compound as a syrup (195 mg, 71%).

$^1$H NMR (CDCl$_3$): 0.88 (t, J=6.5, 6H); 1.42 (s, 9H); 1.59 (s, 2H); 2.64 (t, J=6.7, 2H); 3.44 (m, 2H); 4.13 (s, 1H); 5.21 (s, 1H); 6.54 (d, J=7.9, 1H); 6.66 (s, 1H); 6.61 (s, 1H); 6.78 (d, J=7.7, 1H).

Step B. N-[N'-(3',4'-dihydroxybenzoyl)-L-leucyl]-dopamine

The title compound was prepared from the product obtained in step A of this example (176 mg, 0.48 mmol) by removing the Boc group following the indications of example 3. The resulting unblocked product was coupled with 3,4-dihydroxybenzoic acid according to example 4. Purification by flash chromatography eluting with 5% MeOH/EtOAc provided the desired product (42 mg, 22%), mp. 132° C. (dec.), $^1$H NMR (DMSO-d$_6$): 0.85 (d, J=5.6, 3H); 0.89 (d, J=5.2, 3H); 1.45 (m, 1H); 1.60 (m, 2H); 2.50 (t, J=7.2, 2H); 3.19 (m, 2H); 4.40 (m, 1H); 6.41 (d, J=7.8, 1H); 6.57 (s, 1H); 6.59 (d, J=7.6, 1H); 6.75 (d, J=7.5, 1H); 7.24 (d, J=10, 1H); 7.31 (s, 1H); 7.86 (t, J=5.5, 1H); 7.86 (d, J=7.8, 1H); 8.66 (s, 1H); 9.08 (s, 1H); 9.42 (s, 1H).

Example 27

Preparation of N-[N'-(p-hydroxybenzoyl)-L-prolyl]-dopamine

Step A. N-[N'-(tert-butoxycarbonyl)-L-prolyl]-dopamine

The title compound was prepared from N-(tert-butoxycarbonyl)-L-proline (108 mg, 0.50 mmol) in a coupling reaction with dopamine hydrochloride (189 mg, 1.0 mmol) according to example 6. Purification by flash column chromatography (5% MeOH/CHCl$_3$) provided the desired compound as a syrup (128 mg, 73%).

$^1$H NMR (DMSO-d$_6$): 1.32 (s, 6H); 1.39 (s, 3H,); 1.72 (m, 2H); 1.76 (m, 1H); 2.06 (m, 1H); 2.50 (s 2H); 3.13 (m, 1H); 3.25 (m, 2H); 3.27 (m, 1H); 3.98 (m, 1H); 6.43 (d, J=7.4, 1H); 6.56 (s, 1H); 6.61 (d, J=7.9, 1H); 7.86 (s, 1H); 8.31 (s, 1H); 8.61 (s, 1H); 8.71 (s, 1H).

Step B. N-[N'-(p-hydroxybenzoyl)-L-prolyl]-dopamine

The title compound was prepared from the product obtained in step A of this example by the removal of the Boc group following the indications in example 3. The resulting unblocked derivative was then coupled with p-hydroxybenzoic acid according to the indications found in example 4. Purification by flash chromatography eluting with EtOAc afforded the desired product (23 mg, 31%), mp. 165° C. (dec.).

$^1$H NMR (DMSO-d$_6$): 1.74 (m, 2H); 1.85 (s, 1H); 2.10 (s, 1H); 2.50 (s 2H); 3.17 (s, 2H); 3.46 (s, 1H); 3.57 (s, 1H);

4.09 (s, 1H); 6.43 (d, J=6.8, 1H); 6.58 (s, 1H); 6.61 (d, J=7.9, 1H); 6.78 (d, J=7.2, 2H); 7.43 (d, J=7.0, 2H); 7.83 (s, 1H); 8.63 (s, 1H); 8.73 (s, 1H); 9.88 (s, 1H).

Example 28

Preparation of N-[N'-(3',4'-dihydroxybenzoyl)-L-prolyl]-dopamine

The title compound was prepared from N-(tert-butoxycarbonyl)-L-prolyl-dopamine (150 mg, 0.43 mmol) by the removal of the Boc group following the indications found in example 3. The resulting unblocked derivative was then coupled with 3,4-dihydroxybenzoic acid as in example 4. Purification by flash chromatography eluting with EtOAc afforded the desired product (54 mg, 32%) as a solid, mp. 131° C. (dec.).

$^1$H NMR (DMSO-$d_6$): 1.73 (s, 2H); 1.85 (s, 1H); 2.09 (s, 1H); 2.50 (s 2H); 3.17 (s, 2H); 3.48 (s, 1H); 3.56 (s, 1H); 4.09 (s, 1H); 6.43 (d, J=6.7, 1H); 6.58 (s, 1H); 6.61 (d, J=78.4, 1H); 6.76 (d, J=7.3, 1H); 6.90 (s, 1H); 7.00 (s, 1H); 7.84 (s, 1H); 8.62 (s, 1H); 8.72 (s, 1H); 9.13 (s, 1H); 9.33 (s, 1H).

Example 29

Preparation of N-[N'-(p-hydroxybenzoyl)-L-tryptophanyl]-dopamine

Step A. N-[N'-(tert-butoxycarbonyl)-L-tryptophanyl]-dopamine

The title compound was prepared from N-(tert-butoxycarbonyl)-L-tryptophan (204 mg, 0.65 mmol) by coupling with dopamine hydrochloride according to the procedure of example 6. Purification by flash chromatography eluting with 2.5% MeOH/EtOAc provided the title compound as a syrup (215 mg, 75%).

$^1$H NMR (DMSO-$d_6$): 1.31 (s, 9H); 2.46 (t, J=7.4, 2H); 3.02 (m, 2H); 3.14 (m, 1H); 3.22(s, 1H); 4.15 (m, 1H); 6.43 (d, J=7.6, 1H); 6.58 (s, 1H); 6.62 (d, J=7.5, 1H); 6.66 (d, J=8.1, 1H); 6.97 (t, J=7.5, 1H); 7.05 (t, J=7.3, 1H); 7.10 (s, 1H); 7.31 (d, J=7.7, 1H); 7.58 (d, J=7.7, 1H); 7.86 (t, J=4.7, 1H); 8.62 (s, 1H); 8.71 (s, 1H); 10.77 (s, 1H).

Step B. N-[N'-(p-hydroxybenzoyl)-L-tryptophanyl]-dopamine

The title compound was prepared from the product obtained in step A of this example (175 mg, 0.40 mmol) by removing the Boc group following the indications of example 3. The resulting unblocked derivative was then coupled with p-hydroxybenzoic acid according to the indications of example 4. Purification by flash chromatography eluting with 5% MeOH/EtOAc afforded the desired product (125 mg, 68%) as a foam.

$^1$H NMR (DMSO-$d_6$): 2.50 (t, J=7.6, 2H); 3.11(m, 1H, CH$_{2(2)}$); 3.18 (m, 2H) 3.24 (m, 1H); 4.65 (m, 1H); 6.43 (d, J=8.1, 1H); 6.59 (s, 1H,); 6.61 (d, J=8.1, 1H); 6.76 (d, J=8.6, 2H); 6.98 (t, J=7.4, 1H); 7.05 (t,J=7.6, 1H); 7.17 (s, 1H); 7.30(d, J=8.1, 1H); 7.65 (d, J=8.0, 1H); 7.67 (d, J=8.3, 2H); 8.03 (t, J=5.3, 1H); 8.12 (d, J=8.2, 1H); 8.69 (s, 2H); 9.95 (s, 1H); 10.74 (s, 1H).

Example 30

Preparation of N-[N'-(3',4'-dihydroxybenzoyl)-L-tryptophyl]-dopamine

The title compound was prepared from N-[(N'-(tert-butoxycarbonyl)-L-tryptophyl]-dopamine (44 mg, 0.10 mmol) by the removal of the Boc group following the indications of example 3. The resulting unblocked derivative was then coupled with 3,4-dihydroxybenzoic acid according to the conditions found in example 4. Purification by flash chromatography eluting with EtOAc afforded the desired product (25 mg, 53%) as a yellow solid, mp. 119° C. (dec.)

$^1$H NMR (DMSO-$d_6$): 2.47 (m, 2H); 3.13 (m, 1H); 3.17 (m, 2H); 3.22 (m, 1H,); 4.62 (m, 1H); 6.43 (d, J=7.4, 1H); 6.59 (s, 1H); 6.61 (d, J=7.9, 1H); 6.73 (d, J=8.0, 1H); 6.97 (t, J=7.7, 1H); 7.04 (t, J=7.3, 1H); 7.15 (s, 1H); 7.29 (d, J=8.1, 1H); 7.24 (s, 1H); 7.29 (d, J=6.1, 1H); 7.64 (d, J=8.0, 1H); 7.66 (t, J=6.6, 1H); 8.00 (d, J=7.00, 1H); 8.61 (s, 1H); 8.72 (s, 1H); 9.07 (s, 1H); 9.44 (s, 1H); 10.74 (s, 1H);.

Example 31

Preparation of N-[N'-(3',4'-dihydroxybenzoyl)-L-methionyl]-dopamine

Step A. N-[N'-(tert-butoxycarbonyl)-L-methionyl]-dopamine

The title compound was prepared from N-(tert-butoxycarbonyl)-L-methionine (250 mg, 1.0 mmol) by coupling with dopamine (380 mg, 2.0 mmol) according to example 6. Purification by flash chromatography eluting with 30% EtOAc/CH$_2$Cl$_2$ yielded the title compound (230 mg, 60%).

$^1$H NMR (DMSO-$d_6$): 1.38 (s, 9H); 1.73 (m, 1H); 1.80 (m, 1H); 2.02 (s, 3H); 2.40 (m, 2H); 2.51 (t, J=7.6, 2H); 3.24 (m, 2H); 3.96 (m, 1H); 6.43 (d, J=7.6, 1H,); 6.57 (s, 1H); 6.61 (d, J=8.4, 1H); 6.87 (d, J=7.9, 1H); 7.78 (t, J=5.0, 1H); 8.62 (s, 1H); 8.70 (s, 1H).

Step B. N-[N'-(3',4'-dihydroxybenzoyl)-L-methionine]-dopamine

The title compound was prepared from the product prepared in step A of this example (150 mg, 0.40 mmol) by the removal of the Boc group following the indications found in example 3. The resulting unblocked derivative was coupled with 3,4-dihydroxybenzoic acid according to the indications of example 4. Purification by flash chromatography eluting with 5% MeOH/EtOAc afforded the desired product (40 mg, 24%) as a solid, mp. 126° C. (dec.).

$^1$H NMR (DMSO-$d_6$): 1.93 (m, 2H); 2.05 (s, 3H); 2.42 (m, 1H); 2.47 (m, 1H); 2.53 (t, J=7.8, 2H); 3.17 (m, 2H); 4.43 (m, 1H); 6.43 (d, J=8.0, 1H); 6.57 (s, 1H,); 6.59 (d, J=8.0, 1H); 6.77 (d, J=8.1, 1H); 7.25 (d, J 8.1, 1H); 7.32 (s, 1H); 7.89 (t, J=5.6, 1H); 8.08 (d, J=7.9, 1H); 8.67 (s, 4H).

Example 32

Preparation of N-[N'-(3',4'-dihydroxybenzoyl)-L-lysyl]-dopamine

Step A. N-[N$_\alpha$'-(9-fluorenylmethoxycarbonyl)-N$_\epsilon$"-(tert-butoxycarbonyl)-L-lysyl]-dopamine The title compound was prepared from N$_\alpha$-(9-fluorenylmethoxycarbonyl)-N$_\epsilon$'-(tert-butoxycarbonyl)-L-lysine (230 mg, 0.50 mmol) by coupling with dopamine hydrochloride as described in example 6. Purification by flash chromatography eluting with 40% EtOAc/CH$_2$Cl$_2$ provided the desired product as white crystals, mp. 58–61° C. (280 mg, 93%).

$^1$H NMR(DMSO-$d_6$): 1.20 (m, 1H); 1.23 (m, 1H); 1.33 (m, 2H); 1.48 (m, 1H); 1.55 (m, 1H); 2.52 (m, 2H); 2.89 (s, 2H); 3.15 (m, 1H); 3.22 (m, 1H); 3.89 (q, J$_{NH}$=8.5, J=6.8, 1H); 4.21 (t, J=6.1, 1H); 4.22 (d, J=7.4, 2H); 6.43 (d, J=7.9, 1H); 6.75 (s, 1H); 6.61 (d, J=7.6, 1H); 6.74 (s, 1H); 7.37 (t, J=8.0, 1H); 7.32 (t, J=7.4, 2H,); 7.42 (t, J=7.4, 2H); 7.72 (, J=6.6, 2H); 7.86 (t, J=5.7, 1H); 7.88 (d, J=7.5, 2H); 8.62 (br s, 1H); 8.71 (br s, 1H).

Step B. N-['-(3',4'-dihydroxybenzoyl)-L-lysyl]-dopamine

The title compound was prepared from the compound prepared in step A of this example (140 mg, 0.23 mmol) by the removal of the Fmoc group following the indications found in example 7. The resulting unblocked derivative was coupled with 3,4-dihydroxybenzoic acid according to the indications of example 4. Purification by flash chromatography using EtOAc provided the desired product (85 mg, 41%). The cleaving of the Boc group of the side chain of the coupled product (20 mg, 0.04 mmol) was achieved via an acid hydrolysis as described in example 3. The solvent and acid were removed under vacuum to afford the desired product (14.4 mg, 86%), mp.93.5° C. (dec.).

$^1$H NMR(DMSO-$d_6$): 1.17 (m, 2H); 1.52 (m, 2H); 1.68 (m, 2H,; 2.53 (m, 2H); 2.76 (s, 2H); 3.18 (m, 2H), 4.34 (q, J=6.7, J=8.2, 1H); 6.43 (d, J=8.0, 1H); 6.57 (s, 1H); 6.61 (d, J=8.0, 1H); 6.78 (d, J=8.2, 1H); 7.24 (d, J=8.2, 1H); 7.33 (s, 1H); 7.91 (t, J=4.7, 1H); 7.97 (d, J=7.9, 1H); 8.68 (s, 4H).

Example 33

Preparation of N-[N'-3',4'-dihydroxybenzoyl)-L-histidyl]-dopamine

Step A. N-[N$_\alpha$'-(fluorenylmethoxycarbonyl)-N"$_{im}$-(trityl)-L-histidyl]-dopamine The title compound was prepared from N$_\alpha$-(fluorenylmethoxycarbonyl)-N"$_{im}$-trityl-histidine (619 mg, 1.0 mmol) according to the indications found in example 6 with dopamine hydrochloride. Purification by flash chromatography eluting with 40% EtOAc/CH$_2$Cl$_2$ provided the desired product (390 mg, 52% yield).

$^1$H NMR(DMSO-$d_6$): 3.16 (m, 1H); 4.14 (m, 1H); 4.18 (d, J=7.4, 2H); 4.20 (t, J=5.4, 1H); 6.39 (d, J=7.6, 1H); 6.56 (s, 1H); 6.60 (d, J=7.8, 1H); 7.03 (s, 6H); 7.07 (t, J=7.4, 1H); 7.23 (s, 1H); 7.27 (m, 2H); 7.31 (s, 9H); 7.40 (m, 2H); 7.68 (m, 2H); 7.85 (d, J=7.8, 1H); 7.90 (d, J=7.7, 2H); 7.95 (s, 1H); 8.63 (br s, 1H); 8.72 (br s, 1H).

Step B. N-[N'-(3',4'-dihydroxybenzoyl)-L-histidyl]-dopamine

The title compound was prepared from the compound prepared in step A of this example (320 mg, 0.42 mmol) by the removal of the Fmoc group as described in example 7. The resulting unblocked derivative was coupled with 3,4-dihydroxybenzoic acid as in example 4. Purification by flash chromatography eluting with 5% MeOH/EtOAc provided the desired compound (85 mg, 41%). For the removal of the trityl group located on the side chain, the product (60 mg, 0.089 mmol) was hydrogenolyzed following the conditions found in example 5 affording the desired product (30 mg, 79%).

$^1$H NMR(DMSO-$d_6$): 2.47 (t, J=7.6, 2H); 2.96 (m, 2H); 3.17 (m, 2H); 4.57 (q, J=7.8, J$_{NH}$=6.7, 1H); 6.41 (d, J=9.1, 1H); 6.57 (s, 1H); 6.60 (d, J=8.2, 1H); 6.78 (d, J=8.4, 1H); 6.87 (s, 1H); 7.20 (d, J=7.8, 1H); 7.28 (s, 1H); 7.78 (s, 1H); 7.88 (t, J=5.7, 1H); 8.23 (d, J=7.9, 1H); 8.65 (s, 2H); 9.15 (s, 1H). 9.55 (s, 1H).

Example 34

Preparation of N-[N'-(3',4'-dihydroxybenzoyl)-L-aspartyl]-dopamine

Step A. N-tert-butoxycarbonyl-γ-cyclohexyl-L-aspartic acid benzyl ester

The title compound was prepared from N-tert-butoxycarbonyl-L-aspartic acid γ-cyclohexyl ester (1.0 g, 3.2 mmol) by an alkylation with benzyl bromide following the indication of example 2c. The resulting ester was obtained in 98% yield after purification by flash chromatography eluting with 15% EtOAc/hexane.

Step B. N-(3,4-dihydroxybenzoyl)-γ-cyclohexyloxy-L-aspartic acid benzyl ester

The title compound was prepared from the compound prepared in step A of this example by the removal of the Boc group according to the indications found in example 3 and coupling with 3,4-dihydroxybenzoic acid as indicated in example 4. Purification by flash chromatography eluting with 20% ethyl acetate/CH$_2$Cl$_2$ provided the title compound (260 mg, 52%).

Step C. N-[N'-(3',4'-dihydroxybenzoyl)-γ-cyclohexyloxy-L-aspartyl]-dopamine

The title compound was prepared from the compound prepared in step B of this example (259 mg, 0.59 mmol) by hydrogenolysis of the benzyl ester following the conditions outlined in example 5. The resulting product was then subjected to coupling with dopamine hydrochloride according to example 6. Purification by flash chromatography eluting with ethyl acetate afforded the title compound in 49% yield.

Example 35

Preparation of N-[N'-(3',4'-dihydroxybenzoyl)-sarcosyl]-dopamine

Step A. N-tert-butoxycarbonyl-sarcosine benzyl ester

The title compound was prepared from N-tert-butoxycarbonyl-sarcosine (2.0 g, 10.6 mmol) by an alkylation with benzyl bromide following the indication of example 2c. The resulting ester (2.89 g; 98%) was obtained after purification by flash chromatography eluting with 15% EtOAc/hexane.

$^1$H NMR (CDCl$_3$): 1.43 (d, 9H), 2.94 (d, 3H), 3.97 (d, 2H), 7.36 (s, 5H)

Step B. N'-(3,4-dihydroxybenzoyl)-sarcosine benzyl ester

The title compound was prepared from the compound prepared in step A of this example by the removal of the Boc group according to the indications found in example 3 and coupling with 3,4-dihydroxybenzoic acid as indicated in example 4. Purification by flash chromatography eluting with 80% ethyl acetate/CH$_2$Cl$_2$ provided the title compound (433 mg, 43%).

$^1$H NMR (CDCl$_3$): 3.1 (d, 3H), 3.5 (s, 2H), 5.2 (d, 2H), 6.9 (m, 3H), 7.40 (m, 5H), 9.40 (br s, 2H).

Step C. N-[N'-(3',4'-dihydroxybenzoyl)-sarcosinyl]-dopamine

The title compound was prepared from the compound prepared in step B of this example (278 mg, 0.88 mmol) by hydrogenolysis of the benzyl ester following the conditions outlined in example 5. The resulting product was then subjected to coupling with dopamine hydrochloride according to example 6. Purification by flash chromatography eluting with 5% MeOH/CH$_2$Cl$_2$/1% AcOH afforded the title compound in 50% yield.

$^1$H NMR (CDCl$_3$): 2.60 (t, 2H), 2.9 (d, 3H), 3.2 (q, 2H), 3.3 (t, 2H), 6.4–7.0 (m, 6H), 9.5 (br s, 4H).

Example 36

Preparation of N-[N'-(3',4'-dihydroxybenzoyl)-L-tyrosyl]-L-tyrosine

The dipeptide was prepared using the peptide synthesizer (ABI 430A) utilising Wang resin (0.5 mmol).

Step A. H$_2$N-L-tyrosyl-L-tyrosyl-resin

The N-Fmoc-L-tyrosine(t-Bu)-OH (1 mmol was activated over a period of 45 min with HOBT (1.0 eq.) and DCC (1.0 eq.) in 5 mL of N-methylpyrrolidone (NMP). At the same time, in a separate flask, the Fmoc protecting group on the tyrosine amino group bound to the polymer was removed by two successive treatments of 15 min with a solution of 30% piperidine in N-methylpyrrolidone, followed by a series of washes with NMP. The activated ester was then filtered and added to the resin. The suspension was stirred for 2 h. The Fmoc blocking group was then removed as previously described and the resin was successively washed with N-methylpyrrolidone and $CH_2Cl_2$.

Step B. N-[N'-(3',4'-dihydroxybenzoyl)-L-tyrosyl]-L-tyrosyl-resin

To the dityrosyl moiety bound on the resin (1 g) and 3,4-dihydroxybenzoic acid (85 mg; app. 3 eq.) in DMF (5 mL) and $CH_2Cl_2$ (2 mL) were added BOP (benzotriazol-1-yloxy-tris-dimethylamino)phosphonium hexafluorophosphate) (240 mg, app. 3 eq.) and diisopropylethylamine (125 μL; 4 eq.). The flask was stirred under nitrogen for a period of 16 h. The resin was filtered off, washed successively with DMF, MeOH and $CH_2Cl_2$, yielding 518 mg of crude resin.

Step C. N-[N'-(3',4'-dihydroxybenzoyl)-L-tyrosyl]-L-tyrosine

A mixture of 0.5 mL water in 4.5 mL of trifluoroacetic acid was cooled to 0° C. and was added to the crude resin. The resulting suspension was stirred, allowing the mixture to reach room temperature over a period of 2 h. The mixture was then filtered and the resin washed with 5 mL of acetic acid. The filtrate was evaporated to dryness in vacuo and the residue was purified by preparative HPCL, using a Supelcosil C-18 column, flow rate: 18 mL/min; gradient: 0.1% TFA from 0–30% acetonitrile over 40 min. Retention time: 21 min. 5 mg (4%) of the title compound was recovered (4% yield).

Example 37

Preparation of N-[N'-(3',4'-dihydroxybenzoyl)-L-tyrosyl]-glycine

Step A. N-(3,4-dihydroxybenzoyl)-O-tert-butyltyrosine tert-butyl ester

The hydrochloric salt of L-O-tert-butyltyrosine tert-butyl ester (800 mg, 2.4 mmol) was coupled with 3,4-dihydroxybenzoic acid by following the directions found in example 9. Purification by flash chromatography eluting with 40% ethyl acetate in hexane afforded the desired product (385 mg, 37%).

$^1$H NMR ($CDCl_3$): 1.31 (s, 9H), 1.42 (s, 9H), 3.13 (dd, J=5.8, 14.3, 1H), 3.17 (dd, J=6.3, 14.3, 1H), 4.85 (ddd, J=5.8, 6.3, 4.0, 1H), 6.77 (d, J=7.4, 1H), 6.5–6.9 (br s, 0.5H) and 7.26 (s, 0.5H), 6.80 (d, J=8.2,), 6.91 (d, J=8.0, 2H), 7.03 (d, J=8.2, 1H), 7.08 (d, J=8.0, 2H), 7.54 (s, 1H), 7.8–8.4 (br s, 1H).

Step B. N-[N'-(3',4'-dihydroxybenzoyl)-L-O-tert-butyltyrosyl]-glycine

The product of step A of this example (375 mg) was stirred with TFA (10 mL) for a period of 90 min. The mixture was evaporated to dryness in vacuo and several h with a mechanical pump providing a quantitative yield (200 mg) of the free acid. The acid was then condensed using the BOP procedure as found in example 9 with glycine tert-butyl ester hydrochloride salt (80 mg,1.5 eq.) and triethylamine (132 μL, 3.0 eq.) for a period of 15 h. Purification by flash chromatography eluting with 80% EtOAc in hexane afforded the desired product (120 mg, 89%) as the tert-butyl ester. The ester was hydrolysed using 0.5 mL of water and 7 mL of TFA with stirring for 1 h. The mixture was then evaporated in vacuo and purified by flash chromatography eluting with 5% methanol in dichloromethane containing 1% acetic acid to provide the desired product (35 mg, 34%).

$^1$H NMR (DMSO-$d_6$): 2.86 (dd, J=10.8, 13.7,1H), 2.98 (dd, J=1.4, 13.7, 1H), 3.66–3.92 (m, 2H), 6.61 (d, J 8.2, 2H), 6.73 (d, J 8.4, 1H), 7.09 (d, J8.2, 1H), 7.16 (d, J 8.4, 1H), 7.23 (s, 1H), 8.09 (d, J=8.5, 1H), 8.26 and 8.38 (2t, J=5.6, 2×0.5H).

Example 38

N-[N'-[N"-(3",4"-dihydroxybenzoyl)-L-tyrosyl]-glycyl]-dopamine

Step A. N-Boc-glycyl-dopamine

The title compound was prepared by coupling dopamine hydrochloride with tert-butoxycarbonylglycine (200 mg, 1.1 mmol) according to the procedure of example 9. Purification by flash chromatography afforded the title compound (214 mg, 64%).

$^1$H NMR (DMSO-$d_6$): 1.38 (s, 9H), 2.5–2.58 (m, 2H), 3.16–3.20 (m, 2H), 3.49 (d, J=5.7, 2H), 6.42 (d, J=7.9, 1H), 6.57 (s, 1H), 6.62 (d, J=7.9), 6.86 (d, J=5.2, 1H), 7.71–7.77 (m, 1H), 8.62 (s, 1H), 8.72 (s, 1H).

Step B. N-[N'-[N"-(3",4"-dihydroxybenzoyl)-L-tyrosyl]-glycyl]-dopamine

The product obtained in step A of this example was hydrolyzed under the conditions of example 3 providing an intermediate that was coupled with N-(3,4-dihydroxybenzoyl)-L-tyrosine under the conditions outlined in example 9. Purification by flash chromatography eluting with 5% methanol in ethyl acetate containing 1% acetic acid provided the title compound (30 mg, 19%).

$^1$H NMR (DMSO-$d_6$): 2.52 (t, J=7.8, 2H), 2.88 (dd, J=9.9, 13.8, 1H), 2.97 (dd, J=4.3, 13.8, 1H), 3.16–3.21 (m, 2H), 3.61 (dd, J=5.2, 16.5, 1H), 3.70 (dd, J=5.6, 16.5, 1H), 4.46–4.53 (m, 1H), 6.44 (dd, J=1.5, 8.2, 1H), 6.56 (d, J=1.5, 1H), 6.62 (d, J=8.2, 1H), 6.63 (d, J=8.5, 2H), 6.74 (d, J=7.9, 1H), 7.09 (d, J=8.5, 2H), 7.18 (dd, J=1.7, 7.9, 1H), 7.25 (d, J=1.7, 1H), 7.76 (t, J=5.4, 1H), 8.19–8.23 (m, 2H), 8.1–9.7 (br s, 5H).

Example 39

Preparation of N-[N'-(3',4'-dihydroxybenzoyl)-glycyl]-L-tyrosine

Step A. N-3,4-dihydroxybenzoyl-glycine

Coupling of the hydrochloride salt of glycine tert-butyl ester with 3,4-dihydroxybenzoic acid was obtained by following the indications of example 9. Purification by flash chromatography afforded 288 mg (81%) of the title compound after eluting with 4% methanol in methylene chloride.

$^1$H NMR (DMSO-$d_6$): 1.41 (s, 9H), 3.82 (d, J 5.6, 2H), 6.76 (d, J=8.0, 1H), 7.20 (d, J=8.0, 1H), 7.28 (s, 1H), 8.45 (t, J=5.6, 1H),9.13 (s, 1H), 9.47 (s, 1H).

Step B. N-[N'-(3',4'-dihydroxybenzoyl)-glycyl]-L-tyrosine

The product obtained in step A of this example was hydrolyzed by stirring in TFA (10 mL) for a period of 90 min. Evaporation of the acid in vacuo afforded a product that was then reacted with O-tert-butyl-L-tyrosyl-dopamine using the conditions outlined in example 9. Purification by flash chromatography eluting with 70% ethyl acetate in hexane provided 230 mg (67%) of the O-tert-butyl derivative of the title compound.

$^1$H NMR ($CDCl_3$) d 1.28 (s, 9H), 1.30 (s, 9H), 3.00 (d, J=5.4, 2H), 3.89–4.08 (m, 2H), 4.60–4.67 (m, 1H), 6.64 (d, J=7.3, 1H), 6.83 (d, J=8.0, 2H), 6.97–7.05 (m, 1H), 7.04 (d, J=8.1, 2H), 7.09–7.18 (m, 2H), 7.32–7.41 (m, 1H).

Treatment of the tert-butyl derivative with TFA for a period of 2 h provided a quantitative yield of the title product.

$^1$H NMR (DMSO-$d_6$): 2.75–2.93 (m, 2H), 3.73–3.87 (m, 2H), 4.35–4.44 (m, 1H), 6.62 (d, J=8.1, 2H), 6.76 (d, J=8.5,

1H), 6.98 (d, J=8.1, 2H), 7.20 (dd, J=1.6, J=8.5, 1H), 7.30 (d, J=1.6, 1H), 7.96 (d, J=8.1, 0.5H) 8.18 (d, J=7.7, 0.5H), 8.29–8.36 (m, 1H), 9.00–9.60 (br s, 4H).

Example 40

N-[-N'-[N"-(3",4"-dihydroxybenzoyl)-glycyl]-L-tyrosyl]-dopamine

Step A. N-L-tyrosine-dopamine

The title compound was prepared from N-tert-butoxycarbonyl-O-2,6-dichlorobenzyl-L-tyrosine (2.50 g, 5.7 mmol) according to the indications found in example 6 with dopamine hydrochloride. Purification by flash chromatography eluting with 50% EtOAc/hexane provided the desired product (3.03 g, 93%).

$^1$H NMR (DMSO-$d_6$): 1.31 (s, 9H), 2.45–2.55 (m, 2H), 2.67 (dd, J=10.2, 13.4, 1H), 2.86 (dd, J=4.1, 13.4, 1H), 3.10–3.18 and 3.20–3.29 (2m, 2H), 4.07 (ddd, J=4.1, 10.2, 8.5, 1H), 5.17 (s, 2H), 6.43 (d, J=7.8, 1H), 6.59 (s, 1H), 6.64 (d, J=7.8, 1H), 6.75 (d, J=8.5, 1H), 6.94 (d, J=8.2, 2H), 7.15 (d, J=8.2, 2H), 7.45 (t, J=8.1, 1H), 7.53 (d, J=8.1, 2H), 7.87 (t, J=4.9, 1H), 8.00–9.15 (br s, 2H).

Step B. N-[N'-[N"-(3",4"-dihydroxybenzoyl)-glycyl]-L-tyrosyl]-dopamine

The product obtained in step A of this example was hydrolyzed by stirring in TFA (10 mL) for a period of 30 min. Evaporation of the acid in vacuo afforded a product, part of which (148 mg, 0.70 mmol) was then reacted with N-3,4-dihydroxybenzoyl-glycine using the conditions outlined in example 9. Purification by flash chromatography eluting with 5% methanol in ethyl acetate provided 115 mg (25%) of the O-(2,6-dichlorobenzyl) derivative of the title compound. The latter protected dipeptide derivative (115 mg, 0.17 mmol) in 4 mL of methanol was then hydrogenolyzed according to the procedure found in example 5. Purification by flash chromatography eluting with 2% methanol in ethyl acetate provided 60 mg (68%) of the desired product.

$^1$H NMR (DMSO-$d_6$): 2.47 (t, J=7.7, 2H), 2.65 (dd, J=8.9, J=13.6, 1H), 2.83 (dd, J=4.7, 13.6, 1H), 3.08–3.23 (m, 2H), 3.71 (dd, J=5.6, J=16.2, 1H), 3.83 (dd, J=5.8, 16.2, 1H), 4.35 (ddd, J=4.7, 8.9, 8.4, 1H), 6.42 (d, J=7.7, 1H), 6.57 (s, 1H), 6.59 (d, J=8.3, 2H), 6.62 (d, J=7.7, 1H), 6.76 (d, J=8.0, 1H), 6.95 (d, J=8.3, 2H), 7.21 (dd, J=1.7,8.0, 1H), J=1.7, 1H), 7.94 (d, J=8.4, 1H), 7.96 (t, J=5.5, 1H), 8.37 (t, J 5.7, 1H), 8.50–8.85 (br s, 2H), 9.05–9.22 (br s, 2H), 9.20–9.60 (br s, 1H).

Example 41

N-[N'-[N"-(3",4"-dihydroxybenzoyl)-L-tyrosyl]-L-γ-O-benzyl-aspartyl]-dopamine

Step A. N-Boc-L-aspartyl-dopamine γ-benzyl ester trifluoroacetate

Coupling of N-Boc-L-aspartic acid γ-benzyl ester (1.50 g, 4.63 mmol) dopamine hydrochloride by following the indications of example 6. Purification by flash chromatography eluting with 50% ethyl acetate in hexane afforded 2.06 g (93%) of the title compound after eluting with 40% ethyl acetate in hexane.

$^1$H NMR (DMSO-$d_6$): 1.37 (s, 9H), 2.45–2.52 (m, 2H) 2.57 (dd, J=8.6, 15.9, 1H), 2.70–2.78 (m, 1H), 3.10–3.25 (m, 2H), 4.28–4.35 (m, 1H), 5.08 (s, 2H), 6.41 (d, J=7.9, 1H), 6.65 (s, 1H), 6.62 (d, J–7.9, 1H), 7.04 (d, J=7.8, 1H), 7.29–7,40 (m, 5H), 7.80 (s, 1H), 8.62 (s, 1H), 8.71 (s, 1H).

Step B. N-[N'-[N"-(3",4"-dihydroxybenzoyl)-L-tyrosyl]-L-γ-O-benzyl-aspartyl]-dopamine The product obtained in step A of this example (500 mg, 1.00 mmol) was hydrolyzed by following the indications of example 3. The resulting product was then coupled with N-3,4-dihydroxybenzoyl-L-tyrosine as indicated in example 6. Purification by flash chromatography eluting with 5% methanol in methylene chloride containing 1% acetic acid afforded 69 mg (35%) of the desired title compound.

$^1$H NMR (DMSO-$d_6$): 2 signal sets 2.45–2.67 (m, 3H), 2.75–2.98 (m, 3H), 3.10–3.25 (m, 2H), 4.39–4.52 (m, 1H), 4.57–4.69 (m, 1H), 5.04–5.06 (m, 2H), 6.42 (d, J=7.6, 1H), 6.57–6.76 (m, 4H), 7.05–7.35 (m, 7H), 7.71 (t, J=5.5, 1H), 7.93 (t, J=5.5, 1H), 8.12 (d, J–7.6, 1H), 8.26 (d, J=7.7, 1H), 8u.63 (s, 1H), 8.73 (s, 1H), 9.10 (s, 1H), 9.20 (s, 1H), 9.51 (s, 1H).

Example 42

Preparation of N-[N'-(3',4'-dihydroxyhydrocinnamoyl)-L-tyrosyl]-L-tyrosine

Step A. N-3,4-dihydroxyhydrocinnamoyl-O-benzyloxy-L-tyrosine

O-benzyloxy-L-tyrosine benzyl ester p-toluenesulfonate salt (1.01 g. 1.9 mmol) was coupled with 3,4-dihydroxyhydrocinnamoic acid following the indications of example 4. Purification by flash chromatography eluting with 50% ethyl acetate in hexane afforded 855 mg (84%) of the pure amide.

$^1$H NMR (DMSO-$d_6$): 2.29 (t, J=7.8, 2H), 2.55 (t, J=7.8, 2H), 2.85 (dd, J=8.5, 7.6, 1H), 2.94 (dd, J=6.1, 13.8, 1H), 4.45 (ddd, J=6.1, 8.9, 7.6, 1H), 5.03–5.09 (m, 4H), 6.39 (d, J=8.0, 1H), 6.5 6 (s, 1H), 6.61 (s, 1H), 6.8 8 (d, J=8.2, 2H), 7.07 (d, J=8.2, 2H), 7.27 (d, J=7.0, 2H), 7.30–7.40 (m, 8H), 7.43 (d, J=7.5, 1H), 8.29 (d, J=7.6, 1N), 8.61 (s, 1H).

Step B. N-3,4-dihydroxyhydrocinnamoyl-L-tyrosine

The deprotection of the amide was carried out using the conditions outlined in example 5. Purification by flash chromatography eluting with 10% methanol in dichloromethane afforded 190 mg (73%) of the title compound.

$^1$H NMR (DMSO-$d_6$): 2.27 (t, J=7.9, 2H), 2.53 (t, J=7.9, 2H), 2.72 (dd, J=9.4, 13.7, 1H), 2.89 (dd, J=5.0, 13.7, 1H), 4.33 (ddd, J=5.0, 9.4, 8.2, 1H), 6.39 (d, J=7.3, 1H), 6.55 (s, 1H), 6.59 (d, J=7.3, 1H),6.64 (d, J=8.1, 2H), 6.97 (d, J=8.1, 2H), 8.04(d,J=8.2, 1H), 8.4–8.9 (br s, 2H), 12–13 (br s, 1H).

Step C. N-[N'-(3',4'-dihydroxyhydrocinnamoyl)-L-tyrosyl]-L-tyrosine

The product obtained in step B of this example (48 mg, 0.14 mmol) was coupled with O-benzyloxy-L-tyrosine benzyl ester p-toluenesulfonate salt following the indications of example 4. Purification by flash chromatography eluting with 4% methanol in ethyl acetate containing 1% acetic acid afforded 68 mg (100%) of the pure title compound.

$^1$H NMR (DMSO-$d_6$): 2.21 (t, J=8.4, 2H), 2.47 (t, J=8.4, 2H), 2.57 (dd, J=9.9, 14.2, 1H), 2.80 (dd, J=7.9, 14.0, 1H), 2.86 (dd, J=3.3, 14.2, 1H), 2.93 (dd, J=4.9, 14.0, 1H), 4.33 (ddd, J=4.9, 7.9, 7.6, 1H), 4.44 (ddd, J=3.3, 9.9, 8.2, 1H), 6.36 (d, J=7.9, 1H), 6.54 (s, 1H), 6.59 (d, J=7.9, 1H), 6.61 (d, J=8.1, 2H), 6.65 (d, J=7.9, 2H), 6.98 (d, J=8.1, 2H), 7.00 (d, J=7.9, 2H), 7.90 (d, J=8.2, 1H), 8.05 (d, J=7.6, 1H), 8.57 (s, 1H), 8.60–8.80 (br s, 1H), 9.11 (s, 1H), 9.18 (s, 1H), 12.1–12.9 (br s, 1H).

Example 43

Preparation of N-[N'-[N"-(3",4"-dihydroxyhydrocinnamoyl)-L-tyrosyl]-L-tyrosyl]-dopamine The product obtained in step A of example 42 (100 mg, 0.29 mmol) was coupled with O-2,6-dichlorobenzyloxy-L-tyrosyl-dopamine salt following the indications of example 4. The crude material (315 mg) was used as isolated and subjected to hydrogenolysis using the conditions of example 5. Purification by flash chromatography eluting with 7% methanol in ethyl acetate containing 1% acetic acid afforded 100 mg (54%) of the pure title compound.

$^1$H NMR (DMSO-d$_6$): 2.42–2.50 (m, 2H), 2.58–2.65 (m, 2H), 2.69–2.76 (m, 2H), 2.79 (dd, J=8.3, 14.0, 1H), 2.85 (dd, J=8.0, 13.8, 1H), 2.96 (dd, J=6.3, 14.0, 1H), 3.03 (dd, J=6.2, 13.9, 1H), 3.29–3.42 (m, 2H), 4.47–4.53 (m, 1H), 4.53–4.59 (m, 1H), 6.52–6.59 (m, 2H), 6.69–6.80 (m, 8H), 7.02 (d, J=8.2, 2H), 7.06 (d, 8.5, 2H),

Example 44

Preparation of N'-(3',4'-dihydroxyhydrocinnamoyl)-L-3,4-dihydroxyphenylalanine

Step A. N'-(3',4'-dihydroxyhydrocinnamoyl)-L-3,4-O-dibenzyloxyphenylalanine benzyl ester The title compound was prepared by cleaving the Boc protecting group of the product prepared in step B of the example 16 (310 mg, 0.80 mmol) and coupling it with 3,4-dihydroxyhydrocinnamic acid as described in example 3 and in example 4 respectively. Purification by flash chromatography using 5% MeOH/CH$_2$Cl$_2$ containing 1% acetic acid yielded 220 mg (61%) of the desired product.

$^1$H NMR (DMSO-d$_6$): 2.29 (t, J=8.0, 2H), 2.55 (t, J=8.0, 2H), 2.73 (dd, J=8.5, 13.8, 1H), 2.82 (dd, 6.4, 13.8, 1H), 4.41 ddd, J=6.4, 8.5, 7.5, 1H), 5.03 (d, J=12.6, 1H), 6.56 (s, 1H), 6.60 (s, 1H), 6.60 (d, J=8.5, 1H), 6.61 (d, J=7.7, 1H), 7.22–7.38 (m, 5H), 8.26 (d, J=7.5, 1H), 8.4–9.2 (br s, 4H).

Step B. N'-(3',4'-dihydroxyhydrocinnamoyl)-L-3,4-dihydroxyphenylalanine

The title compound was prepared by the reduction of the compound obtained in step A of this example (135 mg, 0.30 mmol) according to the indications found in example 5. The product (90 mg, 83%) was obtained by filtering off the catalyst and evaporating the filtrate to dryness.

$^1$H NMR (DMSO-d$_6$): 2.27 (t, J=8.0, 2H), 2.55 (t, J=8.0, 2H), 2.65 (dd, J=8.6, 13.5, 1H), 2.66 (dd, 3.5, 13.5, 1H), 4.26 ddd, J=3.5, 8.6, 7.5, 1H), 6.39 (d, J=8.3, 1H), 6.41 (d, J=8.5, 1H), 6.56–6.60 (m, 4H), 7.82 (d, J=5.9, 1H), 8.0–9.7 (br s, 4H).

Example 45

Preparation of N'-[N''-(3'',4''-dihydroxyhydrocinnamoyl)-L-3',4'-dihydroxyphenylalanyl]-L-3,4-dihydroxyphenylalanine Boc-L-3,4-di-O-benzyloxyphenylalanine benzyl ester (325 mg, 0.68 mmol) was deprotected by treatment with TFA as indicated in example 3, providing the desired L-diO-benzyloxyphenylalanine benzyl ester that was coupled with Boc-L-dihydroxyphenylalanine following the indications of example 6. Purification by flash chromatography eluting with 2% methanol in methylene chloride afforded 275 mg (62%) of the dipeptide intermediate. Subsequent removal of the Boc group, again following the indications of example 3, provided the intermediate that was coupled with 3,4-dihydroxyhydrocinnamic acid as indicated in example 4.

The coupled product was hydrogenolyzed as isolated according to the indications of example 5. Purification by flash chromatography eluting with 7% methanol in ethyl acetate containing 1% acetic acid provided 75 mg (35%) of the title compound.

$^1$H NMR (DMSO-d$_6$): 2.22 (t, J=8.0, 2H), 2.46–2.53 (m, 3H), 2.74 (dd, J=8.1, 13.5, 1H), 2.80–2.85 (m, 1H), 2.86 (dd, 5.3, 13.5, 1H), 4.31 ddd, J=8.1, 5.3, 7.2, 1H), 4.38–4.46 (m, 1H), 6.37 (d, J=7.8, 1H), 6.43–6.49 (m, 2H), 6.54 (s, 1H), 6.56–6.63 (m, 4H), 6.64 (s, 1H), 7.93 (d, J=8.3, 1H), 8.01 (d, J=7.2, 1H), 8.5–8.9 (br s, 6H), 12.2–12.8 (br s, 1H).

Example 46

Preparation of N-[N'-[3',4'-dihydroxyhydrocinnamoyl)-L-3,4-dihydroxyphenylalanyl]-dopamine Step A. N-Boc-3,4-dihydroxyphenylalanyl-dopamine N-Boc-L-3,4-dihydroxyphenylalanine (1.00 g, 3.36 mmol) was coupled with dopamine hydrochloride according to the indications of example 6. Purification by flash chromatography eluting with 5% methanol in methylene chloride containing 1% acetic acid provided 1.17 g (83%) of the pure coupled product.

$^1$H NMR (DMSO-d$_6$): 1.32 (s, 9H), 2.44–2.52 (m, 2H), 2.53 (dd, J=9.7, 13.5, 1H), 2.71 (dd, J=4.3, 13.5, 1H), 3.07–3.28 (m, 2H), 3.98 (ddd, J=4.3, 9.7, 8.3, 1H), 6.42 (d, J=7.8, 1H), 6.45 (d, J=8.0, 1H), 6.57–6.63 (m, 4H), 6.64 (d, J=8.3, 1H), 7.80 (t, J=5.0, 1H), 8.0–9.8 (br s, 4H).

Step B. N-[N'-[N''-[3'',4''-dihydroxyhydrocinnamoyl)-L-3',4'-dihydroxyphenylalanyl]-L-3,4-dihydroxyphenylalanyl]-dopamine The product of step A of this example (1.17 g, 2.79 mmol) was treated with TFA as in example 3 to remove the Boc protecting group. A portion of the product thus obtained (260 mg, 0.60 mmol) was then coupled with 3,4-dihydroxyhydrocinnamic acid using the conditions as in example 4. Purification by flash chromatography eluting with 10% methanol in ethyl acetate containing 1% acetic acid provided 113 mg (38%) of the desired product.

$^1$H NMR (DMSO-d$_6$): 2.26 (t, J=7.7, 2H), 2.42–2.48 (m, 2H), 2.52 (t, J=7.7, 2H), 2.54 (dd, J=8.0, 13.6, 1H), 2.73 (dd, J=5.0, 13.6, 1H), 3.05–3.24 (m, 2H), 4.31 (ddd, J=5.0, 9.0, 8.3, 1H), 6.37 (d, J=8.0, 1H), 6.39–6.43 (m, 2H), 6.55–6.63 (m, 6H), 7.79 (t, 4.9, 1H), 7.91 (d, J=8.3, 1H), 7.4–10.0 (br s, 6H).

Example 47

Preparation of N-[N'-[N'-(3'',4''-dihydroxyhydrocinnamoyl]-L-3',4'-dihydroxyphenylalanyl]-L-3,4-dihydroxyphenylalanyl]-dopamine The product obtained in step A of example 46 (355 mg, 0.58 mmol) was deprotected by treating with TFA according to the indications of example 3. The product thus obtained was coupled with 3,4-dihydroxyhydrocinnamic acid according to the conditions of example 4. Purification by flash chromatography eluting with 5% methanol in ethyl acetate containing 1% acetic acid provided 70 mg (18%) of the title compound.

$^1$H NMR (DMSO-d$_6$): 2.22–2.28 (m, 2H), 2.45 (t, J=6.8, 2H), 2.46–2.57 (m, 3H), 2.62 (dd, J=8.3, 13.6, 1H), 2.71–2.80 (m, 2H), 3.06–3.21 (m, 2H), 4.25–4.32 (m, 1H), 4.32–4.40 ( 1H), 6.33–6.46 (m, 4H), 6.54–6.67 (m, 8H), 7.74 (t, J=5.0, 1H), 7.83 (d, J=8.0, 1H), 8.00 (d, J=8.0, 1H), 2.8–4.7 (br s, 8H).

Example 48

Preparation of N-[N'-(3',4'-dihydroxybenzoyl)-DL-3-fluorotyrosinyl]-dopamine Step A. N'-3',4'-dihydroxybenzoyl-O-benzyl-DL-3-fluorotyrosine benzyl ester N-Boc-O-benzyl-DL-3-fluorotyrosine benzyl ester (524 mg, 1.09 mmol) was deprotected by treating with TFA as indicated in example 3, providing the crude intermediate that was coupled with 3,4-dihydroxybenzoic acid as indicated in example 4. Purification of the product eluting with 15% ethyl acetate in methylene chloride provided 205 mg (34%) of the desired amide product.

$^1$H NMR (acetone-$d_6$): 3.17 (dd, J=5.6, 5.0, 2H), 5.13 (m, 1H), 5.13 (d, J=12, 2H), 5.23 (d, J=7.2, 2H), 6.58–7.40 (m, 16H).

Step B. N'-[(3',4'-dihydroxybenzoyl)-DL-3-fluorotyrosyl]-dopamine

The product obtained in step A of this example (179 mg, 0.32 mmol) was unblocked by hydrogenolysis according to example 5, providing a product that was then reacted with dopamine hydrochloride according to the indications of example 6. Purification by flash chromatography eluting with 10% methanol in ethyl acetate containing 1% acetic acid provided 118 mg (71%) of the title compound.

$^1$H NMR (acetone-$d_6$): 2.62 (d, J=6.0, 2H), 3.25 (dd, J=5.3, 6.8, 2H), 3.38 (q, J=6.2, 2H) 4.75 (q, J=6, 1H), 6.50 (d, J=7.7, 2H), 6.60 (m, 2H), 6.83 (d, J=8.3, 1H), 6.89 (d, J=8.9, 1H), 6.90 (s, 1H), 7.05 (d, J=11.7, 1H), 7.25 (d, J=8.2, 1H), 7.37 (s, 1H).

Example 49

Preparation of N-(3,4-dihydroxybenzoyl)-δ-N'-(3',4'-dihydroxyphenethyl)-L-glutamine α-benzyl ester Step A. N-Boc-δ-N'-(3',4'-dihydroxyphenethyl)-L-glutamine benzyl ester N-Boc-L-glutamic acid α-benzyl ester (800 mg, 2.37 mmol) was coupled with dopamine hydrochloride according to example 6. Purification by flash chromatography eluting with 5% methanol in ethyl acetate containing 1% acetic acid yielded 896 mg (80%) of white crystals.

$^1$H NMR (acetone-$d_6$): 1.07–2.15 (m, 2H), 2.27 (t, J=6.7, 2H), 2.63 (t, 7.2, 2H), 3.35 (q, T=6.4, 2H), 4.20 (m, 1H), 5.16 (q, J=14.0, 2H), 6.45 (d, J=5.8, 1H), 6.53 (d, J=7.8, 1H), 6.70 (s, 1H), 6.72 (d, J=7.6, 1H), 7.07 (s, 1H), 7.30–7.40 (m, 5H), 7.62–7.71 (s, 2H).

Step B. N-(3,4-dihydroxybenzoyl)-δ-N'-(3',4'-dihydroxyphenethyl)-L-glutamine α-benzyl ester The product prepared in step A of this example (800 mg, 2.37 mmol) was deblocked with TFA as described in example 3. The product thus obtained was then coupled with 3,4-dihydroxybenzoic acid according to the indications of example 4. Purification by flash chromatography eluting with 5% methanol in ethyl acetate containing 1% acetic acid yielded 896 mg (80%) of the title compound.

$^1$H NMR (acetone-$d_6$): 2.15–2.26 (m, 2H), 2.39 (d, J=4.7, 2H), 2.62 (t, 7.0, 2H), 3.35 (m, 2H), 4.62 (s, 1H), 5.16 (q, J=5.2, 2H), 6.50 (d, J=7.8, 1H), 6.70 (s, 1H), 6.90 (d, J=7.9, 1H), 7.03 (dd, J=8.3, 8.7, 1H), 7.31 (dd, J=6.4, 8.9, 1H), 7.35–7.41 (m, 6H), 7.68 (q, J=9.5, 1H), 8.2 (d, J=6.6, 1H).

Example 50

Preparation of N-[N'-(3',4'-dihydroxybenzoyl)-DL-m-tyrosyl]-dopamine

Step A. Preparation of N-(tert-butoxycarbonyl)-DL-m-tyrosine

The title compound was prepared from DL-m-tyrosine (1.0 g, 5.5 mmol), by following the procedure described in example 1. The product was isolated as a colorless syrup (1.18 g, 76%).

$^1$H NMR (DMSO-$d_6$): 1.30 (s, 9H); 3.15 (dd, J=3.1, 13.0, 1H); 4.10 (q, J=7.2, 1H); 6.20 (d, J=8.0, 1H); 6.50–6.80 (m, 4H), 7.2 (s, 1H), 10.0 (br s, 1H).

Step B. Preparation of N-(tert-butoxycarbonyl)-O-benzyl-DL-m-tyrosine benzyl ester The title compound was prepared from the product obtained in step A of this example (1.0 g, 3.56 mmol) according to the indications of example 2c. The crude product was purified by silica gel column chromatography using 5% MeOH/$CH_2Cl_2$ to yield the desired product (1.06 g, 65%).

$^1$H NMR ($CDCl_3$): 1.45 (s, 9H); 3.15 (d, J=3.3, 2H); 4.15 (q, J=7.2, 1H); 4.70 (J=5.7, 1H), 5.20 (d, J=1, 4H), 6.71 (d, J=6.8, 1H); 6.8 (s, 1H), 6.90 (d, 8.5, 1H), 7.2 (t, J=7.6, 1H), 7.3–7.5 (m, 1H).

Step C. N-(3,4-dihydroxybenzoyl)-O-benzyl-DL-m-tyrosine benzyl ester

The title compound was prepared from the product obtained in step B of this example (520 mg, 1.09 mmol) by the removal of the Boc group following the indications of example 3. The resulting unblocked derivative was then coupled with 3,4-dihydroxybenzoic acid according to the indications of example 4. The crude product was purified by silica gel column chromatography using 10% ethyl acetate in methylene chloride to yield 205 mg (34%) of the desired product.

$^1$H NMR (DMSO-$d_6$): 3.15 (d, J=3.1, 2H); 4.20 m, 1H), 5.20 (m, 4H); 6.70–7.80 (m, 17H), 8.6 (d, J=7.2, 2H).

Step D. N-[N'-(3',4'-dihydroxybenzoyl)-DL-m-tyrosyl]-dopamine

The title compound was prepared from the product of step C of this example (208 mg, 0.56 mmol) by removing the benzyl ester group following the indications of example 5. The resulting unblocked derivative was coupled with dopamine hydrochloride according to the indications of example 6. Purification by silica gel chromatography with 10% MeOH in ethyl acetate containing 1% acetic acid provided the desired product, (26 mg, 14%).

$^1$H NMR (DMSO-$d_6$): 2.62 (t, J=5.9, 2H), 3.20 (m, 2H); 4.7 (s, 1H); 6.70–7.5 (m, 12H), 8.5 (s, 1H), 9.3 (br s, 4H).

Example 51

Preparation of N-[N'-[N''-(3'',4''-dihydroxybenzoyl-L-tyrosyl]-L-tyrosyl]-dopamine N-[N'-(3',4'-dihydroxybenzoyl)-L-tyrosyl]-tyrosine (prepared as described in example 36, step C) (30 mg, 0.06 mmol) was coupled with dopamine hydrochloride according to the indications of example 6. Purification by flash chromatography eluting with 5% methanol in ethyl acetate containing 1% acetic acid provided 5 mg (14%) of the title compound. 1H NMR (acetone-$d_6$): 2.57 (t, J=7.0, 2H), 2.84 (dd, J=7.8, 13.6, 1H), 2.87–303 (m, 2H), 3.08 (dd, J=5.3, 13.9, 1H), 3.23–3.36 (m, 2H), 4.45–4.52 (m, 1H), 4.58–4.66 (m, 1H), 6.50 (dd, J–2.0, 7.8, 1H), 6.65 (d, J=8.3, 2H), 6.69 (d, J–7.8 1H), 6.70 (d, J=2.0, 1H), 7.07–7.11 (m, 1H), 7.10 (d, J=7.9, 2H), 7.21 (dd, J=1.9, 8.2, 1H), 7.39 (d, J=1.9, 1H), 7.40–7.46 (m, 1H), 7.55 (d, J=7.2, 1H).

The compounds listed in Table 3 were prepared following similar procedures as for the preparation of the derivatives described above (see new examples below); the number(s) in brakets after each root amino acid name is the number(s) of an example(s) below. Their activities are also listed in the same table demonstrating their potential usefulness.

TABLE 3

Anti-integrase activity ($IC_{50}$) of amino acid derivatives in accordance with general formula I above

| | Anti-integrase activity ($IC_{50}$) | |
|---|---|---|
| Root Amino acid (example no.) | Nα-Caffeoyl derivative μM | Other Nα-3,4-dihydroxyphenyl derivative μM |
| L-Aspartic acid (ex. 52) | 2.2 | |
| L-Tryptophan (ex. 53) | 1.5 | |
| L-3,4-Dihydroxyphenylalanine (ex. 54) | 0.62 | |
| L-3,4-Dihydroxyphenylalanine (ex. 55) | 0.38 | |
| L-Tyrosine (ex. 56) | | 0.78 |
| L-3,4-Dihydroxyphenylalanine (ex. 57) | | 0.106 |
| L-Cysteine (ex. 58) | | 0.21 |
| L-Serine (ex. 59) | 0.14 | |
| L-Glutamic acid (ex. 60) | 0.105 | |
| L-Aspartic acid (ex. 61) | 3.5 | |
| L-Aspartic acid (ex. 62) | 3.5 | |
| L-Glutamic acid (ex. 63) | | 2.8 |
| L-Tyrosine (ex. 64) | 3 | |

For the purposes of Table 3 the HIV-1 integrase inhibition assay was based on a known procedure (Hazuda, D. J. et al., Nucleic Acids Res. 22, 1121–1122 (1994)).

Example 52

Preparation of Nα-caffeoyl-Nγ-(3-hydroxytyramine)-L-aspartic acid benzyl ester

Step A. Preparation of Nα-tert-butoxycarbonyl-Nγ-(3-hydroxytyramine)-L-aspartic acid benzyl ester The title compound was prepared from commercially available Nα-tert-butoxycarbonyl-L-aspartic acid benzyl ester (2.0 g, 6.0 mmol), by following the procedure described in example 6. The product was isolated as a white solid (2 g, 76% yield).

$^1$H NMR (acetone-$d_6$): 1.4 (s, 9H), 2.6 (t, J=3.6, 2H), 2.7 and 2.80 (ABX, J=8.5, 15.0, 2H), 3.3 (d, J=3.2, 2H), 4.6 (br s, 1H), 5.2 (q, J=6.0, 2H), 6.3–7.5 (m, 10H), 7.68–7.72 (2 s, 2H).

Step B. Preparation of Nα-caffeoyl-Nγ-(3-hydroxytyramine)-L-aspartic acid benzyl ester The title compound was prepared from the product obtained in step A of this example (958 mg, 2.0 mmol) according to the indications of example 3, for 2 h. The crude intermediate was coupled with caffeic acid (565 mg, 3.1 mmol) according to the indications of example 4. The crude product was purified by flash chromatography using 30% AcOEt/CHCl$_3$ and 5–10% MeOH/CHCl$_3$ to yield the desired product (432 mg, 40%).

$^1$H NMR (DMSO-$d_6$): 2.5 (s, 2H), 2.6–2.7 (m, 2H), 3.2 (d, J=1.7, 2H), 4.8 (q, J=3.3, 1H), 5.1, (s, 2H), 6.3–7.0 (m, 13H), 8.0 (t, J=2.6, 1H), 8.4 (d, J=3.8, 1H), 8.5–9.4 (br s, 4H).

Example 53

Preparation of N-(N'-caffeoyl-L-tryptophanyl)dopamine

The title compound was prepared from N-(N'-tert-butoxycarbonyl-L-tryptophanyl)dopamine obtained in step A of example no. 29 (1.3 g, 2.8 mmol) according to the indications of example 3, for 2 h. The crude intermediate was coupled with caffeic acid (770 mg, 4.3 mmol) according to the indications of example 4. The crude product was purified by flash chromatography using 30% AcOEt/CH$_2$Cl$_2$/1% AcOH and 5–10% MeOH/CH$_2$Cl$_2$/1% AcOH to yield the desired product (899 mg, 63%).

$^1$H NMR (DMSO-$d_6$): 2.4 (q, J=3.7, 2H), 2.9–3.3 (m, 4H), 4.6 (q, J=2.8, 1H), 6.3–7.7 (m, 13H), 8.1 (t, J=2.7, 1H), 8.2 (d, J=4.0, 1H), 10.0 (br s, 4H), 10.8, (s, 1H).

Example 54

Preparation of N-(N'-caffeoyl-L-3,4-dihydroxyphenylalanyl)dopamine

The title compound was prepared from N-(N'-tert-butoxycarbonyl-L-3,4-dihydroxyphenylalanyl)dopamine obtained in step A of example no. 46 (878 mg, 2.0 mmol) according to the indications of example 3, for 2 h. The crude intermediate was coupled with caffeic acid (546 mg, 3.0 mmol) according to the indications of example 4. The crude product was purified by flash chromatography using 30% AcOEt/CH$_2$Cl$_2$/1% AcOH and 10% MeOH/CH$_2$Cl$_2$/1% AcOH to yield the desired product (407 mg, 41%).

$^1$H NMR (DMSO-$d_6$): 2.4 (s, 2H), 2.6–2.9 (m, 2H), 3.2 (m, 2H), 4.4 (m, 1H), 6.4–7.8 (m, 11H), 8.0 (m, 2H), 9.7 (br s, 6H).

Example 55

Preparation of N-(N'-caffeoyl-L-3,4-dihydroxyphenylalanyl)-3,4-dihydroxybenzylamine Step A. Preparation of N-(N'-tert-butoxycarbonyl-L-3,4-dihydroxyphenylalanyl)-3,4-dihydroxybenzylamine The title compound was prepared from Nα-tert-butoxycarbonyl-L-3,4-dihydroxyphenylalanine (575 mg, 1.9 mmol), by following the procedure described in example 6, using 3,4-dihydroxybenzylamine hydrobromide instead of dopamine hydrochloride. The crude material was purified by flash chromatography using 30, 50% AcOEt/CH$_2$Cl$_2$/1% AcOH to yield the desired product as white crystals (457 mg, 56% yield).

$^1$H NMR (DMSO-$d_6$): 1.3 (s, 9H), 2.5–2.8 (m, 2H), 4.2 (m, 3H), 6.4–6.8 (m, 7h), 8.2 (s, 1H), 8.7 (br s, 4H).

Step B. Preparation of N-(N'-caffeoyl-L-3,4-dihydroxyphenylalanyl)-3,4-dihydroxybenzylamine The title compound was prepared from the product obtained in step A of this example (377 mg, 0.9 mmol) according to the indications of example 3, for 2 h. The crude intermediate was coupled with caffeic acid (246 mg, 1.35 mmol) according to the indications of example 4. The crude material was purified by flash chromatography using 50, 80% AcOEt/CH$_2$Cl$_2$/1% AcOH to yield the desired product (120 mg, 28%).

$^1$H NMR (DMSO-$d_6$): 2.6–2.9 (m, 2H), 4.2 (s, 2H), 4.6 (s, 1H), 6.3–7.7 (m, 11H), 8.0 (d, J=4.0, 1H), 8.3 (d, J=2.4, 1H), 9.5 (br s, 6H).

Example 56

Preparation of N-[N'-(3',4'-dihydroxybenzoyl)-L-tyrosyl]-3,4-dihydroxybenzylamine Step A. Preparation of N-(N'-tert-butoxycarbonyl-L-tyrosyl)-3,4-dihydroxybenzylamine The title compound was prepared from commercially available Nα-tert-butoxycarbonyl-L-tyrosine (1.5 g, 5.3 mmol), by following the procedure described in example 6.

The product was purified by flash chromatography using 30, 60% AcOEt/CH$_2$Cl$_2$ to yield the title product as white crystals (1.9 g, 88% yield).

$^1$H NMR (DMSO-d$_6$): 1.3 (s, 9H), 2.5–2.8 (m, 2H), 4.1 (t, J=4.5, 2H), 6.4–7.0 (m, 7H), 8.2 (s, 1H), 8.7 (br s, 2H), 9.2 (s, 1H).

Step B. Preparation of N-[N'-(3',4'-dihydroxybenzoyl)-L-tyrosyl]-3,4-dihydroxybenzylamine The title compound was prepared from the product obtained in step A of this example (1.4 g, 3.3 mmol) according to the indications of example 3, for 2 h. The crude intermediate was coupled with 3,4-dihydroxybenzoic acid (758 mg, 5.0 mmol) according to the indications of example 4. The crude product was purified by flash chromatography using 50–80% AcOEt/CH$_2$Cl$_2$/1% AcOH to yield the title product as a white solid (600 mg, 40%).

$^1$H NMR (DMSO-d$_6$): 2.7–3.0 (m, 2H), 4.2 (s, 2H), 4.6 (s, 1H), 6.3–7.7 (m, 10H), 8.0 (d, J=3.9, 1H), 8.2 (d, J=2.4, 1H), 9.5 (br s, 5H).

Example 57

Preparation of N-[N'-(3',4'-dihydroxyphenylacetyl)-L-3,4-dihydroxyphenylalanyl]dopamine N-(N'-tert-butoxycarbonyl-L-3,4-dihydroxyphenylalanyl)dopamine (1.5 g, 3.4 mmol, example no. 46, step A) was deprotected with TFA as described in example 3. The product thus obtained was then coupled with 3,4-dihydroxyphenylacetic acid (865 mg, 5.0 mmol) according to the indications of example 4. Purification by flash chromatography using 40–60% AcOEt/CH$_2$Cl$_2$ containing 1% AcOH and 5% MeOH/CH$_2$Cl$_2$ containing 1% AcOH yielded 120 mg (7%) of the title compound as white crystals.

$^1$H NMR (DMSO-d$_6$): 2.4–2.8 (m, 4H), 3.0–3.4 (m, 4H), 4.3 (s, 1H), 6.3–7.3 (m, 9H), 7.7–8.0 (m, 2H), 9.2 (br s, 6H).

Example 58

Preparation of N-[N'-(3',4'-dihydroxybenzoyl)-L-cysteinyl]dopamine

Step A. Preparation of N-[N'-(3,4-dihydroxybenzoyl)-S-trityl-L-cysteinyl]dopamine Commercially available Nα-(9-fluorenylmethoxycarbonyl)-S-trityl-L-cysteine (1.7 g, 2.9 mmol) was coupled with dopamine hydrochloride according to the indications of example 6. The crude N-[N'-(9-fluorenylmethoxycarbonyl)-S-trityl-L-cysteinyl]dopamine was deprotected according to the indications of example 7. The resulting intermediate was then coupled with 3,4-dihydroxybenzoic acid (278 mg, 1.8 mmol) according to the indications of example 4. The final product was purified by flash chromatography using 20–50% AcOEt/CH$_2$Cl$_2$ containing 1% AcOH to yield the desired derivative (644 mg, 35%) as a yellow crystals.

$^1$H NMR (DMSO-d$_6$): 2.5 (m, 4H), 3.2 (m, 2H), 4.4 (s, 1H), 6.3–7.4 (m, 21H), 7.8 (s, 1H), 8.2 (d, J=3.8, 1H), 8.5–9.5 (4 s, 4H).

Step B. Preparation of N-[N'-(3',4'-dihydroxybenzoyl)-L-cysteinyl]dopamine

The title compound was prepared from N-[N'-(3,4-dihydroxybenzoyl-S-trityl-L-cysteinyl]dopamine describe in step A (390 mg, 0.6 mmol) by following the indications of example 3. Purification by flash chromatography using 30–60% AcOEt/CH$_2$Cl$_2$ containing 1% AcOH gave 108 mg (45%) of the title compound as white crystals.

$^1$H NMR (DMSO-d$_6$): 2.5 (m,4H), 3.2 (m, 2H), 4.4 (br s, 2H), 6.3–7.5 (m, 6H), 7.7 (s, 1H), 8.2 (d, J=4.0, 1H), 8.6–9.5(4 s, 4H).

Example 59

Preparation of N-(N'-caffeoyl-L-seryl)dopamine

Step A. Preparation of N-(N'-tert-butoxycarbonyl-L-seryl)dopamine

The title compound was prepared from Nα-tert-butoxycarbonyl-L-serine (2.5 g, 12.0 mmol), by following the procedure described in example 6. The crude material was purified by flash chromatography using 30% AcOEt/CH$_2$Cl$_2$ and 5% MeOH/CH$_2$Cl$_2$ to yield the desired product as white crystals (1.6 g, 40% yield).

$^1$H NMR (DMSO-d$_6$): 1.4 (s, 9H), 2.5 (s, 2H), 3.1–3.3 (m, 2H), 3.5 (s, 2H), 3.9 (s. 1H, 4.8 (s, 1H), 6.4–6.7 (m, 4H), 7.8 (s, 1H), 8.6 and 8.7 (2 s, 2H).

Step B. Preparation of N-(N'-caffeoyl-L-seryl)dopamine

The title compound was prepared from the product obtained in step A of this example (796 mg, 2.3 mmol) according to the indications of example 3, for 2 h. The crude intermediate was coupled with caffeic acid (633 mg, 3.5 mmol) according to the indications of example 4. The crude material was purified by flash chromatography using 30% AcOEt/CH$_2$Cl$_2$ and 5–10% MeOH/CH$_2$Cl$_2$ to yield the desired product (282 mg, 30%) as yellow crystals.

$^1$H NMR (DMSO-d$_6$): 2.5 (d, J=4.0, 2H), 3.2 (s, 2H), 3.6 (s, 2H), 4.4 (s, 1H), 6.4–7.3 (m, 8H), 7.8 (s, 1H), 8.0 (m, 1H), 9.3 (br s, 5H).

Example 60

Preparation of N-[N'-caffeoyl-Nα-(3-hydroxytyramine)-L-glutamyl]dopamine

Step A. Preparation of Nα-tert-butoxycarbonyl-L-glutamic acid

The title compound was prepared from commercially available Nα-tert-butoxycarbonyl-L-glutamic acid benzyl ester (1.0 g, 3.0 mmol), by following the procedure described in example 5. The crude material was purified by flash chromatography using 30% AcOEt/CH$_2$Cl$_2$/1% AcOH to yield the desired product as a white powder (680 mg, 93% yield).

Step B. Preparation of N-[N'-tert-butoxycarbonyl-Nδ-(3-hydroxytyramine)-L-glutamyl]dopamine Nα-tert-butoxycarbonyl-L-glutamic acid (718 mg, 2.9 mmol) was coupled with dopamine according to the indications of example 6. The product was purified by flash chromatography using 15, 30% AcOEt/CH$_2$Cl$_2$ containing 1% AcOH and 10% MeOH/CH$_2$Cl$_2$ containing 1% AcOH to yield the desired product as a white powder (1.1 g, 76% yield).

$^1$H NMR (DMSO-d$_6$): 1.3 (s, 9H), 1.7–2.0 (m, 4H), 2.5 (s, 4H), 3.2 (m, 4H), 3.9 (d, J=1.9, 1H), 6.3–6.8 (m, 7H), 7.8 (d, J=2.4, 2H), 9.5 (br s, 4H).

Step C. Preparation of N-[N'-caffeoyl-Nδ-(3-hydroxytyramine)-L-glutamyl]dopamine The title compound was prepared from the product obtained in step B of this example (721 mg, 1.4 mmol) according to the indications of example 3, for 2 h. The crude intermediate was coupled with caffeic acid (335 mg, 2.0 mmol) according to the indications of example 4. The crude product was purified by flash chromatography using 50, 60% AcOEt/CH$_2$Cl$_2$ and 10% MeOH/CH$_2$Cl$_2$ to yield the desired product (484 mg, 60%) as yellow crystals.

$^1$H NMR (DMSO-d$_6$): 1.7–2.0 (m, 2H), 2.1 (s, 2H), 2.5 (s, 4H), 3.2 (m, 4H), 4.3 (m, 1H, 6.4–7.6 (m, 11H), 8.0 (m, 3H), 9.4 (br s, 6H).

Example 61

Preparation of N-(N'-caffeoyl-Oγ-benzyl-L-aspartyl) dopamine

Step A. Preparation of N-(N'-tert-butoxycarbonyl-Oγ-benzyl-L-aspartyl)dopamine

The title compound was prepared from commercially available Nα-tert-butoxycarbonyl-Oγ-benzyl-L-aspartic acid (3.0 g, 9.3 mmol), by following the procedure described in example 6. The product was isolated as a white solid (2.7 g, 64% yield).

$^1$H NMR (acetone-d$_6$): 1.5 (s, 9H), 2.76 (t, J=3.5, 2H), 2.95 and 3.05 (ABX, J=5.5, 13.0, 4H), 4.6 (d, J=3.0, 1H), 5.2 (s, 2H), 6.4–7.6 (m, 10H), 8.5 (br s, 2H).

Step B. Preparation of N-(N'-caffeoyl-Oγ-benzyl-L-aspartyl)dopamine

The title compound was prepared from the product obtained in step A of this example (1.0 g, 2.4 mmol) according to the indications of example 3, for 2 h. The crude intermediate was coupled with caffeic acid (640 mg, 3.5 mmol) according to the indications of example 4. The crude product was purified by flash chromatography using 30% AcOEt/CHCl$_3$ and 5% MeOH/CHCl$_3$ to yield the desired product as a yellow powder (549 mg, 45%).

$^1$H NMR (acetone-d$_6$): 2.6 (d, J=2.7, 2H), 2.8–3.0 (m, 4H), 3.4 (d, J=2.9, 2H), 4.9 (d, J=3.2, 1H), 5.1 (s, 2H), 6.4–7.6 (m, 11H), 8.2 (br s, 6H).

Example 62

Preparation of N-(N'-caffeoyl-L-aspartyl)dopamine

Step A. Preparation of N-(N'-benzyloxycarbonyl-Oγ-tert-butyl-L-aspartyl)dopamine The title compound was prepared from commercially available Nα-benzyloxycarbonyl-Oγ-tert-butyl-L-aspartic acid (2.5 g, 7.7 mmol), by following the procedure described in example 6. The crude material was purified using 20, 50% AcOEt/CH$_2$Cl$_2$. The product was isolated as a white solid (3.2 g, 91% yield).

$^1$H NMR (DMSO-d$_6$): 1.3 (s, 9H), 2.3–2.7 (m, 4H), 3.2 (s, 2H), 4.3 (d, J=2.6, 1H), 4.8 and 5.3 (ABX, J=5.6, 16.0, 2H), 6.3–7.4 (m, 8H), 7.5 (d, J=4.0, 1H), 7.9 (s, 1H), 8.6 and 8.7 (2×s, 2×OH).

Step B. Preparation of N-(N'-caffeoyl-Oγ-tert-butyl-L-aspartyl)dopamine

N-(N'-benzyloxycarbonyl-Oγ-tert-butyl-L-aspartyl) dopamine (1.0 g, 2.3 mmol) was deprotected by hydrogenolysis as described in example 5. The product thus obtained was then coupled with caffeic acid (621 mg, 3.5 mmol) according to the indications of example 4. Purification by flash chromatography using 30–50% AcOEt/CH$_2$Cl$_2$ containing 1% AcOH yielded 519 mg (47%) of the title compound as yellow crystals.

$^1$H NMR (DMSO-d$_6$): 1.3 (s, 9H), 2.4–2.7 (m, 4H), 3.2 (m, 2H), 4.7 (d, J=6.8, 1H), 6.4 –7.4 (m, 8H), 8.0 (s, 1H), 8.3 (d, J=8.0, 1H), 8.5–9.5 (br s,4H).

Step C. Preparation of N-(N'-caffeoyl-L-aspartyl)dopamine

The title compound was prepared from the product obtained in step B of this example (333 mg, 0.7 mmol) according to the indications of example 3, for 2 h. The crude product was purified by flash chromatography using 50–99% AcOEt/CH$_2$Cl$_2$ containing 1% AcOH to yield the desired product (200 mg, 60%).

$^1$H NMR (DMSO-d$_6$): 2.4–2.8 (m, 4H), 3.2 (s, 2H), 4.7 (d, J=2.6, 1H), 6.3–7.4 (m, 8H), 7.9 (s, 1H), 8.3 (s, 1H), 9.7 (br s, 4×OH), 13.0 (br s, 1H).

Example 63

Preparation of Nα-(3,4-dihydroxybenzoyl)-Nδ-(3-hydroxytyramine) L-glutamic acid

The title compound was prepared from N-(3,4-dihydroxybenzoyl)-δ-N'-(3,4-dihydroxyphenethyl)-L-glutamine α-benzyl ester obtained in step B of example no. 49 (266 mg, 0.5 mmol) according to the indications of example 5. The crude product was purified by flash chromatography using 30% AcOEt/CH$_2$Cl$_2$ /1% AcOH and 10% MeOH/CH$_2$Cl$_2$/1% AcOH to yield the desired product (208 mg, 95%) as white crystals.

$^1$H NMR (DMSO-d$_6$): 1.9–2.4 (m, 4H), 2.5 (t, J=7.0, 2H), 3.5 (d, J=5.0, 2H), 4.2 (s, 1H), 6.3–7.4 (m, 6H), 8.2 (s, 1H), 8.4 (d, J=6.0, 1H), 9.7 (br s, 4H), 12.0 (br s, 1H).

Example 64

Preparation of N-(N'-caffeoyl-L-tyrosyl)-3,4-dihydroxybenzylamine

The title compound was prepared from N-(N-tert-butoxycarbonyl-L-tyrosyl)-3,4-dihydroxybenzylamine (example 56, step A) (1.4 g, 3.3 mmol) according to the indications of example 3, for 2 h. The crude intermediate was coupled with caffeic acid (978 mg, 5.4 mmol) according to the indications of example 4. The crude product was purified by flash chromatography using 40–80% AcOEt/CH$_2$Cl$_2$ containing 1% AcOH to yield the title product as yellow crystals (784 mg, 47%).

$^1$H NMR (DMSO-d$_6$): 2.7–3.0 (m, 2H), 4.1 (s, 2H), 4.6 (s, 1H), 6.3–7.4 (m, 12H), 8.2 (s, 1H), 8.4 (s, 1H), 9.5 (br s, 5H).

We claim:

1. An hydroxyphenyl derivative selected from the group consisting of a compound of formula

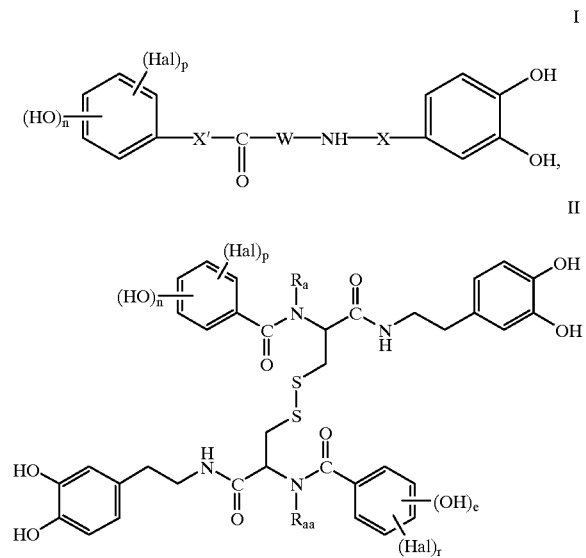

and when a compound of formula I comprises a carboxylic acid group pharmaceutically acceptable salts thereof and when a compound of formula I comprises an amino group pharmaceutically acceptable ammonium salts thereof, wherein n is 1, 2 or 3, e is 1, 2 or 3, Hal represents a halogen atom, p is 0, 1 or 2, r is 0, 1 or 2, X and X' each independently represents a single bond, a saturated straight or branched hydrocarbon group of 1 to 4 carbon atoms or a straight or branched hydrocarbon group of 2 to 4 carbon atoms comprising a carbon to carbon double bond, $R_a$ represents H or CH$_3$—, $R_{aa}$ represents H or CH$_3$—, W represents a group of formula

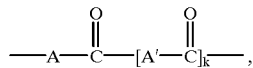

wherein k is 0 or 1, A and A' each independently represents a group of formula

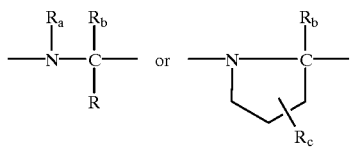

wherein $R_a$ is as defined above, $R_b$ represents H or $CH_3$—, $R_c$ represents H or OH, R is selected from the group consisting of H, $CH_3$—, $(CH_3)_2CH$—, $(CH_3)_2CHCH_2$—, $CH_3CH_2CH(CH_3)$—, $C_6H_5CH_2$—, $CH_3SCH_2CH_2$—, $HO_2CCH_2$—, $H_2NC(O)CH_2$—, $HO_2CCH_2CH_2$—, $H_3NC(O)CH_2CH_2$—, $H_2NCH_2CH_2CH_2CH_2$—, $HOCH_2$—, $CH_3CH(OH)$—, $HSCH_2$—,

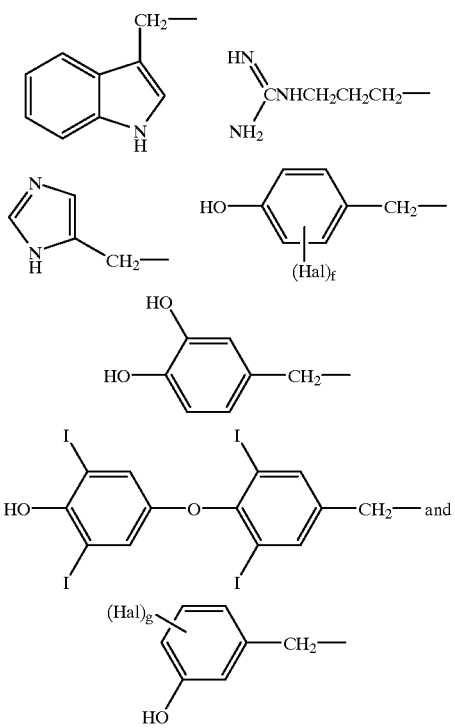

wherein Hal is as defined above and f is 0, 1 or 2, and g is 0, 1 or 2 and provided that when W represents a group of formula

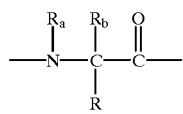

n is 3 when $R_a$ is H, $R_b$ is H and R is H, a group of formula $HO_2CCH_2CH_2$—, a group of formula

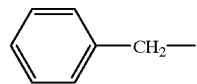

or a group of formula

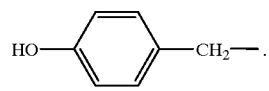

2. An hydroxyphenyl derivative as defined in claim 1 wherein n is 1 or 2, e is 1 or 2, p is 0, r is 0, f is 0 and g is 0.

3. A dopamine derivative selected from the group consisting of a compound of formula Ia

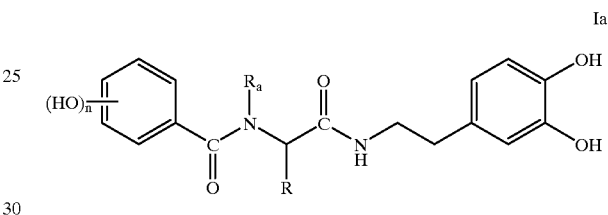

Ia and when a compound of formula Ia comprises a carboxylic acid group pharmaceutically acceptable salts thereof and when a compound of formula Ia comprises an amino group pharmaceutically acceptable ammonium salts thereof, wherein n is 1, 2, or 3, $R_a$ is selected from the group consisting of H and $CH_3$—, R is selected from the group consisting of H, $CH_3$—, $(CH_3)_2CH$—, $(CH_3)_2CHCH_2$—, $CH_3CH_2CH(CH_3)$—, $C_6H_5CH_2$—, $CH_3SCH_2CH_2$—, $HO_2CCH_2$—, $H_2NC(O)CH_2$—, $HO_2CCH_2CH_2$—, $H_2NC(O)CH_2CH_2$—, $H_2NCH_2CH_2CH_2CH_2$—, $HOCH_2$—, $CH_3CH(OH)$—, $HSCH_2$—

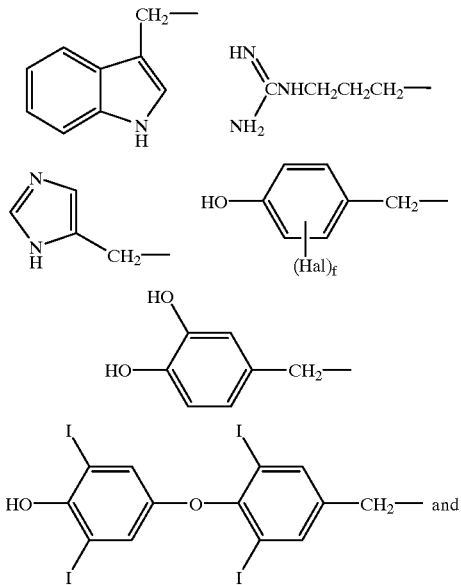

-continued

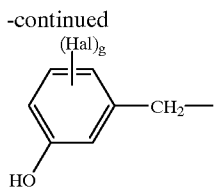

wherein Hal, f, and g are as defined in claim 1 and provided that n is 3 when $R_a$ is H and R is H, a group of formula $HO_2CCH_2CH_2—$, a group of formula

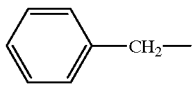

or a group of formula

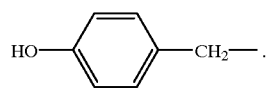

4. A dopamine derivative of formula Ia as defined in claim 3.

5. A dopamine derivative selected from the group consisting of a compound of formula Ib Ib

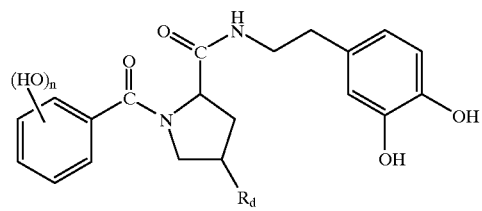

wherein n is 1 or 2, and $R_d$ is selected from the group consisting of H and OH.

6. A dopamine derivative selected from the group consisting of a compound of formula Ic Ic

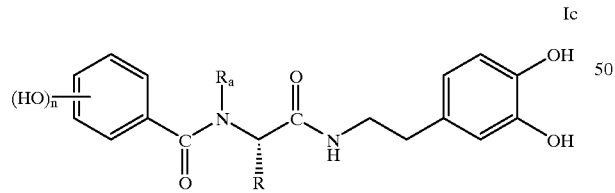

and when a compound of formula Ic comprises a carboxylic acid group pharmaceutically acceptable salts thereof and when a compound of formula Ic comprises an amino group pharmaceutically acceptable ammonium salts thereof, wherein n is 1 or 2, $R_a$ is selected from the group consisting of H and $CH_3—$, R is selected from the group consisting of H, $CH_3—$, $(CH_3)_2CH—$, $(CH_3)_2CHCH_2—$, $CH_3CH_2CH(CH_3)—$, $C_6H_5CH_2—$, $CH_3SCH_2CH_2—$, $HO_2CCH_2—$, $H_2NC(O)CH_2—$, $HO_2CCH_2CH_2—$, $H_2NC(O)CH_2CH_2—$, $H_2NCH_2CH_2CH_2CH_2—$, $HOCH_2—$, $CH_3CH(OH)—$, $HSCH_2—$

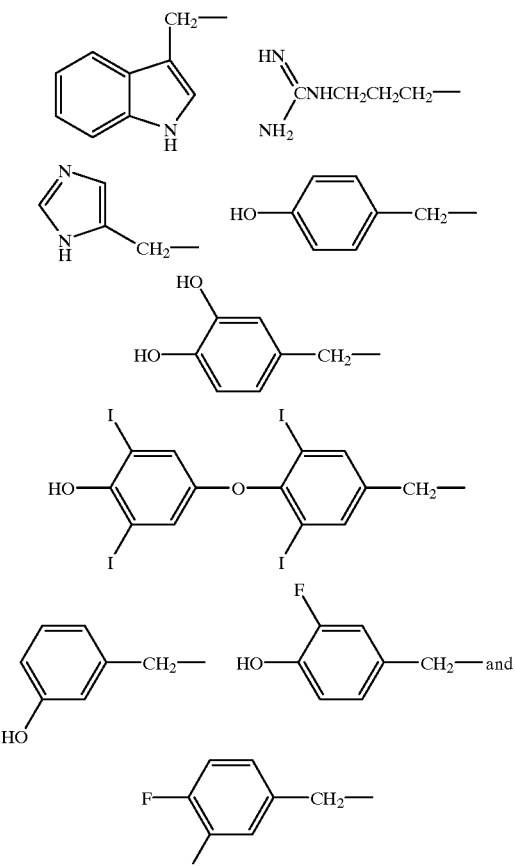

and provided that when $R_a$ is H, R cannot be H, a group of formula $HO_2CCH_2CH_2—$, a group of formula

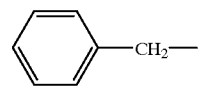

or a group of formula

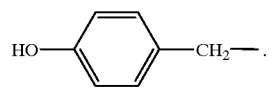

7. A dopamine derivative of formula Ic as defined in claim 6.

8. A dopamine derivative as defined in claim 3 wherein $R_a$ is H and R is a group of formula

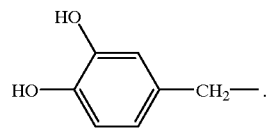

9. A dopamine derivative of formula

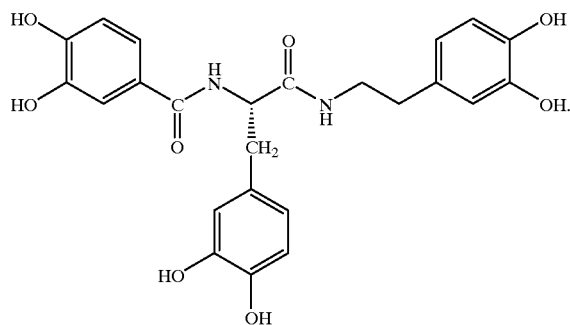

10. A dopamine derivative as defined in claim 3 wherein $R_a$ is H and R is a group of formula

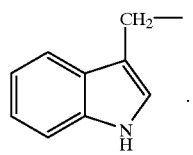

11. A dopamine derivative of formula

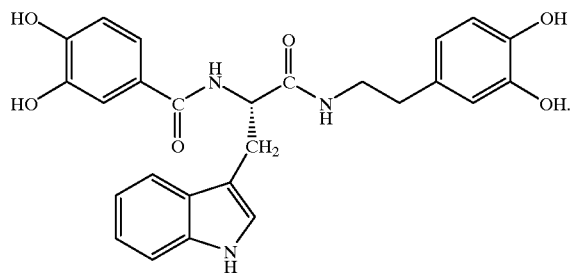

12. A pharmaceutical composition comprising a pharmaceutically acceptable carrier and a pharmaceutically effective amount of at least one hydroxyphenyl derivative as defined in claim 1.

13. A pharmaceutical composition comprising a pharmaceutically acceptable carrier and a pharmaceutically effective amount of at least one hydroxyphenyl derivative as defined in claim 2.

14. A pharmaceutical composition comprising a pharmaceutically acceptable carrier and a pharmaceutically effective amount of at least one dopamine derivative as defined in claim 3.

15. A pharmaceutical composition comprising a pharmaceutically acceptable carrier and a pharmaceutically effective amount of at least one dopamine derivative as defined in claim 4.

16. A pharmaceutical composition comprising a pharmaceutically acceptable carrier and a pharmaceutically effective amount of at least one dopamine derivative as defined in claim 5.

17. A pharmaceutical composition comprising a pharmaceutically acceptable carrier and a pharmaceutically effective amount of at least one dopamine derivative as defined in claim 6.

18. A pharmaceutical composition comprising a pharmaceutically acceptable carrier and a pharmaceutically effective amount of at least one dopamine derivative as defined in claim 7.

19. A pharmaceutical composition comprising a pharmaceutically acceptable carrier and a pharmaceutically effective amount of at least one dopamine derivative as defined in claim 8.

20. A pharmaceutical composition comprising a pharmaceutically acceptable carrier and a pharmaceutically effective amount of the dopamine derivative as defined in claim 9.

21. A pharmaceutical composition comprising a pharmaceutically acceptable carrier and a pharmaceutically effective amount of at least one dopamine derivative as defined in claim 10.

22. A pharmaceutical composition comprising a pharmaceutically acceptable carrier and a pharmaceutically effective amount of the dopamine derivative as defined in claim 11.

23. An hydroxylphenyl derivative as defined in claim 1 wherein W represents a group of formula

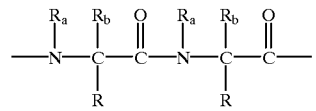

wherein each $R_a$ is independently as defined in claim 1, each $R_b$ is independently as defined in claim 1, and each R is independently as defined in claim 1.

24. A dopamine derivative selected from the group consisting of a compound of formula Id Id

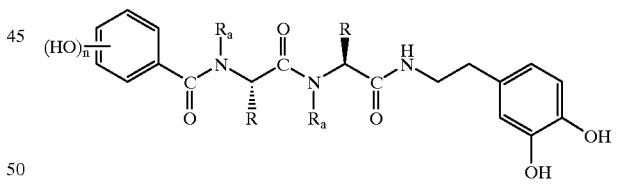

and when a compound of formula Id comprises a carboxylic acid group pharmaceutically acceptable salts thereof and when a compound of formula Id comprises an amino group pharmaceutically acceptable ammonium salts thereof, wherein n is 1 or 2, each $R_a$ is independently selected from the group consisting of H and $CH_3$—, and each R is independently selected from the group consisting of H, $CH_3$—, $(CH_3)_2CH$—, $(CH_3)_2CHCH_2$—, $CH_3CH_2CH(CH_3)$—, $C_6H_5CH_2$—, $CH_3SCH_2CH_2$—, $HO_2CCH_2$—, $H_2NC(O)CH_2$—, $HO_2CCH_2CH_2$—, $H_2NC(O)CH_2CH_2$—, $H_2NCH_2CH_2CH_2CH_2$—, $HOCH_2$—, $CH_3CH(OH)$—, $HSCH_2$—

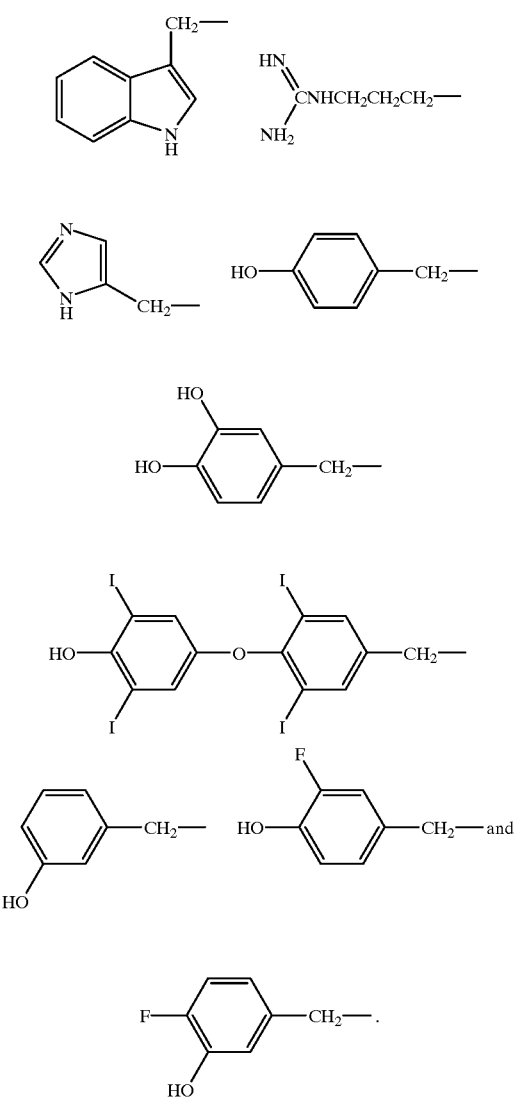
25. A dopamine derivative as defined in claim 24 wherein n is 2, each Ra is H and each R is a group of formula
26. A dopamine derivative of formula
27. A dopamine derivative of formula
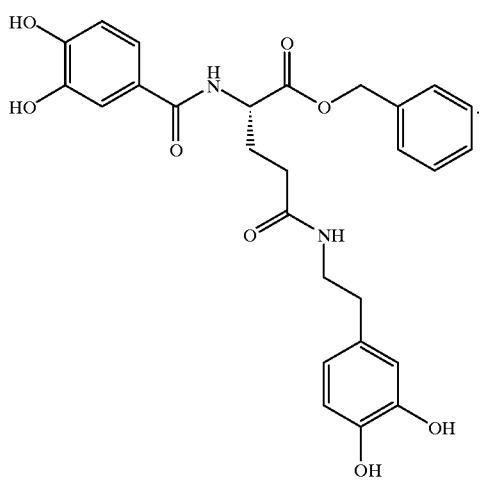
28. A dopamine derivative of formula
29. A dopamine derivative of formula
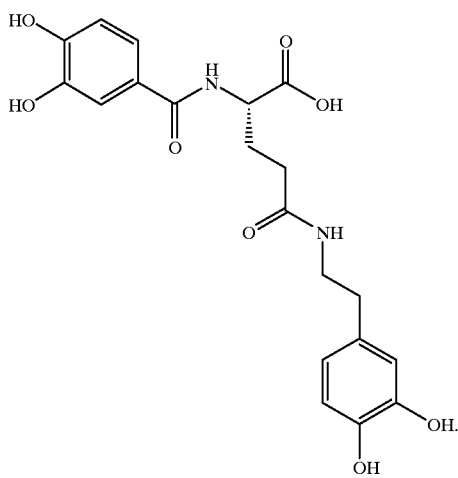

30. A dopamine derivative of formula
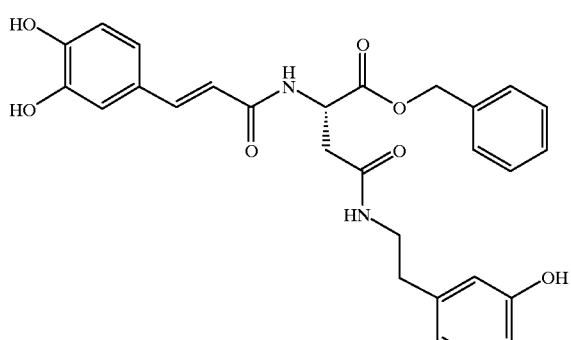
31. A dopamine derivative of formula
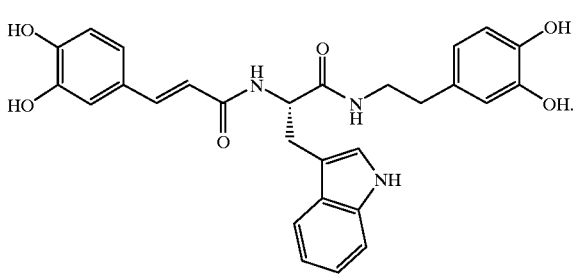
32. A dopamine derivative of formula
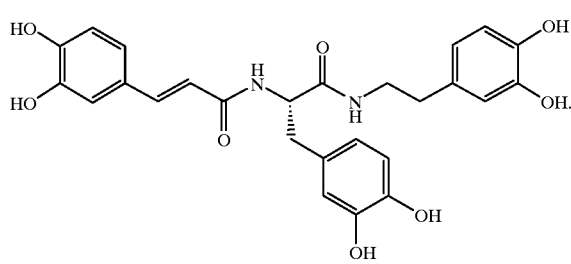
33. A compound of formula
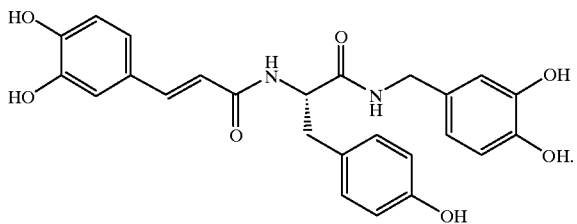
34. A dopamine derivative formula
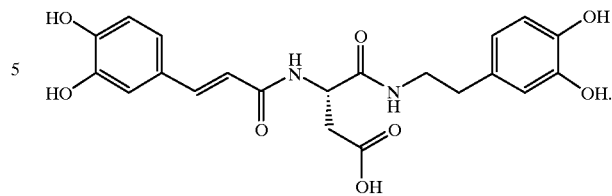
35. A compound of formula
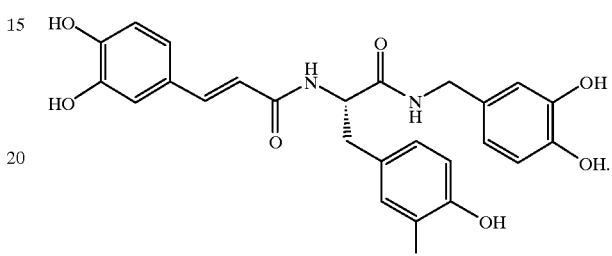
36. A dopamine derivative of formula
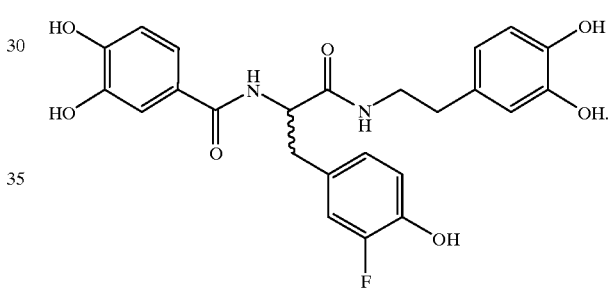
37. A compound of formula
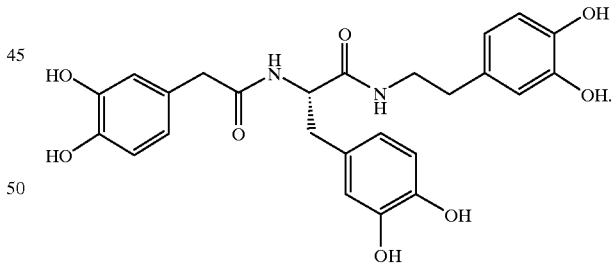
38. A dopamine derivative of formula
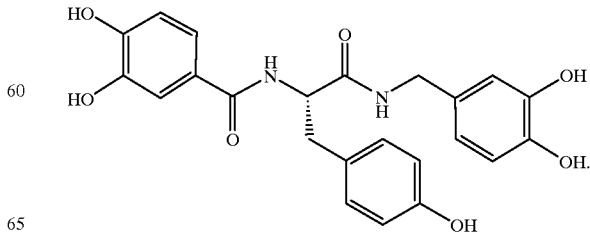

39. A dopamine derivative of formula

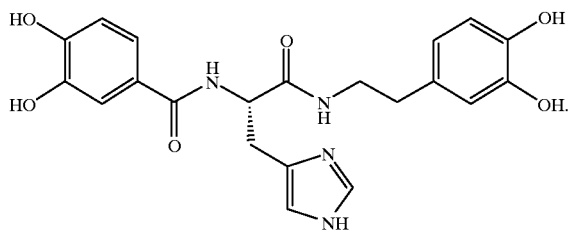

40. A dopamine derivative of formula

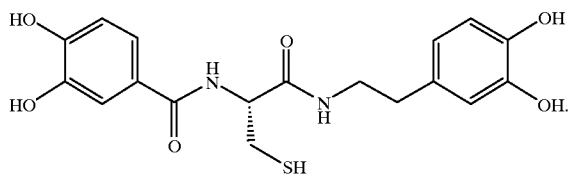

41. A dopamine derivative of formula.

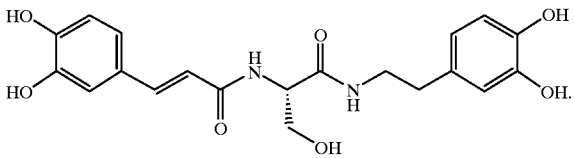

42. A dopamine derivative formula

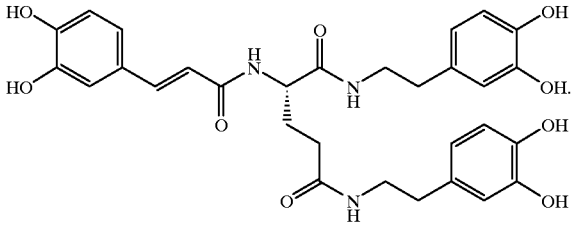

43. A pharmaceutical composition comprising a pharmaceutically acceptable carrier and a pharmaceutically effective amount of at least one hydroxyphenyl derivative as defined in claim 23.

44. A pharmaceutical composition comprising a pharmaceutically acceptable carrier and a pharmaceutically effective amount of at least one dopamine derivative as defined in claim 24.

45. A pharmaceutical composition comprising a pharmaceutically acceptable carrier and a pharmaceutically effective amount of the dopamine derivative as defined in claim 25.

46. A pharmaceutical composition comprising a pharmaceutically acceptable carrier and a pharmaceutically effective amount of the dopamine derivative as defined in claim 26.

47. A pharmaceutical composition comprising a pharmaceutically acceptable carrier and a pharmaceutically effective amount of the dopamine derivative as defined in claim 27.

48. A pharmaceutical composition comprising a pharmaceutically acceptable carrier and a pharmaceutically effective amount of the dopamine derivative as defined in claim 28.

49. A pharmaceutical composition comprising a pharmaceutically acceptable carrier and a pharmaceutically effective amount of the dopamine derivative as defined in claim 29.

50. A pharmaceutical composition comprising a pharmaceutically acceptable carrier and a pharmaceutically effective amount of the dopamine derivative as defined in claim 30.

51. A pharmaceutical composition comprising a pharmaceutically acceptable carrier and a pharmaceutically effective amount of the dopamine derivative as defined in claim 31.

52. A pharmaceutical composition comprising a pharmaceutically acceptable carrier and a pharmaceutically effective amount of the dopamine derivative as defined in claim 32.

53. A pharmaceutical composition comprising a pharmaceutically acceptable carrier and a pharmaceutically effective amount of the compound as defined in claim 33.

54. A pharmaceutical composition comprising a pharmaceutically acceptable carrier and a pharmaceutically effective amount of the dopamine derivative as defined in claim 34.

55. A pharmaceutical composition comprising a pharmaceutically acceptable carrier and a pharmaceutically effective amount of the compound as defined in claim 35.

56. A pharmaceutical composition comprising a pharmaceutically acceptable carrier and a pharmaceutically effective amount of the dopamine derivative as defined in claim 36.

57. A pharmaceutical composition comprising a pharmaceutically acceptable carrier and a pharmaceutically effective amount of the compound as defined in claim 37.

58. A pharmaceutical composition comprising a pharmaceutically acceptable carrier and a pharmaceutically effective amount of the dopamine derivative as defined in claim 38.

59. A pharmaceutical composition comprising a pharmaceutically acceptable carrier and a pharmaceutically effective amount of the dopamine derivative as defined in claim 39.

60. A pharmaceutical composition comprising a pharmaceutically acceptable carrier and a pharmaceutically effective amount of the dopamine derivative as defined in claim 40.

61. A pharmaceutical composition comprising a pharmaceutically acceptable carrier and a pharmaceutically effective amount of the dopamine derivative as defined in claim 41.

62. A pharmaceutical composition comprising a pharmaceutically acceptable carrier and a pharmaceutically effective amount of the dopamine derivative as defined in claim 42.

63. A pharmaceutical composition for inhibiting the activity of HIV integrase comprising a pharmaceutically acceptable carrier and a pharmaceutically effective amount of at least one hydroxyphenyl derivative as defined in claim 1.

64. An hydroxyphenyl derivative selected from the group consisting of a compound of formula I

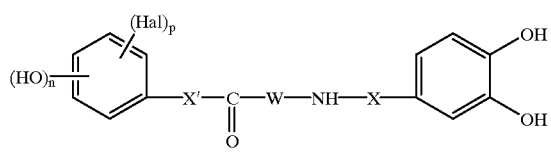

and when a compound of formula I comprises a carboxylic acid group pharmaceutically acceptable salts thereof and when a compound of formula I comprises an amino group pharmaceutically acceptable ammonium salts thereof wherein n is 1, 2 or 3, Hal represents a halogen atom, p is 0, 1 or 2, X and X' each independently represents a single bond, a saturated straight or branched hydrocarbon group of 1 to 4 carbon atoms or a straight or branched hydrocarbon group of 2 to 4 carbon atoms comprising a carbon to carbon double bond, W represents a group of formula

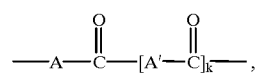

wherein k is 0 or 1, A and A' each independently represents a group of formula

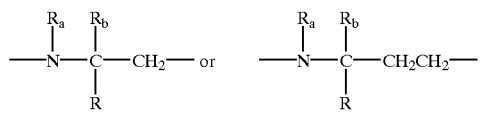

wherein $R_a$ represents H or $CH_3$—, $R_b$ represents H or $CH_3$—, R is selected from the group consisting of H, $CH_3$—, $(CH_3)_2CH$—, $(CH_3)_2CHCH_2$—, $CH_3CH_2CH(CH_3)$—, $C_6H_5CH_2$—, $CH_3SCH_2CH_2$—, $HO_2CCH_2$—, $H_2NC(O)CH_2$—, $HO_2CCH_2CH_2$—, $H_2NC(O)CH_2CH_2$—, $H_2NCH_2CH_2CH_2CH_2$—, $HOCH_2$—, $HO_2C$—, $CH_3CH(OH)$—, $HSCH_2$—, benzyloxycarbonyl, benzyloxycarbonylmethyl,

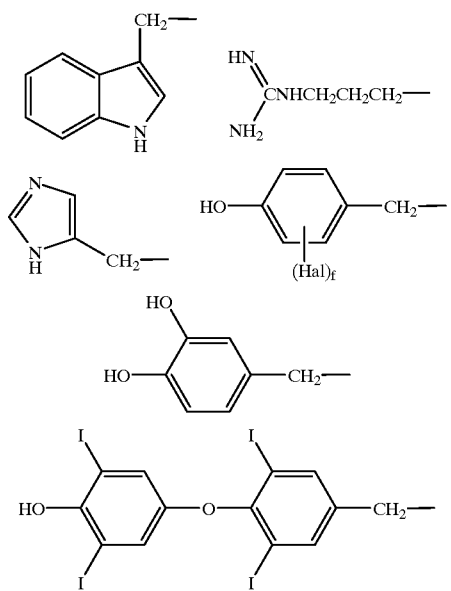

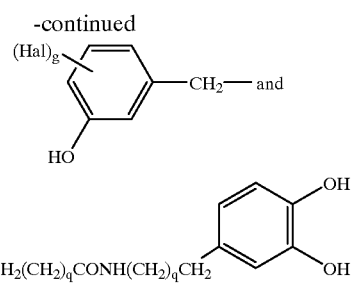

wherein Hal is as defined above and f is 0, 1 or 2, g is 0, 1 or 2, each q is independently 0 or 1.

65. An hydroxyphenyl derivative selected from the group consisting of a compound of formula I

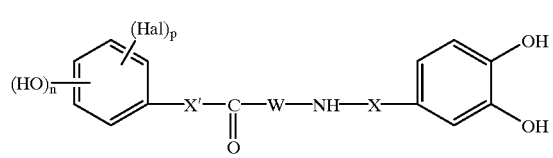

and when a compound of formula I comprises a carboxylic acid group pharmaceutically acceptable salts thereof and when a compound of formula I comprises an amino group pharmaceutically acceptable ammonium salts thereof wherein n is 1, 2 or 3, Hal represents a halogen atom, p is 0, 1 or 2, X and X' each independently represents a single bond, a saturated straight or branched hydrocarbon group of 1 to 4 carbon atoms or a straight or branched hydrocarbon group of 2 to 4 carbon atoms comprising a carbon to carbon double bond, W represents a group of formula

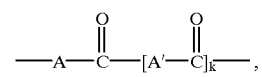

wherein k is 0 or 1, A and A' each independently represents a group of formula

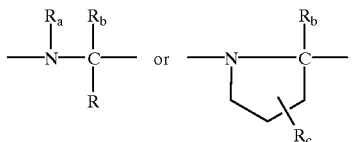

wherein $R_a$ represents H or $CH_3$—, $R_b$ represents H or $CH_3$—, $R_c$ represents H or OH, R is selected from the group consisting of $HO_2C$—, benzyloxycarbonyl, benzyloxycarbonylmethyl, and

wherein each q is independently 0 or 1.

66. A dopamine derivative selected from the group consisting of a compound of formula Ia

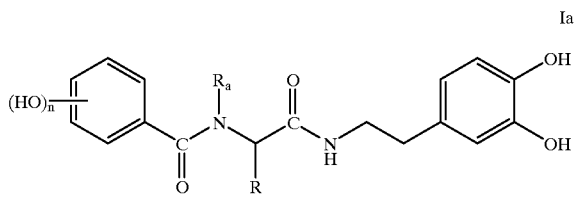

Ia wherein n is 1, 2, or 3, $R_a$ is selected from the group consisting of H and $CH_3$—, R is

wherein q is as defined in claim 1.

67. A dopamine derivative selected from the group consisting of a compound of formula Ic

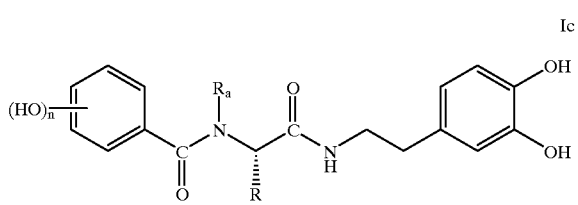

Ic wherein n is 1 or 2, $R_a$ is selected from the group consisting of H and $CH_3$—, R is

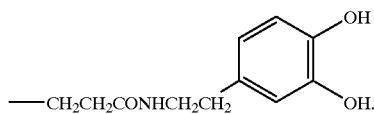

68. An hydroxylphenyl derivative as defined in claim 65 wherein W represents a group of formula

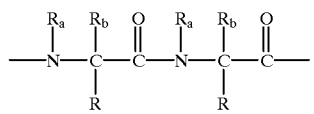

wherein each $R_a$ is independently as defined in claim 65, each $R_b$ is independently as defined in claim 65, and each R is independently as defined in claim 65.

69. A pharmaceutical composition comprising a pharmaceutically acceptable carrier and a pharmaceutically effective amount of at least one hydroxyphenyl derivative as defined in claim 64.

70. A pharmaceutical composition comprising a pharmaceutically acceptable carrier and a pharmaceutically effective amount of at least one hydroxyphenyl derivative as defined in claim 65.

71. A pharmaceutical composition comprising a pharmaceutically acceptable carrier and a pharmaceutically effective amount of at least one dopamine derivative as defined in claim 66.

72. A pharmaceutical composition comprising a pharmaceutically acceptable carrier and a pharmaceutically effective amount of at least one dopamine derivative as defined in claim 67.

73. A pharmaceutical composition comprising a pharmaceutically acceptable carrier and a pharmaceutically effective amount of at least one dopamine derivative as defined in claim 68.

\* \* \* \* \*